US010704054B2

(12) United States Patent
Finch-Savage et al.

(10) Patent No.: US 10,704,054 B2
(45) Date of Patent: Jul. 7, 2020

(54) MODULATION OF SEED VIGOR

(71) Applicant: Syngenta Participations AG, Basel (CH)

(72) Inventors: William Edward Finch-Savage, Wellesbourne (GB); Karl Morris, Leamington Spa (GB); Guy Cameron Barker, Wellesbourne (GB); Tonko Gerhard Bruggink, Enkhuizen (NL); Paul Van Den Wijngaard, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 139 days.

(21) Appl. No.: 16/119,216

(22) Filed: Aug. 31, 2018

(65) Prior Publication Data

US 2019/0078113 A1 Mar. 14, 2019

Related U.S. Application Data

(62) Division of application No. 14/378,349, filed as application No. PCT/EP2013/053845 on Feb. 27, 2013, now Pat. No. 10,087,459.

(30) Foreign Application Priority Data

Feb. 29, 2012 (EP) .................................... 12157514

(51) Int. Cl.
*C12N 15/82* (2006.01)
*C07K 14/415* (2006.01)

(52) U.S. Cl.
CPC ........ *C12N 15/8267* (2013.01); *C07K 14/415* (2013.01); *C12N 15/82* (2013.01); *C12N 15/8261* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 6,184,438 | B1 | 2/2001 | Hannah |
| 2003/0237110 | A9 | 12/2003 | Lalgudi |
| 2007/0039067 | A1 | 2/2007 | Feldmann et al. |
| 2009/0094717 | A1 | 4/2009 | Troukhan et al. |

FOREIGN PATENT DOCUMENTS

| | | |
|---|---|---|
| JP | 2011155840 | 8/2011 |
| WO | 2007078286 A2 | 7/2007 |
| WO | 2011019391 A1 | 2/2011 |

OTHER PUBLICATIONS

Finch-Savage, Williem E. et al: Towards a genetic understanding of seed vigour in small-seeded crops using natural variation in Brassica oleracea, Plant Science, vol. 179, No. 6, 582-589.

Database EMBL (online); "*Brassica rapa* subsp. *pekinensis* clone KBrB043E02, complete sequence", XP002695968.

Rafika Yacoubi et al: "Toward Characterizing Seed Vigor in Alfalfa Through Proteomic Analysis of Germination and Priming"; Journal of Proteome Research. vol. 10. No. 8, Feb. 9, 2011, pp. 3891-3903, XP055312703, US ISSN: 1535-3893.

Mary Bettey et al: "Quantitative genetic analysis of seed vigour and pre-emergence seedling growth traits in Brassica oleracea", New Phytologist, vol. 148, No. 2, Nov. 17, 200, pp. 277-286, XP055312677, GB SSSN: 0028-646X.

Loic Rajjou et al: "Seed Germination and Vigor", Annual Review of Plant Biology, vol. 63, No. 1, Nov. 28, 2011, pp. 507-533, XP055312678, US ISSN: 1543-5008.

David W Still: "The Development of Seed Quality in Brassicas", HortTechnology, Jul. 1, 1999, p. 335, XP055312868.

Morris Karl et al., "Trait to gene analysis reveals that allelic variation in three genes determines seed vigour", New Phytologist 2016, vol. 212, Issu 4, pp. 964-976.

Clerkx, Emile J.M. et al., "Analysis of Natural Allelic Variation of *Arabidopsis* Seed Germination and Seed Longevity Traits between the Accessions Landsberg erecta and Shakdara, Using a New Recombinant Inbred Line Population," Plant Physiology, May 2004, vol. 135, pp. 432-443.

International Preliminary Report on Patentability (IPRP) for International Patent Application No. PCT/EP2013/053845 dated Sep. 2, 2014.

Finch-Savage et al., Plant Science, vol. 179, No. 6, Dec. 1, 2010, pp. 582-589.

Finch-Savage et al., New Phytologist, Tansley Review "Seed dormancy and the control of germination", (2006) vol. 171, pp. 501-523.

Finch-Savage et al., Plant Science, "Sensitivity of Brassica oleracea seed germination to hypoxia: A QTL analysis", vol. 169 (2005) pp. 753-759.

Rae, et al., Heredity, "More QTL for flowering time revealed by substitution lines in Brassica oleracea", vol. 83 (1999) pp. 586-596.

Extended European Search Report for EP20156547.0, dated Apr. 5, 2020.

Bancroft et al., "FP102280", Dec. 2, 2008 (Dec. 2, 2008), XP55688870, Retrieved from the Internet: URL:https://www.ebi.ac.uk/ena/data/view/FP102280&display=text [retrieved on Apr. 23, 2020].

*Primary Examiner* — Elizabeth F Mcelwain
(74) *Attorney, Agent, or Firm* — Karen A. Magri

(57) ABSTRACT

The present invention provides a polynucleotide which enables the modulation of the seed vigour, and in particular enhances the seed vigour, and more particularly enables the modification of the speed of germination. A plant seed comprising the said polynucleotide is also provided. A method of producing the plant seed, method for improving the germination and vigour of plant seed, transgenic plant and the use of the polynucleotide of the invention for producing plants growing seeds with improved germination and vigour characteristics are also provided. The invention particularly concerns *Brassica*, more particularly *Brassica oleracea*.

14 Claims, 4 Drawing Sheets

Specification includes a Sequence Listing.

SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: At3g01190 forward primer

<400> SEQUENCE: 1
ttcttccacg actgcttcg 19

<210> SEQ ID NO 2
<211> LENGTH: 21
<212> TYPE: DNA
<213> ORGANISM: Artificial Sequence
<220> FEATURE:
<223> OTHER INFORMATION: At3g01190 reverse primer

<400> SEQUENCE: 2
ctaacaaaac tgatccgtca c 21

<210> SEQ ID NO 3
<211> LENGTH: 19
<212> TYPE: DNA
<213> ORGANISM: Artificial Sequence
<220> FEATURE:
<223> OTHER INFORMATION: At3g02420 forward primer

<400> SEQUENCE: 3
gttgcgttgc catctgcag 19

<210> SEQ ID NO 4
<211> LENGTH: 20
<212> TYPE: DNA
<213> ORGANISM: Artificial Sequence
<220> FEATURE:
<223> OTHER INFORMATION: At3g02420 reverse primer

<400> SEQUENCE: 4
caggctgaga tagccattgg 20

<210> SEQ ID NO 5
<211> LENGTH: 20
<212> TYPE: DNA
<213> ORGANISM: Artificial Sequence
<220> FEATURE:
<223> OTHER INFORMATION: At3g07130 forward primer

<400> SEQUENCE: 5
ctactaacca tggagttacc 20

<210> SEQ ID NO 6
<211> LENGTH: 18
<212> TYPE: DNA
<213> ORGANISM: Artificial Sequence
<220> FEATURE:
<223> OTHER INFORMATION: At3g07130 reverse primer

<400> SEQUENCE: 6
aacgctggtg ggattcac 18

<210> SEQ ID NO 7
<211> LENGTH: 5108
<212> TYPE: DNA
<213> ORGANISM: Brassica oleracea

<400> SEQUENCE: 7
gtaggccaag ccaagcatat ggatcactta gttgagagaa gttatggcaa gaaataagcc 60
atgcagatta gaaaaagagt gcaacaaact aagtacagta ctaaaagact aagttaataa 120
tacaattaaa ccaaaattaa tggatgagta ccttcacaaa acattagtga attttcagac 180
cctctggacc aatacaagac taaggatgtg agacttaact gacagttagt tcatgtaggg 240
ccaataaaca gctcaaattc gttagctttc aagttccaat tttctgcgtt gtgttttgct 300
ttttgagggt tgatttggaa tttctccaaa gaggtcacat aatttaaaag aaattgatca 360
aaattatatt ggacaaggca agcaaatcca ttaagaagat cacaacaaaa gaaaaattaa 420
aaaccaacaa aagaaatttc ccatttgacg aaggtgatga acaagatcag tacgtatact 480
ccaccaatgc atgacactac tgaaaacata gacaaacaag gtcgtgatag ttgtgaccac 540
ctcacacatg aaaaaactcc atgaatgtca aaagtttgca cgattatgta aacacttaat 600
cacttattca ttgaaggata atgttggaca gaatattatc attgtttcta atggtaagca 660
taagcaaaca ttgtaaaaag aagtcatgat catgctatat cttataggag tttaatttat 720
tccaagttca catttagtga tgctctaatc ttcaacaata aaacataacc aactgatagt 780
cagagtaacc aattgaatgc cagttttcaa aagaaataat acatatctaa ctgatagtca 840
gtcaaatcaa ccaaataagt agaaagaacc aaacaaacac aactaggggt ggacacttcg 900
attattttgt aggttcggtt tggattcggt tcggtttggt taatttattc tagaattttt 960
taaactgaag taaaccataa gtttcagtct gatttgtatt cggcatggtt tgtgtttcag 1020

-continued

```
ttcagtttaa tcggattccc ttaatttaat tcttttaaga aaaatcatgt tttaaaacac   1080
ggtcatgaaa tcatcatgtt ggtgactatg aaaaaataaa ttatataatt aaatctaata   1140
tataactgaa acaaaaatcc taaaaaacca caaaaaaatt tataagaaca caatcaaacc   1200
aaagttaact aaagtaaata gaaaattaaa aaaaaaacaa tgtcaataaa gttaatactg   1260
actttagtgt taggatttag tataaaaatg tttaattcaa ataataacaa agacacattg   1320
gtttttcggt gcaatttgat tcggttcgat tcggttcggt ctgatttttt tgcttgtctg   1380
aacacaacga cggccgacag ataacttttt aaacgttacg tgaaaatgta ttggactatt   1440
gggccttagt aaaggctaat gaacagatta aatgggctta tagacgcaat tgcatggtat   1500
ctatcgggaa gcataaatcg tcaagtaatt caatttaggg gactcatttg caatttgtgc   1560
aaagatttta gctgtacaga gtagggctga acataaaatc cgtaacccga aatccgaacc   1620
gaaccgaaaa acccgatccg tacccgatcc aaaatgtaaa aaatacctca atgaatattg   1680
tagggtgtta taaaatatat ctgaacccga agtgttatta accgaacccg aacggataat   1740
ccgaaaaccc gaaaaaccaa aaaattcgaa aaaatatccg aaaaaactga tccgaatgcg   1800
taaattaata taaaatataa atatttgaaa catacattgg atatgatatc taacaataag   1860
tatttaaaat ttaaataaat actttaaata ctccattata tacaaagaag tatatatttt   1920
ttatgtttta cttttgaatt ttagatttta ctatggatat atccgagccg atccgataca   1980
atccgaatcc gaatgttata tggctacttt ggatatatct gaaccgatcc gaaaccgaag   2040
ttgttatatc cgaatctcat ccgtacttgt aaatttacta gaatgagaca taggggatga   2100
tacaaaatag aaccgaaatc cgaaaaaacc gatccgaacc cgaacgccga ggcctagtac   2160
agagttccga tcagagatag agagaatcct ttgagcgtcg gccttgcttt gtgcgtaggg   2220
atcatctccg actaattgtt gtaattataa agggcggccg cgcctttttta gcggagagat   2280
ggcgagctca cagttcaggt atacgcagac gccgtcgaag gtggtgcacc tgaggaatct   2340
gccgtgggaa tgcgtggaag aggagctcat cgacctatgc aaacgattcg gcaagatcgt   2400
caatacgaag accaatgtcg gcgccaatcg caaccaagcc tttgtcgaat tcgtaacaac   2460
tttttattct cttggatcat cagattgttt ctttttttgg tatctcgttg ttgttttggt   2520
attgttgttt tgaagatgaa actgtatact ttgattcata ttcgcagggt gacgtgaatc   2580
aggcaatatc aatggtttct tactatgctt cgtcttcaga gccggctcag attcgaggga   2640
agactgttta tattcagtac tctaatcgcc atgagattgt caacaatcag agtcctggag   2700
aggtccctgg caatgtcctc ttggtcacct ttgaaggagt ccaatctcac catgtctgca   2760
tcgatgtcat ccatctggta tgtgaatatt cagcttacct tccactattg tttcttgtta   2820
tgttaagtga ttttttttcgt ttcttcgagt agattctaat ctatgaaaat atttcaactt   2880
gttgttatta ggcaaacttc ttttgagtgt atttttttcc acttattgtt agacatacag   2940
tatgtcacat actattgtaa attacagtat atctgacgtt aatgaaaatg ctcgaatcac   3000
agatgttgat gcctctttat tataatcttt ctggagagag tttggaaaat agtttcatgt   3060
tcgtcattct catggacagg tgtcactctg cacttatcta gtcattctct tttttagtct   3120
cctaatttga gtttatttcg attgatttgc ttcccttagt tattatcaat ttactccact   3180
gtattatatg gacatgactc atatctagtc caaacttttg tttcaggtgt tttctgctta   3240
tggcttcgtg cacaaaattg ccacttttga gaaagctgct ggtttccagg ttagagatat   3300
cgagttttgt tttcaaggtc ttgcataaat ctaatgatgt ttaaactcat cgtctgccgt   3360
cataacctgc tcaggcactt gttcagttta ctgatgtgga cactgcctta gcggcaagga   3420
```

ctgcgctgga tggtagaagt atacccaagt atgctcaaat ccttcattca tgcttttgac 3480
cataagataa agctctgttg atggtttctt ccttttcttt tggtaaattc agatatctgc 3540
ttccagaaca tgtaggctca tgcaatttgc gaatgtctta ctcagctcat actgatctaa 3600
atatcaaatt tcagtcccac cgcagcaggt agagttttga gtcctcgcaa atgtgcctct 3660
ccattgttat actgctctta ctgttggaag ccttatggtt gaatagttac ttcatgtgtt 3720
taattctctt acgcactcag ggactacaca aatccatacc ttccggtgaa tcaaaccgct 3780
atggacggtt ctatgcaggt atatttttcc tttgatctaa tcttatctcc aacagcttat 3840
attattctta cactgaatgc gtttgtatta cgttactgat cgtctttgtc catcactgcg 3900
ttcagcctgc tttgggtgct gatggaaaga gggttgaaac tcagagcaac gtcctgcttg 3960
ctttgattga gaatatgcag tacgctgtca ccgtggatgt tcttcacacg gtgaggaaca 4020
acaatatgcc tgtttcttca tctcatcatg ctttcatatc tcaaaattaa ctattccttt 4080
gcttctcata ggtgttttcc gcttatggaa ctgtgcagaa gattgcaata tttgagaaaa 4140
atggttcaac gcaagcctta attcaatact ctggtacatg accttgataa tctgaataca 4200
tatatgattc tactatactt cttttggtta tatggtgaat cttcttatgt gtatgcaaag 4260
agaagagcct aagaatttga atatagtcat cgtttgcttc atgttccgtt ttattgattc 4320
ttctgtagac atttcaacgg cgacgatggc gaaagaagca ctggagggac actgcatata 4380
tgacggaggc tactgtaagc ttcgactaac ttactctcgg catactgatc tcaatgtaaa 4440
ggtacataag atcagttgct ttatgtaccc aaacaaaaag tgcagttaaa gagaataaga 4500
agtgatttct gcaagaaccg catgcttttt tctcatcaac aattgagtga aatctgaatt 4560
cgacattcta gttgattcaa ctaatgattt tcgtcttctt tcttcaggca tttagcgaca 4620
aaagcagaga ctacacactg cctgatctaa gccaactggt gggccaaaag gttccaggag 4680
tggctgcagc tagtgggcca acagatggtt ggcccaatgg gcaggtgcag actcaataca 4740
tgggaagttc gtatatgtac ccaccagctg atcccacagg agcttcacct tcttctggtc 4800
atcctcctta ttatggttga tccatgtact gttttctact ttatataaat ttcggattat 4860
gttgaagact agtttccatg ttataggttt caggtaaaag tgtgttgttc ttttatttgg 4920
ttaaataaac atgggaaaac caataatatt atgtagtata atttataaac attgtgtatt 4980
tgtttctatt tgactttgtt atggagcttc cgaagtgtta gagcttcttt ttctcgtact 5040
ttaaactgtt tcattcctgg atttgtttga agatctgcag acttacactt tagtgacttt 5100
tggtatcc 5108

<210> SEQ ID NO 8
<211> LENGTH: 4992
<212> TYPE: DNA
<213> ORGANISM: Brassica oleracea

<400> SEQUENCE: 8
gtaggccaag ccaagcatat ggatcactta gttgagagaa gttatggcaa gaaataagcc 60
atgcagatta gaaaaagagt gcaacaaact aagtacagta ctaaaagact aagttaataa 120
tacaattaaa ccaaaattaa tggatgagta ccttcacaaa acattagtga attttcagac 180
cctctggacc aatacaagac taaggatgtg agacttaact gacagttagt tcatgtaggg 240
ccaataaaca gctcaaattc gttagctttc aagttccaat tttctgcgtt gtgttttgct 300
ttttgagggt tgatttggaa tttctccaaa gaggtcacat aatttaaaag aaattgatca 360

-continued

```
aaattatatt ggacaaggca agcaaatcca ttaagaagat cacaacaaaa gaaaaataaa    420
aaaccaacaa aagaaatttc ccatttgacg aaggtgatga acaagatcag tacgtatact    480
ccaccaatgc atgacactac tgaaaacata gacaaacaag gtcgtgatag ttgtgaccac    540
ctcacacatg aaaaaactcc atgaatgtca aaagtttgca cgattatgta aacacttaat    600
cacttattca ttgaaggata atgttggaca gaatattatc attgtttcta atggtaagca    660
taagcaaaca ttgtaaaaag aagtcatgat catgctgtat cttataggag tttaatttat    720
tccaagttca catttagtga tgctctaatc ttcaacaata aaacataacc aactgatagt    780
cagagtaacc aattgaatgc cagttttcaa aagaaataat acatatctaa ctgatagtca    840
gtcaaatcaa ccaaataagt agaaagaacc aaacaaacac aactagggtg gacacttcga    900
ttattttgta ggttcggttt ggattcggtt cggtttggtt aatttattct agaatttttt    960
taactgaagt aaaccataag tttcagtctg atttgtattc ggcatggttt gtgtttcagt   1020
tcagtttaat cggattccct taatttaatt cttttaagaa aaatcatgtt ttaaaacatg   1080
gtcatgaaat catcatgttg gttactatga aaaaataaat tatataatta aatctaatat   1140
ataactgaaa caaaaatcct aaaaaaccac aaaaaatttt ataagaacac aatcaaacca   1200
aagttaacta aagtaaatag aaaattaaaa aaaaaaacaa tgtcaataaa gttaatactg   1260
actttagtgt taggatttag tataaaaatg tttaattcaa ataataacaa aaacacattg   1320
gtttttcggt gcaatttgtt cggtttgatt cggttcggtc tgattttttt gcttctctga   1380
acacaacgac ggccgacaga taacttttta aacgttacgt gaaaatgtat tggactattg   1440
ggccttagta aaggctaatg aacagattaa atgggcttat agacgcaatt gcatggtatc   1500
tatcgggaag cataaatcgt caagtaattc aatttagggg actcatttgc aatttgtgca   1560
aagattttag ctgtacagag tagggctggg cataaaatcc gtaacccgaa atccgaaccg   1620
aaccgaaaaa cccgatccgt acccgatcca aaatgtaaaa aatacctcaa tggatattgt   1680
agggtgttat aaaatatatc tgaacccgaa gtgttattaa ccgaacccga acggataatc   1740
cgaaaacccg aaaaaccaaa aaactcgaaa aaatatccga aaaaactgat ccgaatgcgt   1800
aaattaatat aaaatataaa tatttgaaac atacattgga tatgatatct aacaataagt   1860
atttaaaatt taaataagta ctttaaatac tctattatat acaaagaagt atatattttt   1920
tatgttttac ttttgaattt tagattttac tatgtatata tccgagccga tccgatacaa   1980
tccgaatccg aatgttatat ggctattttg gatatatctg aaccgatccg aaaccgaagt   2040
tgttatatcc gaatctcatc cgtactggta aatttactag aatgagacac gggggatgat   2100
acaaaataga accgaaatcc gaaaaaaccg atccgaaccg aacgcccagg cctagtacag   2160
agttccgatc agagatagag agaatccttt gagcgtcggc cttgctttgt gcgtagggat   2220
catctccgac taattgttgt aattataaag ggcggccgcg ccttttttagc ggagagatgg   2280
cgagctcaca gttcaggtat acgcagacgc cgtcgaaggt ggtgcacctg aggaatctgc   2340
cgtgggaatg cgtggaagag gagctcatcg acctatgcaa acgattcggc aagatcgtca   2400
atacgaagac caatgtcggc gccaatcgca accaagcctt tgtcgaattc gtaacaactt   2460
tttattctct tcgatcatca gattgtttct gaagctttgt gatttctatg atgaactctt   2520
tttttttttgg tatctcgttg ttgttttggt attgttgttt tgaagatgaa actgtatact   2580
ttgattcata ttcgcagggt gacgtgaatc aggcaatatc aatggtttct tattatgctt   2640
cgtcttcaga gccggctcag attcgaggga agactgttta tattcagtac tctaatcggc   2700
atgagattgt caacaatcag agtcctggag aggtccctgg caatgtcctc ttggtcacct   2760
```

```
ttgaaggagt ccaatctcac catgtctgca tcgatgtcat ccatctggta tgtgaatatt   2820
cagcttacct tccactattg tttcttgtta tgttaagtga tttttttcgt ttcttcgagt   2880
agattctaat ctatgaaaat atttcaactt gttgttatta ggcaaacttc ttttgagtgt   2940
atttttttcc agttattgtt agacatacag tatgtcacat actattgtaa attacagtat   3000
atctgacgtt aatgaaaatg ctcgaatcac agatgttgat gcctctttat tataatcttt   3060
ctggagagag tttggaaaat agtttcatgt tcgtcattct catggacagg tgtcactctg   3120
cacttatcta gtcattctct tttttagtct cctaacccgg caacatttga gtttatttcg   3180
attgatttgc ttcccttagt tattatcaat ttactccact gtattatatg gacatggctc   3240
atatctagtc caaacttttg tttcaggtgt tttctgctta tggcttcgtg cacaaaattg   3300
ccacttttga gaaagctgct ggtttccagg ttagagatat cgagttttgt tttcaaggtc   3360
ttgcctaaat ctaatgatgt ttaaactcat cgtctgccgt cataacctgc tcaggcactt   3420
gttcagttta ctgatgtgga cactgcctta gcggcaagga ctgcgctgga tggtagaagt   3480
atacccaagt atgctcaaat ccttcattca tgcttttgac cataagataa agctctgttg   3540
atggtttctt ccttttcttt tggtaaattc agatatctgc ttccagaaca tgtaggctca   3600
tgcaatttgc gaatgtctta ctcagctcat actgatctaa atatcaaatt tcagtcccac   3660
cgcagcaggt agagttttga gtcctcgcaa atgtgcctct ccattgttat actgctctta   3720
ctgttggaag ccttatggtt gaatagttac ttcatgtgtt taattctctt acgcactcag   3780
ggactacaca aatccatacc ttccggtgaa tcaaaccgct atggacggtt ctatgcaggt   3840
atatttttcc tttgatctaa tcttatctcc aacagcttat attattctta cactgaatgc   3900
gtttgtatta cgttactgat cgtctttgtc catcactgcg ttcagcctgc tttgggtgct   3960
gatggaaaga gggttgaaac tcagagcaac gtcctgcttg ctttgattga gaatatgcag   4020
tacgctgtca ccgtggatgt tcttcacacg gtgaggaaca acaatatgcc tgtttcttca   4080
tctcatcatg ctttcatatc tcaaaattaa ctattccttt gcttctcata ggtgttttcc   4140
gcttatggaa ctgtgcagaa gattgcaata tttgagaaaa atggttcaac gcaagcctta   4200
attcaatact ctggtacatg accttgataa tctgaataca tatatgattc tactatactt   4260
cttttggtta tatggtgaat cttcttatgt gtatgcaaag agaagagcct aagaatttga   4320
atatagtcat cgtttgcttc atgttccgtt ttattgattc ttctgtagac atttcaacgg   4380
cgacgatggc gaaagaagca ctggagggac actgcatata tgacggaggc tactgtaagc   4440
ttcgactaac ttactctcgg catactgatc tcaatgtaaa ggtacataag atcagttgct   4500
ttatgtaccc aaacaaaaag tgcagtcaaa gagaataata agtgatgtct gcaagaaccg   4560
catgcttttt tctcatcaac aattgagtga aatctgaatt cgacattcta gttgattcaa   4620
ctaatgattt tcgtcttctt tcttcaggca tttagcgaca aaagcagaga ctacacactg   4680
cctgatctaa gccaactggt gggccaaaag gttccaggag tggctgcagc tagtgggcca   4740
acagatggtt ggcccaatgg gcaggtgcag actcaataca tgggaagttc gtatatgtac   4800
ccaccagctg atcccacagg agcttcacct tcttctggtc atcctcctta ttatggttga   4860
tccatgtact gttttctact ttatataaat ttcggattat gttgaagact agtttccatg   4920
ttataggttt caggtaaaag tgtgttgttc ttttatttgg ttaaataaac atgggaaaac   4980
caataatatt at                                                        4992
```

<210> SEQ ID NO 9

-continued

<211> LENGTH: 4993
<212> TYPE: DNA
<213> ORGANISM: Brassica oleracea

<400> SEQUENCE: 9
acgtctatga ccggagtagt ctccttcgtg aagaccggtc actgaaacgc gaatgatgtt 60
cgccataatc tcccatttct ttgaaggtat ttgaacggtt tggtgggttg attgaggcgg 120
atcttaagca gctcgagtgg atctaatcag ctgagagaat cggggagacg attagatcat 180
gcggtgacag attcgagagg aaaccctaat cgccatcgcc gccagagagt ctcatgtgca 240
gtgtgattca tatgcaaatc tcgtggattt ggttgttttt ttctttttca ggtttgattt 300
ggaatttctc taaagaggtc acattaatta aaataaacta gacccttatc cgcgcgccag 360
cgcagatatg aatttttagt ttttaattat ttattttatt caatgatgta tttgtaatat 420
tcgttcatat tatattcgtt aagtaaatat ttttttgtat cttaaactat ctattttttt 480
acgaatgtgt gatatcatat aaaaatatta aaaaatgagt atagagttaa taagataatt 540
ttaaaaacag aaatttttct ttcgtgtgcg atatcatata aataatgatc cgcccagtta 600
acaaaaatca tgattatttt atgtgtaatt ttctttattt tgactatttc cttaaaacta 660
tattaaattt tacatatttt aattagaata tttttaatat ctttaccttt ttatttgaaa 720
tgcaactcaa tatttttttt taacaattat aacaaaatat ttaaaaaata tttttagaat 780
ttgtttgaaa aatatgaaaa ttacatttta aattaaaatt atcctaaaat atgataagtt 840
ttgatgtaaa cgaaaactca aattatgtca aaaataatga tattcaatga taataacaat 900
tttaattgat tattttttaa aaaatacatt tacaaaaata ttgtttgaaa gaaaattcat 960
ttatctttca aatataaaat gaaaatatta taattaaata ataaaaaata taaataaaaa 1020
ccataaattt agcaaatgac aactgagtta tattatgcta aaaaaaaatt tctaacaaaa 1080
tatcaaatga caaatgagtt atgagtaaat aataccatat aatttttaaa aacatagcca 1140
ttcttaaata ttttttgaat aaataattat tttaaattta atcaactaaa aataatatct 1200
gtacaattgt gtgagtcaaa ttctagtttt attgatgcat gttatatatt agtgctgcat 1260
gttttaggta acattttaat gatgcacgtt ttcaaaaatc tccattatta aaattatgca 1320
cgtaatgata actcatgagt tttttttgtt gattaaatga cattatgtcc aaatttattt 1380
aaggatattt cattaaggta agtgaaaaag acaaacaata aaataggaag tttaaaatca 1440
tttaagcata tttcattaat gtaactgaaa agacaagtaa taaattaggc agttttattc 1500
gttttatgat atttcataaa tgcaactgga aaagacaaac aaaaaaaaat agggagttta 1560
attaatgaaa taagaacatt ttcaaatgag tacttctctt ttaataatat agatttcatt 1620
aatgtaactg aaaagacaag taataaatta ggcagtttta ttcgttttag tatatttcat 1680
aaatgcaact gaaaaagaca agaaaaaaaa ataaagaatt taattaatga agtaagaata 1740
ttttcaaatg agtatttctc ttttaataat atagattgat caaaaattat attggataag 1800
gcaagcaaaa tccattgaga agatcacaac aacaaaagaa aggaacaaac acacaaccac 1860
ggcgacagat aactaaaatg tactggacta ttgggccctt aatataggct aatgaacaga 1920
ttaaatgggc taattataga cgtcattgca tggtatccat ctatctggaa gcatagtaat 1980
ttgttttagg ggactggttt gcaattttta cagatatttt agctgtacag tacagagaga 2040
gaatcctttg agcgtcgtcg gccttgcttt gtgtgtaggg atctccgact gactaattgt 2100
tgtaactaca aaagggcgcc ccccgcgcct ttttactaga tggcgagctc atcacagttt 2160
aggtataccc agacgccgtc gaaggtggtg cacctgagga atctgccgtg ggaatgcgtg 2220

-continued

```
gaagaggagc tcatcgacct atgcaaacga ttcggcaaga tcgtcaatac gaagaccaat   2280
gtcggcgcca atcgcaacca agcctttgtc gaattcgtaa gaacttttta ttctcttgga   2340
tcatcagatt gttgcttccc ccccaatgga tttggttaga aattgaataa aaaaaggact   2400
cgaactcttt ttttggtatc tcgttgttgt tttgaagatg aaactgtata ctttgattca   2460
tattcgcagg gtgacgtgaa tcaggcaata tcaatggttt cttactatgc ttcgtcttca   2520
gagccggctc agattcgagg gaagactgtt tatattcagt actctaatcg ccatgagatt   2580
gtcaacaatc agagtcctgg agaggtccct ggcaatgtcc tattggtcac ctttgaagga   2640
gtccaatctc accatgtctg catcgatgtc atccatctgg tatgtgaata ttcagcttac   2700
cttccactat tgtttcttgt tatagtgatt tttttcgttt cttcgagtag attctaatct   2760
atgaaaatat ttcaacttgt tgttattagg caaacttctt ttgagtgtat ttttttccag   2820
ttattgttag acatacagta tgtcacatac tattgtaaat tacagtatat ctgacgttaa   2880
tgaaaatgct cgaatcacag atgttgatgc ctctttatta taatctttct ggagagagtt   2940
tggaaaatag tttcatgttc gtctttctca tggacaggtg tcactctgca cttatctagt   3000
cattctcttt tttagtctcc taatttgagt ttatttcgat tgatttgctt cccttagtta   3060
ttatcaattt actccactgt attatatgga catgactcat atctagtcca aacttttgtt   3120
tcaggtgttt tctgcttatg gcttcgtgca caaaattgcc acttttgaga aagctgctgg   3180
tttccaggtt agagatatcg agttttgttt tcaaggtctt gcctttttca taaaatctaa   3240
tgatgtttaa actcatcatc tgccgtcata acctgctcag gcacttgttc agtttactga   3300
tgtggacact gccttagcgg caaggactgc gctggatggt agaagtatac ccacgtatgc   3360
tcaaatcctt cattcatgct tttgaccata agataaagct ctgttgatgg tttcttcctt   3420
ttcttttggt aaattcagat atctgcttcc agaacatgta ggctcatgca atttgcgaat   3480
gtcttactca gcccacactg atctaaatat caaatttcag tcccaccgca gcaggtagag   3540
ttttgagtcc tcgcaaatgt gccattccat tgttttactg ctcctactgt tggaagcctt   3600
atggttgaat agttgattca tgtgttttga ttttctgacg tactcaggga ctacacaaat   3660
ccatatcttc cggtgaatca aactgctatg gatggttcta tgcaggtaaa tatttcctct   3720
ttctagtcta tctccaacag cttagacaat tcttacattg aatgcgttac tgattgtctt   3780
tgacgtcatt gcattcagcc tgctttgggt gctgatggaa agagggtaga aactcagagc   3840
aacgtcctac ttgctttgat tgagaatatg caatacgctg tcacacggtg aggaacacca   3900
ttatgcacgt ttctgcatct cagcatcctt tcatttctca aaattaatta tttcctttgc   3960
ttgtcatagg tgttttccgc ttatgggact gtgcagaaga ttgcaatatt tgagaaaaat   4020
ggttcaacgc aagccttaat tcaatactct ggtacatgac cttgatgatc tgaatacata   4080
tattattata ctatacttct ttcggttata tggcgaatca tcttatgtgt atgctaagaa   4140
tttgaatagt catcatttgc ttcatgttcc gttttcttga ttcttctgta gacataccaa   4200
cggcgacaat agcgaaagaa gcattggagg gacactgcat atatgacggg aggctactgt   4260
aagcttcgac taacatactc gtcatactga tctcaatgta aaggtacgta agatcagttg   4320
ctttcttgat ttgtgcaccc aaacaaaaaa gcttggggaa agagaataat aacttatgtc   4380
tgcaagaacc atatgctatt ttttttctct tcaacaattg tatgaaatct gaattcgact   4440
ttctagttta ttcaactagt gatttttcgt cttctttctt caggcattta gtgacaaaag   4500
cggagactac acactgcctg atctaagcca actggtgggc caaaaggttc caggagtggc   4560
```

```
cgctgctagt gggccaacag attgttggca caatgggcag gtgcagactc aatacacaag   4620
aagttcatat atgtacccac tgtaagcaaa ggtactagat tttgataaag cgcgagttta   4680
tttttaaatt tttttcaatt gacaaatatt tagtaaatgt catattttca tatatttgtg   4740
ttttatttta taaaagactt aaacttttta tctttattta tcgtatttta ttttaaatga   4800
ctatttatgt ttaaaaaatt aaactttatt tctttaatga attaagttga tataactctg   4860
ataaattaat tttattatgt ggttaatatt ttaattaaaa aaaattatat acttttaata   4920
aagatttgta tttttcaatg aaaaaattca atttttttta tgaatgctta aattatatta   4980
agaaaagaaa aga                                                      4993
```

<210> SEQ ID NO 10
<211> LENGTH: 4992
<212> TYPE: DNA
<213> ORGANISM: Brassica oleracea

<400> SEQUENCE: 10

```
acgtctatga ccggagtagt ctccttcgtg aagaccggtc actgaaacgc gaatgatgtt     60
cgccataatc tcccatttct ttgaaggtat ttgaacggtt tggtgggttg attgaggcgg    120
atcttaagca gctcgagtgg atctaatcag ctgagagaat cggggagacg attagatcat    180
gcggtgacag attcgagagg aaaccctaat cgccatcgcc gccagagagt ctcatgtgca    240
gtgtgattca tatgcaaatc tcgtggattt ggttgttttt ttctttttca ggtttgattt    300
ggaatttctc taaagaggtc acattaatta aaataaacta gacccttatc cgcgcgccag    360
cgcagatatg aatttttagt ttttaattat ttattttatt caatgatgta tttgtaatat    420
tcgttcatat tatattcgtt aagtaaatat ttttttgtat cttaaactat ctattttttt    480
acgaatgtgt gatatcatat aaaaatatta aaaaatgagt atagagttaa taagataatt    540
ttaaaaacag aaatttttct ttcgtgtgcg atatcatata aataatgatc cgcccagtta    600
acaaaaatca tgattatttt atgtgtaatt ttctttattt tgactatttc cttaaaacta    660
tattaaattt tacatatttt aattagaata tttttaatat ctttaccttt ttatttgaaa    720
tgcaactcaa tatttttttt aacaattata acaaaatatt taaaaaatat ttttagaatt    780
tgtttgaaaa atatgaaaat tacattttaa attaaaatta tcctaaaata tgataagttt    840
tgatgtaaac gaaaactcaa attatgtcaa aaataatgat attcaatgat aataacaatt    900
ttaattgatt atttttttaaa aaatacattt acaaaaatat tgtttgaaag aaaattcatt    960
tatctttcaa atataaaatg aaaatattat aattaaataa taaaaaatat aaataaaaac   1020
cataaattta gcaaatgaca actgagttat attatgctaa aaaaaaattt ctaacaaaat   1080
atcaaatgac aaatgagtta tgagtaaata ataccatata atttttaaaa acatagccat   1140
tcttaaatat tttttgaata aataattatt ttaaatttaa tcaactaaaa ataatatctg   1200
tacaattgtg tgagtcaaat tctagtttta ttgatgcatg ttatatatta gtgctgcatg   1260
ttttaggtaa cattttaatg atgcacgttt tcaaaaatct ccattattaa aattatgcac   1320
gtaatgataa ctcatgagtt ttttttgttg attaaatgac attatgtcca aatttattta   1380
aggatatttc attaaggtaa gtgaaaaaga caaacaataa aataggaagt ttaaaatcat   1440
ttaagcatat ttcattaatg taactgaaaa gacaagtaat aaattaggca gttttattcg   1500
ttttatgata tttcataaat gcaactggaa aagacaaaca aaaaaaaata gggagtttaa   1560
ttaatgaaat aagaacattt tcaaatgagt acttctcttt taataatata gatttcatta   1620
atgtaactga aaagacaagt aataaattag gcagttttat tcgttttagg atatttcata   1680
```

```
aatgcaactg aaaaagacaa gaaaaaaaaa taaagaattt aattaatgaa gtaagaatat   1740
tttcaaatga gtacttctct tttaataata tagattgatc aaaaattata ttggataagg   1800
caagcaaaat ccattgagaa gatcacaaca acaaaagaaa ggaacaaaca cacaaccacg   1860
gcgacagata actaaaatgt actggactat tgggccctta atataggcta atgaacagat   1920
taaatgggct aattatagac gtcattgcat ggtatccatc tatctggaag catagtaatt   1980
tgttttaggg gactggtttg caatttttac agatatttta gctgtacagt acagagagag   2040
aatcctttga gcgtcgtcgg ccttgctttg tgtgtaggga tctccgactg actaattgtt   2100
gtaactacaa aagggcgccc cccgcgcctt tttactagat ggcgagctca tcacagttta   2160
ggtataccca gacgccgtcg aaggtggtgc acctgaggaa tctgccgtgg gaatgcgtgg   2220
aagaggagct catcgaccta tgcaaacgat tcggcaagat cgtcaatacg aagaccaatg   2280
tcggcgccaa tcgcaaccaa gcctttgtcg aattcgtaac aactttttat tctcttggat   2340
catcagattg ttgcttcccc cccaatggat ttggttagaa attgaataaa aaaaggactc   2400
gaactctttt tttggtatct cgttgttgtt ttgaagatga aactgtatac tttgattcat   2460
attcgcaggg tgacgtgaat caggcaatat caatggtttc ttactatgct tcgtcttcag   2520
agccggctca gattcgaggg aagactgttt atattcagta ctctaatcgc catgagattg   2580
tcaacaatca gagtcctgga gaggtccctg gcaatgtcct attggtcacc tttgaaggag   2640
tccaatctca ccatgtctgc atcgatgtca tccatctggt atgtgaatat tcagcttacc   2700
ttccactatt gtttcttgtt atagtgattt ttttcgtttc ttcgagtaga ttctaatcta   2760
tgaaaatatt tcaacttgtt gttattaggc aaacttcttt tgagtgtatt tttttccagt   2820
tattgttaga catacagtat gtcacatact attgtaaatt acagtatatc tgacgttaat   2880
gaaaatgctc gaatcacaga tgttgatgcc tctttattat aatctttctg gagagagttt   2940
ggaaaatagt ttcatgttcg tctttctcat ggacaggtgt cactctgcac ttatctagtc   3000
attctctttt ttagtctcct aatttgagtt tatttcgatt gatttgcttc ccttagttat   3060
tatcaattta ctccactgta ttatatggac atgactcata tctagtccaa acttttgttt   3120
caggtgtttt ctgcttatgg cttcgtgcac aaaattgcca cttttgagaa agctgctggt   3180
ttccaggtta gagatatcga gttttgtttt caaggtcttg ccttttttcat aaaatctaat   3240
gatgtttaaa ctcatcatct gccgtcataa cctgctcagg cacttgttca gtttactgat   3300
gtggacactg ccttagcggc aaggactgcg ctggatggta gaagtatacc cacgtatgct   3360
caaatccttc attcatgctt ttgaccataa gataaagctc tgttgatggt ttcttccttt   3420
tcttttggta aattcagata tctgcttcca gaacatgtag gctcatgcaa tttgcgaatg   3480
tcttactcag cccacactga tctaaatatc aaatttcagt cccaccgcag caggtagagt   3540
tttgagtcct cgcaaatgtg ccattccatt gttttactgc tcctactgtt ggaagcctta   3600
tggttgaata gttgattcat gtgttttgat tttctgacgt actcagggac tacacaaatc   3660
catatcttcc ggtgaatcaa actgctatgg atggttctat gcaggtaaat atttcctctt   3720
tctagtctat ctccaacagc ttagacaatt cttacattga atgcgttact gattgtcttt   3780
gacgtcattg cattcagcct gctttgggtg ctgatggaaa gagggtagaa actcagagca   3840
acgtcctact tgctttgatt gagaatatgc aatacgctgt cacacggtga ggaacaccat   3900
tatgcacgtt tctgcatctc agcatccttt catttctcaa aattaattat ttcctttgct   3960
tgtcataggt gttttccgct tatgggactg tgcagaagat tgcaatattt gagaaaaatg   4020
```

```
gttcaacgca agccttaatt caatactctg gtacatgacc ttgatgatct gaatacatat   4080

attattatac tatacttctt tcggttatat ggcgaatcat cttatgtgta tgctaagaat   4140

ttgaatagtc atcatttgct tcatgttccg ttttcttgat tcttctgtag acataccaac   4200

ggcgacaata gcgaaagaag cattggaggg acactgcata tatgacggga ggctactgta   4260

agcttcgact aacatactcg tcatactgat ctcaatgtaa aggtacgtaa gatcagttgc   4320

tttcttgatt tgtgcaccca aacaaaaaag cttggggaaa gagaataata acttatgtct   4380

gcaagaacca tatgctattt tttttctctt caacaattgt atgaaatctg aattcgactt   4440

tctagtttat tcaactagtg atttttcgtc ttctttcttc aggcatttag cgacaaaagc   4500

ggagactaca cactgcctga tctaagccaa ctggtgggcc aaaaggttcc aggagtggcc   4560

gctgctagtg ggccaacaga ttgttggcac aatgggcagg tgcagactca atacacaaga   4620

agttcatata tgtacccact gtaagcaaag gtactagatt ttgataaagc gcgagtttat   4680

ttttaatttt ttttcaattg acaaatattt agtaaatgtc atattttcat atatttgtgt   4740

tttattttat aaaagactta aactttttat ctttatttat cgtattttat tttaaatgac   4800

tatttatgtt taaaaaatta aactttattt ctttaatgaa ttaagttgat ataactctga   4860

taaattaatt ttattatgtg gttaatattt taattaaaaa aaattatata cttttaataa   4920

agatttgtat ttttcaatga aaaaattcaa tttttttat gaatgcttaa attatattaa    4980

gaaaagaaaa ga                                                       4992


<210> SEQ ID NO 11
<211> LENGTH: 395
<212> TYPE: PRT
<213> ORGANISM: Brassica oleracea

<400> SEQUENCE: 11

Met Ala Ser Ser Gln Phe Arg Tyr Thr Gln Thr Pro Ser Lys Val Val
1               5                   10                  15

His Leu Arg Asn Leu Pro Trp Glu Cys Val Glu Glu Glu Leu Ile Asp
            20                  25                  30

Leu Cys Lys Arg Phe Gly Lys Ile Val Asn Thr Lys Thr Asn Val Gly
        35                  40                  45

Ala Asn Arg Asn Gln Ala Phe Val Glu Phe Gly Asp Val Asn Gln Ala
    50                  55                  60

Ile Ser Met Val Ser Tyr Tyr Ala Ser Ser Ser Glu Pro Ala Gln Ile
65                  70                  75                  80

Arg Gly Lys Thr Val Tyr Ile Gln Tyr Ser Asn Arg His Glu Ile Val
                85                  90                  95

Asn Asn Gln Ser Pro Gly Glu Val Pro Gly Asn Val Leu Leu Val Thr
            100                 105                 110

Phe Glu Gly Val Gln Ser His His Val Cys Ile Asp Val Ile His Leu
        115                 120                 125

Val Phe Ser Ala Tyr Gly Phe Val His Lys Ile Ala Thr Phe Glu Lys
    130                 135                 140

Ala Ala Gly Phe Gln Ala Leu Val Gln Phe Thr Asp Val Asp Thr Ala
145                 150                 155                 160

Leu Ala Ala Arg Thr Ala Leu Asp Gly Arg Ser Ile Pro Lys Tyr Leu
                165                 170                 175

Leu Pro Glu His Val Gly Ser Cys Asn Leu Arg Met Ser Tyr Ser Ala
            180                 185                 190

His Thr Asp Leu Asn Ile Lys Phe Gln Ser His Arg Ser Arg Asp Tyr
```

```
        195                 200                 205

Thr Asn Pro Tyr Leu Pro Val Asn Gln Thr Ala Met Asp Gly Ser Met
    210                 215                 220

Gln Pro Ala Leu Gly Ala Asp Gly Lys Arg Val Glu Thr Gln Ser Asn
225                 230                 235                 240

Val Leu Leu Ala Leu Ile Glu Asn Met Gln Tyr Ala Val Thr Val Asp
                245                 250                 255

Val Leu His Thr Val Phe Ser Ala Tyr Gly Thr Val Gln Lys Ile Ala
            260                 265                 270

Ile Phe Glu Lys Asn Gly Ser Thr Gln Ala Leu Ile Gln Tyr Ser Asp
        275                 280                 285

Ile Ser Thr Ala Thr Met Ala Lys Glu Ala Leu Glu Gly His Cys Ile
    290                 295                 300

Tyr Asp Gly Gly Tyr Cys Lys Leu Arg Leu Thr Tyr Ser Arg His Thr
305                 310                 315                 320

Asp Leu Asn Val Lys Ala Phe Ser Asp Lys Ser Arg Asp Tyr Thr Leu
                325                 330                 335

Pro Asp Leu Ser Gln Leu Val Gly Gln Lys Val Pro Gly Val Ala Ala
            340                 345                 350

Ala Ser Gly Pro Thr Asp Gly Trp Pro Asn Gly Gln Val Gln Thr Gln
        355                 360                 365

Tyr Met Gly Ser Ser Tyr Met Tyr Pro Pro Ala Asp Pro Thr Gly Ala
    370                 375                 380

Ser Pro Ser Ser Gly His Pro Pro Tyr Tyr Gly
385                 390                 395


<210> SEQ ID NO 12
<211> LENGTH: 395
<212> TYPE: PRT
<213> ORGANISM: Brassica oleracea

<400> SEQUENCE: 12

Met Ala Ser Ser Gln Phe Arg Tyr Thr Gln Thr Pro Ser Lys Val Val
1               5                   10                  15

His Leu Arg Asn Leu Pro Trp Glu Cys Val Glu Glu Glu Leu Ile Asp
            20                  25                  30

Leu Cys Lys Arg Phe Gly Lys Ile Val Asn Thr Lys Thr Asn Val Gly
        35                  40                  45

Ala Asn Arg Asn Gln Ala Phe Val Glu Phe Gly Asp Val Asn Gln Ala
    50                  55                  60

Ile Ser Met Val Ser Tyr Tyr Ala Ser Ser Ser Glu Pro Ala Gln Ile
65                  70                  75                  80

Arg Gly Lys Thr Val Tyr Ile Gln Tyr Ser Asn Arg His Glu Ile Val
                85                  90                  95

Asn Asn Gln Ser Pro Gly Glu Val Pro Gly Asn Val Leu Leu Val Thr
            100                 105                 110

Phe Glu Gly Val Gln Ser His His Val Cys Ile Asp Val Ile His Leu
        115                 120                 125

Val Phe Ser Ala Tyr Gly Phe Val His Lys Ile Ala Thr Phe Glu Lys
    130                 135                 140

Ala Ala Gly Phe Gln Ala Leu Val Gln Phe Thr Asp Val Asp Thr Ala
145                 150                 155                 160

Leu Ala Ala Arg Thr Ala Leu Asp Gly Arg Ser Ile Pro Lys Tyr Leu
                165                 170                 175
```

Leu Pro Glu His Val Gly Ser Cys Asn Leu Arg Met Ser Tyr Ser Ala
180 185 190

His Thr Asp Leu Asn Ile Lys Phe Gln Ser His Arg Ser Arg Asp Tyr
195 200 205

Thr Asn Pro Tyr Leu Pro Val Asn Gln Thr Ala Met Asp Gly Ser Met
210 215 220

Gln Pro Ala Leu Gly Ala Asp Gly Lys Arg Val Glu Thr Gln Ser Asn
225 230 235 240

Val Leu Leu Ala Leu Ile Glu Asn Met Gln Tyr Ala Val Thr Val Asp
245 250 255

Val Leu His Thr Val Phe Ser Ala Tyr Gly Thr Val Gln Lys Ile Ala
260 265 270

Ile Phe Glu Lys Asn Gly Ser Thr Gln Ala Leu Ile Gln Tyr Ser Asp
275 280 285

Ile Ser Thr Ala Thr Met Ala Lys Glu Ala Leu Glu Gly His Cys Ile
290 295 300

Tyr Asp Gly Gly Tyr Cys Lys Leu Arg Leu Thr Tyr Ser Arg His Thr
305 310 315 320

Asp Leu Asn Val Lys Ala Phe Ser Asp Lys Ser Arg Asp Tyr Thr Leu
325 330 335

Pro Asp Leu Ser Gln Leu Val Gly Gln Lys Val Pro Gly Val Ala Ala
340 345 350

Ala Ser Gly Pro Thr Asp Gly Trp Pro Asn Gly Gln Val Gln Thr Gln
355 360 365

Tyr Met Gly Ser Ser Tyr Met Tyr Pro Pro Ala Asp Pro Thr Gly Ala
370 375 380

Ser Pro Ser Ser Gly His Pro Pro Tyr Tyr Gly
385 390 395

<210> SEQ ID NO 13
<211> LENGTH: 326
<212> TYPE: PRT
<213> ORGANISM: Brassica oleracea

<400> SEQUENCE: 13

Met Ala Ser Ser Ser Gln Phe Arg Tyr Thr Gln Thr Pro Ser Lys Val
1 5 10 15

Val His Leu Arg Asn Leu Pro Trp Glu Cys Val Glu Glu Glu Leu Ile
20 25 30

Asp Leu Cys Lys Arg Phe Gly Lys Ile Val Asn Thr Lys Thr Asn Val
35 40 45

Gly Ala Asn Arg Asn Gln Ala Phe Val Glu Phe Gly Asp Val Asn Gln
50 55 60

Ala Ile Ser Met Val Ser Tyr Tyr Ala Ser Ser Ser Glu Pro Ala Gln
65 70 75 80

Ile Arg Gly Lys Thr Val Tyr Ile Gln Tyr Ser Asn Arg His Glu Ile
85 90 95

Val Asn Asn Gln Ser Pro Gly Glu Val Pro Gly Asn Val Leu Leu Val
100 105 110

Thr Phe Glu Gly Val Gln Ser His His Val Cys Ile Asp Val Ile His
115 120 125

Leu Val Phe Ser Ala Tyr Gly Phe Val His Lys Ile Ala Thr Phe Glu
130 135 140

Lys Ala Ala Gly Phe Gln Ala Leu Val Gln Phe Thr Asp Val Asp Thr
145 150 155 160

```
Ala Leu Ala Ala Arg Thr Ala Leu Asp Gly Arg Ser Ile Pro Thr Tyr
                165                 170                 175

Leu Leu Pro Glu His Val Gly Ser Cys Asn Leu Arg Met Ser Tyr Ser
            180                 185                 190

Ala His Thr Asp Leu Asn Ile Lys Phe Gln Ser His Arg Ser Arg Asp
        195                 200                 205

Tyr Thr Asn Pro Tyr Leu Pro Val Asn Gln Thr Ala Met Asp Gly Ser
    210                 215                 220

Met Gln Val Phe Ser Ala Tyr Gly Thr Val Gln Lys Ile Ala Ile Phe
225                 230                 235                 240

Glu Lys Asn Gly Ser Thr Gln Ala Leu Ile Gln Tyr Ser Asp Ile Pro
                245                 250                 255

Thr Ala Thr Ile Ala Lys Glu Ala Leu Glu Gly His Cys Ile Tyr Asp
            260                 265                 270

Gly Arg Leu Leu Asp Lys Ser Gly Asp Tyr Thr Leu Pro Asp Leu Ser
        275                 280                 285

Gln Leu Val Gly Gln Lys Val Pro Gly Val Ala Ala Ala Ser Gly Pro
    290                 295                 300

Thr Asp Cys Trp His Asn Gly Gln Val Gln Thr Gln Tyr Thr Arg Ser
305                 310                 315                 320

Ser Tyr Met Tyr Pro Leu
                325


<210> SEQ ID NO 14
<211> LENGTH: 326
<212> TYPE: PRT
<213> ORGANISM: Brassica oleracea

<400> SEQUENCE: 14

Met Ala Ser Ser Ser Gln Phe Arg Tyr Thr Gln Thr Pro Ser Lys Val
1               5                   10                  15

Val His Leu Arg Asn Leu Pro Trp Glu Cys Val Glu Glu Glu Leu Ile
            20                  25                  30

Asp Leu Cys Lys Arg Phe Gly Lys Ile Val Asn Thr Lys Thr Asn Val
        35                  40                  45

Gly Ala Asn Arg Asn Gln Ala Phe Val Glu Phe Gly Asp Val Asn Gln
    50                  55                  60

Ala Ile Ser Met Val Ser Tyr Tyr Ala Ser Ser Ser Glu Pro Ala Gln
65                  70                  75                  80

Ile Arg Gly Lys Thr Val Tyr Ile Gln Tyr Ser Asn Arg His Glu Ile
                85                  90                  95

Val Asn Asn Gln Ser Pro Gly Glu Val Pro Gly Asn Val Leu Leu Val
            100                 105                 110

Thr Phe Glu Gly Val Gln Ser His His Val Cys Ile Asp Val Ile His
        115                 120                 125

Leu Val Phe Ser Ala Tyr Gly Phe Val His Lys Ile Ala Thr Phe Glu
    130                 135                 140

Lys Ala Ala Gly Phe Gln Ala Leu Val Gln Phe Thr Asp Val Asp Thr
145                 150                 155                 160

Ala Leu Ala Ala Arg Thr Ala Leu Asp Gly Arg Ser Ile Pro Thr Tyr
                165                 170                 175

Leu Leu Pro Glu His Val Gly Ser Cys Asn Leu Arg Met Ser Tyr Ser
            180                 185                 190

Ala His Thr Asp Leu Asn Ile Lys Phe Gln Ser His Arg Ser Arg Asp
```

-continued

```
        195                 200                 205

Tyr Thr Asn Pro Tyr Leu Pro Val Asn Gln Thr Ala Met Asp Gly Ser
    210                 215                 220

Met Gln Val Phe Ser Ala Tyr Gly Thr Val Gln Lys Ile Ala Ile Phe
225                 230                 235                 240

Glu Lys Asn Gly Ser Thr Gln Ala Leu Ile Gln Tyr Ser Asp Ile Pro
                245                 250                 255

Thr Ala Thr Ile Ala Lys Glu Ala Leu Glu Gly His Cys Ile Tyr Asp
            260                 265                 270

Gly Arg Leu Leu Asp Lys Ser Gly Asp Tyr Thr Leu Pro Asp Leu Ser
        275                 280                 285

Gln Leu Val Gly Gln Lys Val Pro Gly Val Ala Ala Ala Ser Gly Pro
    290                 295                 300

Thr Asp Cys Trp His Asn Gly Gln Val Gln Thr Gln Tyr Thr Arg Ser
305                 310                 315                 320

Ser Tyr Met Tyr Pro Leu
                325


<210> SEQ ID NO 15
<211> LENGTH: 3061
<212> TYPE: DNA
<213> ORGANISM: Brassica oleracea

<400> SEQUENCE: 15

aaaaagcagg ctaagagtgt aagcgaccca tttcacatcg gatctaaaaa tcatataatc     60

tagagtctga caagaatcaa cgttgataga gagtgcgaga gaatagtaca gagccagtcg    120

tcgaggtaga aatgtttgtc ctgagcccaa atggtatagt tgatattggg attccagaac    180

ttgttatcac ccactatcca tctcttagcg gccacctcag tcaccggagc tgccgcaaga    240

aaagccagaa ccattgccgc agccatcaac gcaagtctag ccatagatca ctctagaaag    300

aaaaagaagc tcagtgctta atgactctta gtcttatctc tcaagaaata gcagttttat    360

gaatgaatgt atatgagcga gtggggctgt ttccaagtca aatcagacat acaaatttct    420

cgttttacgg ggaaaagatc tctcaagatc cgtaatttct tcaactaacg tttggaattt    480

tattactact ttaatcaacc tcgatgttga cgatgaagta cacgttaatt aaaggtacgc    540

gttatatagt taaaggagta attagatttt aattgctggc attattatta tttttctctg    600

gtatattttt aaaggaatat tttctcacct tttaggcggg aatttatttc cattttcttc    660

tttcaagggt tcagagattc aattccttta ttaacatacg aaatgagtat atagtatctt    720

ttgaatattt aaataattaa aataaaaata aattaccata acagtgatac atatcaaaat    780

ttccaaaact aatgtgagta cttatattag ttgtacttct tagtaaaata acgagatatg    840

ttatggctcg tcgcatacaa caaagcagag catatgttcc cgcaataaca tgcacacgca    900

actgatagca cgtcgtaacc atttccgcga accaaccaat ggatattgta attcgataag    960

acgacgtcgt gttgttgacc acgaatattt cttaaatttc cttttatctt ttgtttttga   1020

cgtcatcaca ttggtttatg tccacacgat atcagtcata aaatccacgt agggaacgac   1080

tatccattac acccatccac gtgttctcat aacagcttct agttccatta gctgaacgaa   1140

caatagaaac agagcatcga actgagaaag aagaagaaga agggaagcaa gagaaatggc   1200

ggcagcggcc atggccgttc atctcccgaa acattcatcg tttcttccta atcccaagct   1260

tccattgaat caaaactcta acttcctcgg tgtgtccttg aagatcggtc gacccatgtc   1320

cgttaaccgg aaaatgaaag gtccggttac ggtttcagct gcttcgaccg tcgaaggcga   1380
```

```
tcgaagcaaa cagttttaca taaacttcac tggattccca tttcctcttg gtcctttcct   1440

taaccggcgc accatcagaa ccgaggttag gctttctcca tccctcttga gttttgattt   1500

gaactcgttg agaatcccat atggatgtta tgcaggcggt taaaggaagc atatggatgt   1560

ttgaacaaga acaagcttta ggtttcagca gtgtctctac caatataaga atgactgtca   1620

tcagactcaa atccggtggc ttatgggttc atgcccctat tgctcccacc aaagagtgta   1680

ttcaggttcc cccttttat tcattatcct tgataaagta tcatcctttc ttatcatttg   1740

ataataacca atgtctaaac tctttttgg gttgttttgc aaactttttc tttgaggcag   1800

cttattgagg agttgggagc tccggttgag tacattgtcc tgccaacttt tgcttacgag   1860

cacaagatct tcgtcggtcc cttctctaga aagttcccca aggctcaagt atgggtggcg   1920

ccaagacaat ggagctggcc actgaactta ccactcgagt tttcggtat ctttcgcgct   1980

aaaaccatta aagacggaga cttatctacc ccgtgggctg atgagatcga gcagaaagtc   2040

ttaagctctc ctgaagtcgg tacgttcctt cactttctca atcttgttgg ccctccttag   2100

ccaagcctca gtgaaacatt cgcctaaacc cgcactctcc tcctcttccc tccaaaatat   2160

ttgaaaagag ttatatatac atagcctccc aagttattaa aaaaaacgtt ttgtctccca   2220

aactattgaa atctttatca aattgtctat agcctccaaa atccgagggt cggtcctgta   2280

cttatgaaat aataatatac aggaatagga ccgtatgtgg aagtagcgtt ctaccataag   2340

cgttcaagaa ctctattagt cactgatgct gtgatcttcg tcccacggaa gccgccatcg   2400

agtatcagca gcgagtcctt gctggcctct gctaagaacg gactggctgt gaagatactt   2460

agcaaaggca aacaagtacc tgatgaccct gtcgttgata ccccaaacac ccgccaaaaa   2520

ggtcagccat cagcttcttg aaattcaaat tcatcaaaca aaagatctcg atgggtgtct   2580

tttaacgtgc aggatgggaa agaatggtgc tgcaaatcct gtttcttggt ccgtctaatc   2640

tcttggagcc aaacgcgagc ttcgcacaaa tgtcacagaa gctgatcgtt tctcccattg   2700

tcaagactct ggtctttagc aaagtccctg agaaggtgag ggactggatc gatgagatag   2760

cgagtgactg gagattcaag aggataatcc cagctcattt cgaggctccg gtaaacgcag   2820

ggaggtcaga atttctagct gcgtttgggt ttcttgatga tcttctaggg gaaagatatg   2880

tgaaccgtcc tccttcgctc tctgttctct tcacttcgct gatgggtaaa gcagcgagct   2940

attttcctcc ggatgatatg aggactctct cttctcttga tcagttctta gtctctgttg   3000

gtgctgttaa gaagaccgtc tctggtagaa aacgaagatg acggaacaaa cccagctttc   3060

t                                                                   3061
```

<210> SEQ ID NO 16
<211> LENGTH: 3025
<212> TYPE: DNA
<213> ORGANISM: Brassica oleracea

<400> SEQUENCE: 16

```
aaaaagcagg ctaagagtgt aagcgaccca tttcacattg gatctaaaaa tcaaataatc     60

tagagtgtga caagaatcaa cgttgataga gagtgagaga gaatagtaca gagccagtcg    120

tcgaggtaga aatgtttgtc ctgagcccaa atggtatagt tgatattggg attccagaac    180

ttgttatcac ccactatcca tctcttagcg gccacctcag tcaccggagc tgccgcaaga    240

aaagccagaa ccactgccgc agccatcaac gcaagtctag ccatagatca ctctagaaag    300

aaaaagaagc tcagtgcttg atgactctta gtcttatctc tcaagaaata gcagttttat    360
```

-continued

```
gagtgagtgg ggctgtttcc aagtcaaatc agacatacaa atttctcgtt ttacggggaa    420
aagatctctc aagatccgta atttcttcaa ctaacgtttg gaatcttatt actactttaa    480
tcaacctcga tgttgacgat gacgtacacg ttaattaaag gtacgcgtta tatagttaag    540
ggagtaatta gattttaact gctggcatta ttattatttt tctctggtta ttacattatt    600
ctgttttgta gtaatatttt ctcacctttt aggcgggaat ttatttccat tttcttcttt    660
caagggttca gagattcaat tcctttatta acatacgaaa tgagtatata gtatctttta    720
aatatttaaa taattaaaat aaaaataaat tactataaca gtgatacata tcaaaatttc    780
caaaactaat gtgagtactt atattagttg tacttcttag taaaataacg agatatgtta    840
tggctcgtcg catacagcaa agcagagcat atgttcccgc aataacatgc acacgcaact    900
gatagcacgt cgtaaccatt tccgcgaacc aaccaatgga tattgtaatt cgataagacg    960
acgtcgtgtt gttgaccacg aatatttctt aaatttcctt ttatcttttg tttttgacgt   1020
catgacattg gtttatgtcc acacgatatc agtcataaaa tccacgtagg aacgactatc   1080
cattacaccc atccacgtgt tctcataaca gcttctagtt ccattagctg aacgaacaat   1140
agaaacagag catcgaactg agaaagaaga agaagaaggg aagcaagaga aatggcggca   1200
gcggccatgg ccgttcatct cccgaaacat tcatcgtttc ttacgaaacc caagcatcca   1260
tccgatcaaa actctaactt tctcggtggg tccttaaagt tcggtcgatc catgtctcta   1320
aaccggaaaa ctaaaggtcc agttatggtt tcagctgctt cgaccgtcga aggcgatcga   1380
agcaaacagt tttacataaa cttcactgga ttcccatttc ctcttggtcc tttccttaac   1440
cggcgcacca tcagaaccga ggttaggctt tctccatccc tcttgagttt tgatttgaac   1500
tcgttgagaa tcccatatgg ataatgttat gcaggcggtt aaaggaagca tatggatgtt   1560
tgaacaagaa caagctttag gtttcagcag tgtctcaacg aatataagaa tgactgtcat   1620
caaactcaaa tccggtggct tatgggttca tgcccctatt gctcccacca aagagtgtat   1680
tcaggttccc tcttttattc attatcagta tcatcctttc ttatcatttg ataaattaac   1740
caatgtctaa actctatttt gggttgtttt gcttactttt tctttggggc agcttattga   1800
ggagttggga gctccggttg agtacatcgt cctaccaacc ttcgcttacg agcacaagat   1860
cttcgtcggt cccttctcta gaaagttccc caaggctcaa gtatgggtgg cgccaagaca   1920
atggagctgg ccactgaact taccactcga gtttttcggt atctttcgcg ctaaaaccat   1980
taaagacggt gacttgtcta ccccgtgggc tgatgagatc gagcagaaag tcttaagctc   2040
tcctgaagtc ggtacgttcc ttcactttct caatcttgtt ggccctcctt agccaagcct   2100
cataaaacat tcgcttcaac cctcaccccc acccaaattt tttgaaaaaa gttacatata   2160
catagcccca aatttattaa aaaaatctat tgaaatcttt attaaattat ctacgtcccc   2220
tagaatctga gggtcggccc tgtacttatg gaataaataa tatacaggaa ttggaccgta   2280
tgtggaagta gcgttctacc ataagcgttc aagaactcta ttagtcaccg acgctgtgat   2340
cttcgtccca aagaagccgc catcgagtat cagcagcgag tctttgctgg cttctgctaa   2400
gaacggactg gctgtgaaga tacttagcaa aggcaaacaa gtacctaatg accctgtcgt   2460
tgatacccca aacacccgcc aaaaaggtca gccatcagct tcttgaaatt caaattcatc   2520
aaacaaagat ctcaatgggt gtcttttaac gtgcaggatg ggaaagaatg gtgctgcaaa   2580
tcctgtttct cggcccatct aatctcttgg agccaaacgc gagctttgcg caaatgtcac   2640
agaagctgat agtttctccc attgtcaaga ctctggtctt tagcaaagtc cctgagaagg   2700
tgagggactg gatcgatgag atagcgagtg actggaggtt caagaggata atcccagctc   2760
```

atttcgaggc tccgataaac gcggggaggt cagagtttct agctgcgttc gggtttcttg 2820
atgatcttct aggggaaaga tatgtgaacc gtcctccttc gctctctgtt ctctttactt 2880
cgctgatggg taaagctgcc agctattttc ctccggatga tatgagaact ctctcttctc 2940
ttgatcagtt cttagtctct gttggtgctg ttaagaagac cgtctctggt agaaaacgaa 3000
gatgacggaa caaacccagc tttct 3025

<210> SEQ ID NO 17
<211> LENGTH: 448
<212> TYPE: PRT
<213> ORGANISM: Brassica oleracea

<400> SEQUENCE: 17

Met Ala Ala Ala Ala Met Ala Val His Leu Pro Lys His Ser Ser Phe
1 5 10 15

Leu Pro Asn Pro Lys Leu Pro Leu Asn Gln Asn Ser Asn Phe Leu Gly
20 25 30

Val Ser Leu Lys Ile Gly Arg Pro Met Ser Val Asn Arg Lys Met Lys
35 40 45

Gly Pro Val Thr Val Ser Ala Ala Ser Thr Val Glu Gly Asp Arg Ser
50 55 60

Lys Gln Phe Tyr Ile Asn Phe Thr Gly Phe Pro Phe Pro Leu Gly Pro
65 70 75 80

Phe Leu Asn Arg Arg Thr Ile Arg Thr Glu Ala Val Lys Gly Ser Ile
85 90 95

Trp Met Phe Glu Gln Glu Gln Ala Leu Gly Phe Ser Ser Val Ser Thr
100 105 110

Asn Ile Arg Met Thr Val Ile Arg Leu Lys Ser Gly Gly Leu Trp Val
115 120 125

His Ala Pro Ile Ala Pro Thr Lys Glu Cys Ile Gln Leu Ile Glu Glu
130 135 140

Leu Gly Ala Pro Val Glu Tyr Ile Val Leu Pro Thr Phe Ala Tyr Glu
145 150 155 160

His Lys Ile Phe Val Gly Pro Phe Ser Arg Lys Phe Pro Lys Ala Gln
165 170 175

Val Trp Val Ala Pro Arg Gln Trp Ser Trp Pro Leu Asn Leu Pro Leu
180 185 190

Glu Phe Phe Gly Ile Phe Arg Ala Lys Thr Ile Lys Asp Gly Asp Leu
195 200 205

Ser Thr Pro Trp Ala Asp Glu Ile Glu Gln Lys Val Leu Ser Ser Pro
210 215 220

Glu Val Gly Ile Gly Pro Tyr Val Glu Val Ala Phe Tyr His Lys Arg
225 230 235 240

Ser Arg Thr Leu Leu Val Thr Asp Ala Val Ile Phe Val Pro Arg Lys
245 250 255

Pro Pro Ser Ser Ile Ser Ser Glu Ser Leu Leu Ala Ser Ala Lys Asn
260 265 270

Gly Leu Ala Val Lys Ile Leu Ser Lys Gly Lys Gln Val Pro Asp Asp
275 280 285

Pro Val Val Asp Thr Pro Asn Thr Arg Gln Lys Gly Trp Glu Arg Met
290 295 300

Val Leu Gln Ile Leu Phe Leu Gly Pro Ser Asn Leu Leu Glu Pro Asn
305 310 315 320

```
Ala Ser Phe Ala Gln Met Ser Gln Lys Leu Ile Val Ser Pro Ile Val
                325                 330                 335

Lys Thr Leu Val Phe Ser Lys Val Pro Glu Lys Val Arg Asp Trp Ile
            340                 345                 350

Asp Glu Ile Ala Ser Asp Trp Arg Phe Lys Arg Ile Ile Pro Ala His
        355                 360                 365

Phe Glu Ala Pro Val Asn Ala Gly Arg Ser Glu Phe Leu Ala Ala Phe
    370                 375                 380

Gly Phe Leu Asp Asp Leu Leu Gly Glu Arg Tyr Val Asn Arg Pro Pro
385                 390                 395                 400

Ser Leu Ser Val Leu Phe Thr Ser Leu Met Gly Lys Ala Ala Ser Tyr
                405                 410                 415

Phe Pro Pro Asp Asp Met Arg Thr Leu Ser Ser Leu Asp Gln Phe Leu
            420                 425                 430

Val Ser Val Gly Ala Val Lys Lys Thr Val Ser Gly Arg Lys Arg Arg
        435                 440                 445


<210> SEQ ID NO 18
<211> LENGTH: 448
<212> TYPE: PRT
<213> ORGANISM: Brassica oleracea

<400> SEQUENCE: 18

Met Ala Ala Ala Ala Met Ala Val His Leu Pro Lys His Ser Ser Phe
1               5                   10                  15

Leu Thr Lys Pro Lys His Pro Ser Asp Gln Asn Ser Asn Phe Leu Gly
            20                  25                  30

Gly Ser Leu Lys Phe Gly Arg Ser Met Ser Leu Asn Arg Lys Thr Lys
        35                  40                  45

Gly Pro Val Met Val Ser Ala Ala Ser Thr Val Glu Gly Asp Arg Ser
    50                  55                  60

Lys Gln Phe Tyr Ile Asn Phe Thr Gly Phe Pro Phe Pro Leu Gly Pro
65                  70                  75                  80

Phe Leu Asn Arg Arg Thr Ile Arg Thr Glu Ala Val Lys Gly Ser Ile
                85                  90                  95

Trp Met Phe Glu Gln Glu Gln Ala Leu Gly Phe Ser Ser Val Ser Thr
            100                 105                 110

Asn Ile Arg Met Thr Val Ile Lys Leu Lys Ser Gly Gly Leu Trp Val
        115                 120                 125

His Ala Pro Ile Ala Pro Thr Lys Glu Cys Ile Gln Leu Ile Glu Glu
    130                 135                 140

Leu Gly Ala Pro Val Glu Tyr Ile Val Leu Pro Thr Phe Ala Tyr Glu
145                 150                 155                 160

His Lys Ile Phe Val Gly Pro Phe Ser Arg Lys Phe Pro Lys Ala Gln
                165                 170                 175

Val Trp Val Ala Pro Arg Gln Trp Ser Trp Pro Leu Asn Leu Pro Leu
            180                 185                 190

Glu Phe Phe Gly Ile Phe Arg Ala Lys Thr Ile Lys Asp Gly Asp Leu
        195                 200                 205

Ser Thr Pro Trp Ala Asp Glu Ile Glu Gln Lys Val Leu Ser Ser Pro
    210                 215                 220

Glu Val Gly Ile Gly Pro Tyr Val Glu Val Ala Phe Tyr His Lys Arg
225                 230                 235                 240

Ser Arg Thr Leu Leu Val Thr Asp Ala Val Ile Phe Val Pro Lys Lys
                245                 250                 255
```

-continued

```
Pro Pro Ser Ser Ile Ser Ser Glu Ser Leu Leu Ala Ser Ala Lys Asn
            260                 265                 270

Gly Leu Ala Val Lys Ile Leu Ser Lys Gly Lys Gln Val Pro Asn Asp
        275                 280                 285

Pro Val Val Asp Thr Pro Asn Thr Arg Gln Lys Gly Trp Glu Arg Met
    290                 295                 300

Val Leu Gln Ile Leu Phe Leu Gly Pro Ser Asn Leu Leu Glu Pro Asn
305                 310                 315                 320

Ala Ser Phe Ala Gln Met Ser Gln Lys Leu Ile Val Ser Pro Ile Val
                325                 330                 335

Lys Thr Leu Val Phe Ser Lys Val Pro Glu Lys Val Arg Asp Trp Ile
            340                 345                 350

Asp Glu Ile Ala Ser Asp Trp Arg Phe Lys Arg Ile Ile Pro Ala His
        355                 360                 365

Phe Glu Ala Pro Ile Asn Ala Gly Arg Ser Glu Phe Leu Ala Ala Phe
    370                 375                 380

Gly Phe Leu Asp Asp Leu Leu Gly Glu Arg Tyr Val Asn Arg Pro Pro
385                 390                 395                 400

Ser Leu Ser Val Leu Phe Thr Ser Leu Met Gly Lys Ala Ala Ser Tyr
                405                 410                 415

Phe Pro Pro Asp Asp Met Arg Thr Leu Ser Ser Leu Asp Gln Phe Leu
            420                 425                 430

Val Ser Val Gly Ala Val Lys Lys Thr Val Ser Gly Arg Lys Arg Arg
        435                 440                 445
```

MODULATION OF SEED VIGOR

RELATED APPLICATION INFORMATION

This application is a divisional of U.S. application Ser. No. 14/378,349 (allowed), which application is a 371 filing of International Application No. PCT/EP2013/053845, filed Feb. 27, 2013, which claims the benefit of European Patent Application No. 12157514.6 filed Feb. 29, 2012, the contents of all of which are incorporated herein by reference in their entireties.

FIELD OF THE INVENTION

The present invention generally relates to a polynucleotide which enables the modulation of the seed vigour, particularly enhances the seed vigour, and more particularly enables the modification of the speed of germination. The invention also relates to a plant seed comprising the said polynucleotide. Moreover, method of producing the plant seed, method for improving the germination and vigour of plant seed, transgenic plant and the use of the polynucleotide of the invention for producing plants growing seeds with improved germination and vigour characteristics are also provided within the present invention. The plants of the present invention particularly concern *Brassica*, more particularly *Brassica oleracea.*

STATEMENT REGARDING ELECTRONIC SUBMISSION OF A SEQUENCE LISTING

A Sequence Listing in ASCII text format, submitted under 37 C.F.R. § 1.821, entitled "73577-Sequence_Listing_ST25", 56 kilobytes in size, generated Aug. 14, 2018 and filed via EFS-Web is provided in lieu of a paper copy. This Sequence Listing is incorporated herein by reference into the specification for its disclosures.

BACKGROUND OF THE INVENTION

Seed quality, as defined by the number of uniform usable plants obtainable from a seed batch, is becoming an ever more important trait in developed horticulture markets. Young plant raising is a highly technological activity in these markets and demands with respect to seed quality are therefore high. Reliable and consistently high seed quality is required for this. Also, germination under adverse conditions is an important seed quality trait. This means that one requirement for commercial success of seed varieties is consistent and robust seed quality. Currently however, seed quality of commercial varieties is not always stable and predictable.

Seed quality parameters are highly influenced by maternal environmental conditions during seed development. Given the volumes of seed needed and commercial feasibility, only limited controls of these conditions are possible. Therefore consistency of seed quality is limited by the susceptibility for maternal conditions. Research has shown that maternal environment can potentially affect all seed quality parameters, including uniformity and germination under adverse conditions. Decreasing the influence of maternal conditions would therefore lead to more consistent and robust seed quality, that provides advantages in both developed and developing markets.

Predictable and uniform seedling establishment is essential for the production of crops that are both sustainable and profitable. A key contributor to this predictability is the germination performance of seeds, which is influenced directly by seed dormancy and vigour. Dormancy per se (lack of germination in generally permissible conditions) is not considered to be a practical problem with many crop species, but low seed vigour (poor seed performance in practice) greatly influences not only the number of seedlings that emerge, but also the timing and uniformity of seedling emergence in all crops. The effects of this have a major impact upon many aspects of crop production that determine cost effectiveness and the inputs required, and there are also direct crop specific influences on marketable yield (Finch-Savage, 1995). Low seed vigour can result from seed deterioration and damage of many kinds and this has great commercial significance. However, there are also inherent differences in the initial vigour of the seed before it begins to deteriorate, but the genetic, molecular and physiological basis of this remains poorly understood.

Mutations in many genes have been identified that show phenotypes with altered seed germination performance and these have been instrumental in developing our current understanding of the control of germination (reviewed by Finch-Savage and Leubner-Metzger, 2006; Holdsworth et al., 2008a and 2008b). However, the relative impact of these genes in wild type or crop seeds is little understood and no clear candidates have been revealed that will form the basis of a discriminating test for seed vigour. An alternative source of genetic variation to laboratory induced mutations is available in natural populations and crop genotypes. Using this variation to identify QTL associated with seed vigour and then candidate genes influencing these traits may provide a route to identify practically important genes.

Both natural and crop plant variation has been exploited in quantitative genetic analyses of a range of seed vigour traits in tomato (Foolad et al., 1999), *Brassica oleracea* (Bettey et al., 2000, Finch-Savage et al., 2005) and *Arabidopsis* (Groot et al., 2000, Clerkx et al., 2004). Speed of seed germination QTLs have been identified in all three species.

The distinction between dormancy and low seed vigour in healthy non-aged seeds in terms of speed of germination, if one exists, is not understood and may have the same basis (Hilhorst and Toorop, 1997). In most situations, for example in *Arabidopsis*, physiological dormancy is not absolute, but seeds are conditionally dormant i.e. germination tends to be slow and is only possible in a limited range of environments. As dormancy is progressively lost, germination tends to speed up and becomes possible in a wider range of environments and can therefore appear like an increase in vigour.

Among the factors accounting for the establishment of seed germination and the regulation of seed dormancy, abscisic acid (ABA), a well-known plant hormone, plays an important role. ABA is in particular essential for the seed germination and seed maturation processes (for review, see Finkelstein et al. 2002) as it is responsible for the establishment of a period of seed dormancy. As for buds, it is important that the seeds do not germinate prematurely, for example, during unseasonably mild conditions prior to the onset of winter or a dry season. ABA in the seed enforces this dormancy. The dormancy is lifted only if the seed has been exposed to a prolonged cold spell and/or other appropriate environmental signal and if there is sufficient water to support germination. Besides its role in seed vigour, ABA also regulates many important aspects of plant life including the physiological responses to biotic threats and abiotic stresses like drought and dessication There is thus a long-standing need for seed with a more reliable and constant seed vigour; especially with a timely-defined and uniform speed of germination, in order to provide seeds that germinate at a more constant rate, independently of the maternal conditions and whatever the external environmental conditions are. Such increased seed vigour would be of particular interest in cases where the seed is coated with a given preparation (chemical, biological), as it is usually observed a delay in seed germination. In consequence, seeds comprising sequences which enhance seed vigour, more particularly enhance the speed and the uniformity of the seed germination would be of primary importance to counteract the effect of the coating treatment, while still applying insecticides and fungicides.

Furthermore, while in many aspects, increasing the seed vigour would be a very useful and desired trait, it appears that, in some cases, decreasing the seed vigour would be of great interest. In particular in viviparous seed, decreasing seed vigour could be beneficial. Vivipary is defined as the germination of the seed while still on the mother plant or before drying and can occur both in immature and fully mature seed. Vivipary has been observed in many different crop species including *Brassica* crops (Ruan et al. 2000). Seeds comprising sequences which are able to decrease the seed vigour would thus be capable of delaying, if not removing, the non-desired vivipary phenotype.

SUMMARY OF THE INVENTION

It is therefore to the inventors' credit, in such a state of the art, to have identified a plant from a population that contained a small introgressed region spanning SOG1 (Speed Of Germination 1), a speed of seed germination QTL identified in *B. oleracea* by Bettey et al. (2000) and particularly to have demonstrated and identified the corresponding genes that are involved in the modulation of the seed vigour, in particular involved in the regulation of the speed of germination of the seed. It is in particular demonstrated that these genes, and their corresponding sequences, can be used as enabling tools to obtain seeds (or plants that deliver seeds) that exhibit a modified seed vigour phenotype. In particular, gene sequences can be introduced into a new background in order to modulate the seed vigour. More particularly, gene sequences can be used to engineer a novel plant, whose seeds will emerge earlier, more uniformly, independently of the external environmental conditions, and regardless of the maternal conditions. Furthermore, the said gene sequences can be used as tools to modify ABA content in the seed and/or the seed response to ABA, thereby affecting seed behavior regarding to seed dormancy and seed storage proteins and lipids synthesis.

EMBODIMENTS

Accordingly, in a 1st embodiment, the present invention provides a polynucleotide, particularly an isolated polynucleotide, comprising a nucleic acid molecule selected from the group consisting of a. a nucleic acid molecule comprising a nucleotide sequence as depicted in SEQ ID NO: 15 (A12 version of BolC.VG1.a);
b. a nucleic acid molecule comprising a nucleotide sequence as depicted in SEQ ID NO: 7 (A12 version of BolC.VG2.a);
c. a nucleic acid molecule comprising a nucleotide sequence as depicted in SEQ ID NO: 16 (GD33 version of BolC.VG1.a);
d. a nucleic acid molecule comprising a nucleotide sequence as depicted in SEQ ID NO: 8 (GD33 version of BolC.VG2.a);
e. a nucleic acid molecule comprising a nucleotide sequence the complementary strand of which hybridizes to the nucleic acid molecule of any of a)-d);
f. a nucleic acid molecule comprising a nucleotide sequence that deviates from the nucleotide sequence defined in any of a)-e) by the degeneracy of the genetic code;

wherein said nucleic acid molecule as defined in any of a)-f) upon expression in a plant or plant part, leads to a modified seed vigour.

In a 2nd embodiment, the present invention provides a polynucleotide, particularly an isolated polynucleotide, according to embodiment 1, comprising a nucleic acid molecule selected from the group further consisting of a. a nucleic acid molecule comprising a nucleotide sequence as depicted in SEQ ID NO: 9 (truncated A12 allele of BolC.VG2.b);
b. a nucleic acid molecule comprising a nucleotide sequence as depicted in SEQ ID NO: 10 (truncated GD33 allele of BolC.VG2.b);
c. a nucleic acid molecule comprising a nucleotide sequence the complementary strand of which hybridizes to the nucleic acid molecule of any of a)-b);
d. a nucleic acid molecule comprising a nucleotide sequence that deviates from the nucleotide sequence defined in any of a)-c) by the degeneracy of the genetic code;

wherein said nucleic acid molecule as defined in any of a)-d) upon expression in a plant or plant part, leads to a modified seed vigour.

In a 3rd embodiment, the present invention provides a polynucleotide, particularly an isolated polynucleotide, comprising a nucleic acid molecule selected from the group consisting of:

a. nucleic acid molecule comprising a nucleotide sequence that has at least 60% sequence identity to any of the sequences as depicted in the group comprising: SEQ ID NO:7, SEQ ID NO:8, SEQ ID NO:9, SEQ ID NO:10, SEQ ID NO:15 and SEQ ID NO:16;
b. nucleic acid molecule comprising a nucleotide sequence that has at least 80% sequence identity to any of the sequences as depicted in the group comprising: SEQ ID NO:7, SEQ ID NO:8, SEQ ID NO:9, SEQ ID NO:10, SEQ ID NO:15 and SEQ ID NO:16;
c. nucleic acid molecule comprising a nucleotide sequence that has at least 90% sequence identity to any of the sequences as depicted in the group comprising: SEQ ID NO:7, SEQ ID NO:8, SEQ ID NO:9, SEQ ID NO:10, SEQ ID NO:15 and SEQ ID NO:16;
d. nucleic acid molecule comprising a nucleotide sequence that has at least 95% sequence identity to any of the sequences as depicted in the group comprising: SEQ ID NO:7, SEQ ID NO:8, SEQ ID NO:9, SEQ ID NO:10, SEQ ID NO:15 and SEQ ID NO:16;
e. nucleic acid molecule comprising a nucleotide sequence that has at least 98% sequence identity to any of the sequences as depicted in the group comprising: SEQ ID NO:7, SEQ ID NO:8, SEQ ID NO:9, SEQ ID NO:10, SEQ ID NO:15 and SEQ ID NO:16;
f. nucleic acid molecule comprising a nucleotide sequence the complementary strand of which hybridizes to the nucleic acid molecule of any of a)-e);
g. nucleic acid molecule comprising a nucleotide sequence that deviates from the nucleotide sequence defined in any of a)-f) by the degeneracy of the genetic code;

wherein said nucleic acid molecule as defined in any of a)-g) upon expression in a plant or plant part, leads to a modified seed vigour.

In a 4$^{th}$ embodiment, the present invention relates to a polynucleotide according to first, second or third embodiment, wherein the modified seed vigour phenotype is characterized by a further phenotype selected in the group comprising: modified speed of germination, modified speed of seedling emergence, modified uniformity of seed germination, modified uniformity of seedling emergence, modified percentage of seed germination, modified tolerance of the seed vis-a-vis external environmental and/or maternal conditions, modified sensitivity to ABA or modified content of ABA.

In a 5$^{th}$ embodiment, the present invention relates to a polynucleotide, particularly an isolated polynucleotide, comprising a nucleic acid molecule selected in the group comprising:

a. a nucleic acid molecule comprising a nucleotide sequence as depicted in SEQ ID NO: 16;
b. a nucleic acid molecule comprising a nucleotide sequence as depicted in SEQ ID NO: 8;
c. a nucleic acid molecule comprising a nucleotide sequence as depicted in SEQ ID NO: 10;
d. a nucleic acid molecule comprising a nucleotide sequence the complementary strand of which hybridizes to the nucleic acid molecule of any of a)-c);
e. a nucleic acid molecule comprising a nucleotide sequence that deviates from the nucleotide sequence defined in any of a)-d) by the degeneracy of the genetic code;

wherein said nucleic acid molecule as defined in any of a)-e) upon expression in a plant or plant part, leads to an increased seed vigour.

In the context of the present invention, the expression "increased seed vigour" means that the speed of germination of the seed may be modified in the sense that the seed germinates faster and is thus more vigorous. In one particular embodiment the speed of germination is increased allowing seeds to be obtained that germinates faster thanks to the presence of a polynucleotide according to the present invention in its genome as compared to a seed that does not comprise said polynucleotide. Such an increased speed of germination results in a significant earlier seedling emergence and thus provides the seeds with enhanced flexibility and better adaptation to various environments. The 2 genes that were identified were found to have a significant germination phenotype indicating these genes are regulators of germination to different extent. The allele corresponding to the polynucleotide of SEQ ID NO: 16 and SEQ ID NO: 8 (GD33 alleles of the genes) according to the present invention has been proven to correspond to phenotype of increased seed vigour and thus allow to modify the speed of germination of plant seed in which it is introgressed into towards and increased speed of germination.

In a 6$^{th}$ embodiment, the present invention relates to a polynucleotide according to embodiment 5, wherein the increased seed vigour phenotype is characterized by a further phenotype selected in the group comprising: increased speed of germination, increased speed of seedling emergence, increased uniformity of seed germination, increased uniformity of seedling emergence, increased percentage of seed germination, increased tolerance of the seed vis-a-vis external environmental and/or maternal conditions, decreased sensitivity to ABA or decreased content of ABA.

In a 7$^{th}$ embodiment, the present invention relates to a polynucleotide, particularly an isolated polynucleotide, comprising a nucleic acid molecule selected in the group comprising:

a. a nucleic acid molecule comprising a nucleotide sequence as depicted in SEQ ID NO: 15;
b. a nucleic acid molecule comprising a nucleotide sequence as depicted in SEQ ID NO: 7;
c. a nucleic acid molecule comprising a nucleotide sequence as depicted in SEQ ID NO: 9;
d. a nucleic acid molecule comprising a nucleotide sequence the complementary strand of which hybridizes to the nucleic acid molecule of any of a) to c);
e. a nucleic acid molecule comprising a nucleotide sequence that deviates from the nucleotide sequence defined in any of a)-d) by the degeneracy of the genetic code;

wherein said nucleic acid molecule as defined in any of a)-e) upon expression in a plant or plant part, leads to a decreased seed vigour.

In an 8$^{th}$ embodiment, the present invention provides an expression cassette comprising a polynucleotide of any of the preceding embodiments.

In a 9$^{th}$ embodiment, the present invention provides a vector molecule comprising the expression cassette according to the 8$^{th}$ embodiment.

In a 10$^{th}$ embodiment, the present invention relates to the use of a polynucleotide according to embodiments 1 to 3 for modifying seed vigour.

In a 11$^{th}$ embodiment, the present invention relates to a method for modifying the seed vigour comprising introgressing through crossing or by plant transformation techniques to and expressing in a plant or plant part a polynucleotide, an expression cassette or a vector molecule of any of embodiments 1 to 10.

In a 12$^{th}$ embodiment, the present invention relates to a method for producing seed with modified seed vigour comprising:

a. obtaining a first plant verified to contain the polynucleotide of any of embodiments 1 to 7;
b. crossing said first plant with a second plant verified to lack the said polynucleotide; and
c. identifying a plant seed resulting from the cross exhibiting a modified seed vigour as compared to seeds delivered by the second plant.

In a 13$^{th}$ embodiment, the present invention relates to a plant or plant part which contains within its genome an introgression comprising the polynucleotide, the expression cassette or the vector molecule of any of embodiments 1 to 9 and exhibits a modification of seed vigour as compared to a plant or plant part that does not comprise the said polynucleotide, expression cassette or vector molecule.

In a 14$^{th}$ embodiment, the present invention relates to a plant or plant part which contains within its genome an introgression comprising a polynucleotide according to embodiment 5 and exhibits an increased seed vigour as compared to a seed delivered by a plant or plant part that does not comprise the said polynucleotide.

In a 15$^{th}$ embodiment, the present invention relates to a plant or plant part which contains within its genome an introgression comprising a polynucleotide according to embodiment 7 and exhibits a decreased seed vigour as compared to a seed delivered by a plant or plant part that does not comprise the said polynucleotide.

In a 16$^{th}$ embodiment, the invention provides a method for selecting plant or plant part with modified seed vigour, comprising the detection in the plant or plant part to be tested of the presence or absence of a polynucleotide according to any of embodiments 1 to 7.

In a 17$^{th}$ embodiment, the invention provides a method for selecting plant or plant parts with modified seed vigour, comprising contacting candidate plant or plant part with a selection tool selected from the group comprising the polynucleotides of any of embodiments 1 to 7.

In a $18^{th}$ embodiment, the present invention relates to plant or plant part according to any of the preceding claims that are cultivated plant or cultivated plant part and are selected in the group comprising *Brassica oleracea, Brassica napus, Brassica rapa, Brassica campestris, Brassica juncea, Brassica nigra, Brassica pekinensis, Brassica chinensis, Brassica rosularis, Eruca vesicaria, Eruca sativa, Raphanus sativus, Lepidium sativum, Nasturtium officinale, Wasabia japonica.*

In a $19^{th}$ embodiment, the invention provides a non biological method for obtaining plant or plant part with modified seed vigour, comprising introducing a polynucleotide according to any of embodiments 1 to 7 into the genome of said plant or plant part.

In an embodiment 20, the invention relates to the method according to embodiment No 16 comprising (a) obtaining a first plant verified to contain the polynucleotide of any of embodiments 1 to 7; (b) crossing said first plant with a second plant verified to lack the said polynucleotide; and (c) identifying a plant resulting from the cross exhibiting modified seed vigour, and containing the said polynucleotide.

In an embodiment 21, the invention relates to the method according to embodiment 20, wherein presence of the polynucleotide is verified by use of a molecular marker, particularly by a molecular marker physically located in a position that is within or outside the genetic locus containing the polynucleotide.

In an embodiment 22, the invention relates to the method according to embodiment 20, wherein presence of the polynucleotide is verified by use of at least two molecular markers, particularly by at least two molecular markers physically located in a position that is flanking the genetic locus containing the polynucleotide.

In an embodiment 23, the invention relates to a seed comprising a polynucleotide according to embodiments 1 to 7, wherein the said seed is coated with any type of coating.

In an embodiment 24, the invention relates to a plant or plant part according to embodiments 13 to 18, wherein the plant is a hybrid plant.

In an embodiment 25, the invention relates to a plant or plant part according to embodiment 24 obtainable from seed deposited at NCIMB under deposit number NCIMB 41951, or progeny thereof.

DETAILED DESCRIPTION OF THE INVENTION

Figure 1:
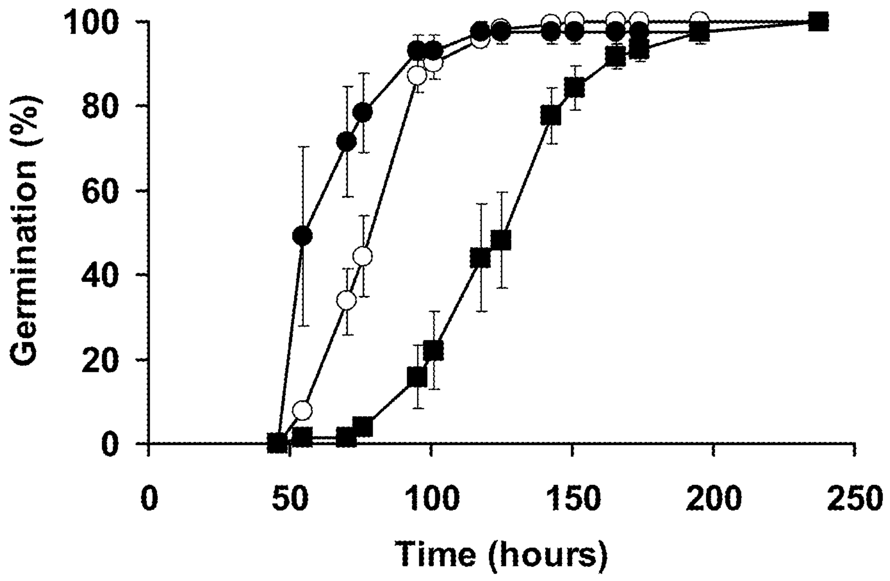
FIG. 1 is a graphic representation of the cumulative germination curves of seeds from the substitution line SL101 (○) and parent lines (A12DHd (■) and GDDH33 (●)) at 15° C. on water. Vertical lines are standard errors.

The polynucleotides sequences according to the previous embodiment have been identified in and isolated from a *Brassica oleracea* plant with different seed vigour phenotypes. Alleles with the polynucleotide sequences according to the present invention were introgressed into a plant with different seed quality and different seed vigour. Thanks to the introgression of any of the polynucleotide sequence according to the present invention, seed vigour is significantly modified and consequently plant or plant part quality, particularly seed quality of the plant was significantly modified, particularly seed vigour, as highlighted by the speed of germination. In one embodiment the seed was able to germinate better and quicker, particularly in cold conditions, showing more robust seed quality. The introgression of a polynucleotide sequence according to embodiment 5 allows to obtain seed quality of the plant less susceptible to seed production environment. This means that the introgression of the polynucleotide sequences according to the present invention enables delivery of consistent seed quality from conventional seed production.

Introduction of the polynucleotide sequences according to the present invention in commercial cultivated plant, particularly cultivated *Brassica* plants, more particularly cultivated *Brassica oleracea* plants, will ensure more reliable production of seed with sufficient seed quality. This will significantly increase operational flexibility.

Hybrid seeds that comprise any of the polynucleotide sequences according to the present invention exhibit a more uniform stand establishment, especially under adverse conditions. This will definitively add value to the commercial seed product.

Seed Deposit Details

The following seed samples were deposited with NCIMB, Ferguson Building, Craibstone Estate, Bucksburn, Aberdeen AB21 9YA, Scotland, UK, on Apr. 4, 2012 under the provisions of the Budapest Treaty in the name of Syngenta Participations AG:

NCIMB 41950 *Brassica oleracea* A12

NCIMB 41951 *Brassica oleracea* SL101

Definitions

The technical terms and expressions used within the scope of this application are generally to be given the meaning commonly applied to them in the pertinent art of genetic engineering in plants, plant breeding and cultivation if not otherwise indicated herein below.

As used in this specification and the appended claims, the singular forms “a”, “an”, and “the” include plural referents unless the context clearly dictates otherwise. Thus, for example, reference to “a plant” includes one or more plants, and reference to “a cell” includes mixtures of cells, tissues, and the like.

A “cultivated plant”, particularly “cultivated *Brassica* plant”, more particularly “cultivated *Brassica oleracea* plant” is understood within the scope of the invention to refer to a plant that is no longer in the natural state but has been developed by human care and for human use and/or growing purposes and/or consumption. "Cultivated plant", particularly "cultivated *Brassica* plant", more particularly "cultivated *Brassica oleracea* plant" are further understood to exclude those wild-type species which comprise the trait being subject of this invention as a natural trait and/or part of their natural genetics.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

A "truncated" allele of a gene is meant within the present invention to represent an allele of a gene that has lost single or multiple partial nucleotide sequences when compared with its full-length gene allele counterpart.

An allele associated with a qualitative trait may comprise alternative or variant forms of various genetic units including those that are identical or associated with a single gene or multiple genes or their products or even a gene disrupting or controlled by a genetic factor contributing to the phenotype represented by the locus.

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof, which all are known techniques to the person skilled in the art.

"Backcrossing" is understood within the scope of the invention to refer to a process in which a hybrid progeny is repeatedly backcrossed back to one of the parents. Different recurrent parents may be used in subsequent backcrosses. Recombinant lines can be produced by selfing the offspring resulting from backcrossing.

"Locus" is understood within the scope of the invention to refer to a region on a chromosome, which comprises a gene or any other genetic element or factor contributing to a trait.

"Introgression" (or introgressed) is understood within the scope of the present invention to refer to a movement of gene or segment(s) of nucleic acid from a species into the gene pool of another species, or from a line into the gene pool of another line within the same species. Introgression may be achieved by sexual crossing, sexual hybridization or by genetic transformation.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

For the purpose of the present invention, the term "segregation" or "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the phrase "genetic marker" or "marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" or "marker" can also refer to a polynucleotide sequence complementary to a genomic sequence, such as a sequence of a nucleic acid used as probes.

A "genetic marker" or "marker" can be physically located in a position on a chromosome that is within or outside of to the genetic locus with which it is associated (i.e., is intragenic or extragenic, respectively). Stated another way, whereas "genetic markers" or "markers" are typically employed when the location on a chromosome of the gene or of a functional mutation, e.g. within a control element outside of a gene, that corresponds to the locus of interest has not been identified and there is a non-zero rate of recombination between the "genetic marker" or "marker" and the locus of interest, the presently disclosed subject matter can also employ "genetic markers" or "markers" that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more "genetic markers" or "markers" comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest. Thus, in some embodiments a genotype comprises a summary of one or more alleles present within an individual at one or more genetic loci of a quantitative trait. In some embodiments, a genotype is expressed in terms of a haplotype.

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

For example, "polynucleotide sequence" as used herein refers to all forms of naturally occurring or recombinantly generated types of nucleic acids and/or nucleotide sequences as well as to chemically synthesized nucleic acids/nucleotide sequences. This term also encompasses nucleic acid analogs and nucleic acid derivatives such as, e.g., locked DNA, RNA, cDNA, PNA, oligonucleotide thiophosphates and substituted ribo-oligonucleotides. Furthermore, the term "polynucleotide sequence" also refers to any molecule that comprises nucleotides or nucleotide analogs. The phrase "nucleic acid" or "polynucleotide" refers to any physical string of monomer units that can be corresponded to a string of nucleotides, including a polymer of nucleotides (e.g., a typical DNA, cDNA or RNA polymer), optionally containing synthetic, non-natural or altered nucleotide bases capable of incorporation into DNA or RNA polymers, modified oligonucleotides (e.g., oligonucleotides comprising bases that are not typical to biological RNA or DNA, such as 2'-O-methylated oligonucleotides), and the like. The term "polynucleotide" is understood herein to refer to polymeric molecule of high molecular weight which can be single-stranded or double-stranded, multi-stranded, or combinations thereof, composed of monomers (nucleotides) containing a sugar, phosphate and a base which is either a purine or pyrimidine. Unless otherwise indicated, a particular nucleic acid sequence of the presently disclosed subject matter optionally comprises or encodes complementary sequences, in addition to any sequence explicitly indicated.

Preferably, the term "polynucleotide sequence" refers to a nucleic acid molecule, i.e. deoxyribonucleic acid (DNA) and/or ribonucleic acid (RNA). The "polynucleotide sequence" in the context of the present invention may be made by synthetic chemical methodology known to one of ordinary skill in the art, or by the use of recombinant technology, or may be isolated from natural sources, or by a combination thereof. The DNA and RNA may optionally comprise unnatural nucleotides and may be single or double stranded. "Polynucleotide sequence" also refers to sense and anti-sense DNA and RNA, that is, a polynucleotide sequence which is complementary to a specific sequence of nucleotides in DNA and/or RNA. Furthermore, the term "polynucleotide sequence" may refer to DNA or RNA or hybrids thereof or any modification thereof that is known in the state of the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mRNA, antisense RNA, ribozymal or a DNA encoding such RNAs or chimeroplasts (Gamper, Nucleic Acids Research, 2000, 28, 4332-4339). Said polynucleotide sequence may be in the form of a plasmid or of viral DNA or RNA. "Polynucleotide sequence" may also refer to (an) oligonucleotide(s), wherein any of the state of the art modifications such as phosphothioates or peptide nucleic acids (PNA) are included.

A "polynucleotide fragment" is a fraction of a given polynucleotide molecule or of a "polynucleotide sequence". In higher plants, deoxyribonucleic acid (DNA) is the genetic material while ribonucleic acid (RNA) is involved in the transfer of information contained within DNA into proteins. A "genome" is the entire body of genetic material contained in each cell of an organism.

Unless otherwise indicated, a particular nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al., 1994). The term polynucleotide is used interchangeably with nucleic acid, nucleotide sequence and may include genes, cDNAs, and mRNAs encoded by a gene, etc.

The polynucleotide of the invention is understood to be provided in isolated form. The term "isolated" means that the polynucleotide disclosed and claimed herein is not a polynucleotide as it occurs in its natural context, if it indeed has a naturally occurring counterpart. Accordingly, the other compounds of the invention described further below are understood to be isolated. If claimed in the context of a plant genome, the polynucleotide of the invention is distinguished over naturally occurring counterparts by the insertion side in the genome and the flanking sequences at the insertion side.

As used herein, the term "gene" refers to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program. A "marker gene" encodes a selectable or screenable trait.

Suitable markers used within the invention may, for example, be selected from the group consisting of single nucleotide polymorphism (SNP) markers, indel (i.e., insertions/deletions) markers, simple sequence repeat (SSR) markers, restriction fragment length polymorphism (RFLP) markers, random amplified polymorphic DNA (RAPD) markers, cleaved amplified polymorphic sequence (CAPS) markers, Diversity Arrays Technology (DArT) markers, and amplified fragment length polymorphisms (AFLPs) markers.

For example, RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis. SNPs use PCR extension assays that efficiently pick up point mutations. The procedure requires little DNA per sample. One or two of the above methods may be used in a typical marker-based selection breeding program.

The most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form. As disclosed herein, such primers may be used for fine mapping, map-based cloning and for expression analysis.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Probe" as used herein refers to a group of atoms or molecules which is capable of recognising and binding to a specific target molecule or cellular structure and thus allowing detection of the target molecule or structure. Particularly, "probe" refers to a labelled DNA or RNA sequence which can be used to detect the presence of and to quantify a complementary sequence by molecular hybridization.

Such polynucleotide sequences being capable of hybridizing may be identified and isolated by using the polynucleotide sequences described herein or parts or reverse complements thereof, for instance by hybridization according to standard methods (see for instance Sambrook and Russell (2001), Molecular Cloning: A Laboratory Manual, CSH Press, Cold Spring Harbor, N.Y., USA). Nucleotide sequences comprising the same or substantially the same nucleotide sequences as indicated in the listed SEQ ID NO 7, 15 or 16, or parts/fragments thereof, can, for instance, be used as hybridization probes. The fragments used as hybridization probes can also be synthetic fragments which are prepared by usual synthesis techniques, the sequence of which is substantially identical with that of a nucleotide sequence according to the invention.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, this term is used herein in the context of a nucleotide sequence which has a homology, that is to say a sequence identity, of at least 50%, 55%, 60%, preferably of at least 70%, 75% more preferably of at least 80%, 85%, 86%, 87%, 88%, 89%, 90%, 91%, 92%, 93%, 94, 95%, 96%, 97%, 98%, and even most preferably of at least 99% to another, preferably entire, nucleotide sequence.

If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestf it or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The thermal melting point is the temperature (under defined ionic strength and pH) at which 50% of the target sequence hybridizes to a perfectly matched probe. Very stringent conditions are selected to be equal to the melting temperature (T.sub.m) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant part" as used herein refers to structural and/or functional sub-units of a plant including, but not limited to, plant cells, plant tissues, plant material, plant organs, harvestable plant parts, etc . . . , as defined herein below.

A "harvestable plant part" is a part of a plant refers to those parts of the plant that are harvested at any suitable time and may be further processed for industrial use or consumption including flowers, fruits, leafs, seeds, fibres, etc.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" or "plant material obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "population" means a genetically heterogeneous collection of plants sharing a common genetic derivation.

As used herein, the term "variety" or "cultivar" means a group of similar plants that by structural features and performance can be identified from other varieties within the same species.

As used herein, the term "plant transformation techniques" relates to the introduction of a transgene, conferring a specific trait, into the host plant. The transgene is incorporated into the host plant genome and stably inherited through future generations. The correct regulatory sequences are added to the gene of interest i.e. promoters and terminators, then the DNA is transferred to the plant cell culture using an appropriate vector. In some embodiments, the gene is attached to a selectable marker which allows selection for the presence of the transgene as described herein above. Once the plant tissue has been transformed, the cells containing the transgene are selected and regeneration back into whole plants is carried out.

Plant transformation can be carried out in a number of different ways for generating plant hosts with delegated functions required making plant host competent for expression of the sequence of interest, depending on the species of plant in question. For example, *Agrobacterium* mediated transformation may be used to transform plants according to the invention. Within this transformation method, plant or plant tissue (e.g. leaves) is cut into small pieces, e.g. 10×10 mm, and soaked for 10 minutes in a fluid containing suspended *Agrobacterium* containing a Ti-plasmid vector carried by *Agrobacterium* (U.S. Pat. Nos. 5,591,616; 4,940,838; 5,464,763). Placed on selectable rooting and shooting media, the plants will regrow.

Non-*Agrobacterium* techniques involve the uptake of exogenous genetic material directly by protoplasts or cells. These techniques include, but are not limited to, PEG or electroporation mediated uptake, particle bombardment-mediated delivery and microinjection. Examples of these techniques are described in Paszkowski et al., EMBO J 3, 2717-2722 (1984), Potrykus et al., Mol. Gen. Genet. 199, 169-177 (1985), Reich et al., Biotechnology 4:1001-1004 (1986), and Klein et al., Nature 327, 70-73 (1987). In each case, the transformed cells are regenerated to whole plants using standard techniques. For example, within particle bombardment particles of gold or tungsten are coated with DNA and then shot into young plant cells or plant embryos (U.S. Pat. No. 5,100,792; EP 00444882B1; EP 00434616B1). Some genetic material will stay in the cells and transform them. This method may also be used to transform plant plastids. Further, electroporation technique may be used to transform plants according to the invention. During electroporation, transient holes are prepared in cell membranes using electric shock allowing DNA to enter the cell. Another transformation technique within the invention may be viral transformation (transduction). Here, the desired genetic material is packed into a suitable plant virus and allow this modified virus to infect the plant. If the genetic material is DNA, it can recombine with the chromosomes to produce transformed cells. However, genomes of most plant viruses consist of single stranded RNA which replicates in the cytoplasm of infected cell.

The transformation or genetically engineering of the plant or plant cell with a nucleotide sequence or the vector according to the invention can be carried out by standard methods, as for instance described in Sambrook and Russell (2001), Molecular Cloning: A Laboratory Manual, CSH Press, Cold Spring Harbor, N.Y., USA. Moreover, the transgenic plant cell of the present invention is cultured in nutrient media meeting the requirements of the particular cell used, in particular in respect of the pH value, temperature, salt concentration, aeration, antibiotics, vitamins, trace elements etc.

The term "vector" or "vector molecule", as used herein, may comprise an expression cassette which may comprise expression control sequences operably linked to said polynucleotide. The vector(s) may be in the form of a plasmid, and can be used alone or in combination with other plasmids, to provide transformed plants, using transformation methods as described below to incorporate transgenes into the genetic material of the plant(s). Further vectors may comprise cosmids, viruses, bacteriophages and other vectors commonly used in genetic engineering.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The term "expression cassette", as used herein, may be made up of one or more nucleotide sequences of the present invention in operable linkage with regulatory nucleotide sequences controlling their expression. As known in the art, an expression cassette may consist of a promoter sequence (promoter), an open reading frame or a functional part thereof, a 3' untranslated region and a terminator sequence (terminator). The cassette may be part of a vector molecule as described herein above. Different expression cassettes can be transformed into plant or plant cells as long as the correct regulatory sequences are used. As used herein, the term "promoter" refers to a nucleotide sequence, usually upstream (5') to its coding sequence, which controls the expression of the coding sequence by providing the recognition for RNA polymerase and other factors required for proper transcription. A "promoter" includes a minimal promoter that is a short DNA sequence comprised of a TATA box and other sequences that serve to specify the site of transcription initiation, to which regulatory elements are added for control of expression. Further, a "promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters". In the presence of a suitable transcription factor, the minimal promoter functions to permit transcription. A "minimal or core promoter" thus consists only of all basal elements needed for transcription initiation, e.g. a TATA box and/or an initiator.

According to the invention, the term "promoter" is a regulatory region of nucleic acid (e.g. DNA) driving the transcription of a gene. Promoters are typically located near the genes they regulate, on the same strand and upstream (towards the 5' region of the sense strand). Several types of promoters are well known in the transformation arts, as are other regulatory elements that can be used alone or in combination with other promoters. A "plant promoter" is a promoter capable of initiating transcription in plant cells. Examples of promoters under developmental control include "Tissue-specific promoter" relating to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

A "cell type"-specific promoter or also called "inducible promoter" primarily drives expression in certain cell types in one or more organs, for example, vascular cells in roots or leaves by an external stimulus, such as a chemical, light, hormone, stress, or a pathogen. "Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of ≥1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysome-inducible systems.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

In the above context, the term "terminator" relates to a regulatory region of a DNA sequence that marks the end of gene on genomic DNA for transcription and, thus, initiates the termination of transcription of the respective gene.

"Expression", as used herein, refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Overexpression" relates to the level of expression in transgenic cells or organisms that exceeds levels of expression in normal or untransformed (non transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English et al., 1996). Gene silencing includes virus-induced gene silencing (Ruiz et al., 1998).

As used herein, the term "BAC(s)" stands for bacterial artificial chromosome and defines a DNA construct, based on a functional fertility plasmid used for transforming and cloning in bacteria, such as *E. coli*. BACs may be used to sequence the genome of organisms such as plants. A short piece of the organism's DNA is amplified as an insert in BACs, and then sequenced. Finally, the sequenced parts are rearranged in silico, resulting in the genomic sequence of the organism.

As used herein, "increased seed vigour" refers to the ability of a seed to germinate rapidly, in a uniform manner, and to achieve a high percentage of germination; to produce seedlings that emerge rapidly from the soil and have a high percentage of emergence; to produce seedlings that grow rapidly and demonstrate superior tolerance to various stresses including but not limited to cold. Seed vigour is the quantification of any of the above-mentioned parameters and any combination of these.

"Seed germination" is defined as emergence of the radicle from the seed coat.

"Speed of germination" hereinafter refers to the average time observed between seed imbibition and emergence of the radicle from the seed coat.

Along the application, speed of germination can eventually be measured by calculating the time period which is needed to observe 50% of seed germination (results expressed as a T50 measurement).

"Increased speed of germination" is to be understood as a significant observable difference between the germination of the seed comprising a polynucleotide according to embodiment 5 versus a seed that does not comprise one of the said polynucleotides. Typically, an increased speed of germination means that the seed comprising a polynucleotide according to embodiment 5 germinates earlier than a seed that does not comprise SEQ ID NO 8, SEQ ID NO: 10 or SEQ ID NO: 16.

"Modified speed of germination" is to be understood as a significant observable difference between the germination of the seed comprising a polynucleotide according to embodiments 1 to 7 versus a seed that does not comprise one of the said polynucleotides. Typically, a modified speed of germination means that the seed comprising a polynucleotide according to embodiments 1 to 7 germinates differently than a seed that does not comprise SEQ ID NO 7, 8, 9, 10, 15 or 16.

As used herein, uniformity of seed germination can be expressed as the time between 10% germination and 90% germination. The shorter this period of time is, the better the uniformity of seed germination is.

"Adverse external environmental conditions" are conditions which inhibit or postpone the germination of the seed or the emergence of the seedling. In the context of the present invention, cold is one factor, among others, that can be considered as being adverse to normal germination conditions.

"Emergence (of a seedling)" is meant to refer to growth of the plant that is observable.

"Increased seedling emergence" is to be understood as a significant observable difference between the emergence of a seedling from a seed comprising a polynucleotide according to embodiment 5 versus a seed that does not comprise SEQ ID NO 8, 10 or 16.

The invention will be further apparent from the following non-limiting examples in conjunction with the associated sequence listings as described below:

SEQ ID NO 15: Polynucleotide sequence corresponding to the A12DHd allele of BolC.VG1.a gene (*Brassica oleracea* ortholog of At3g01060 gene).

SEQ ID NO 7: Polynucleotide sequence corresponding to the A12DHd allele of BolC.VG2.a gene (*Brassica oleracea* ortholog of At3g01150 gene).

SEQ ID NO 16: Polynucleotide sequence corresponding to the GD33DHd allele of BolC.VG1.a gene (*Brassica oleracea* ortholog of At3g01060 gene).

SEQ ID NO 8: Polynucleotide sequence corresponding to the GD33DHd allele of BolC.VG2.a gene (*Brassica oleracea* ortholog of At3g01150 gene).

SEQ ID NO 9: Polynucleotide sequence corresponding to the truncated A12DHd allele of BolC.VG2.b gene (*Brassica oleracea* ortholog of At3g01150 gene).

SEQ ID NO 10: Polynucleotide sequence corresponding to the truncated GD33DHd allele of BolC.VG2.b gene (*Brassica oleracea* ortholog of At3g01150 gene).

Example 1

Material and Methods

Seed Production and Comparison of Lines

Seed samples were obtained from Birmingham University, UK, for a range of *Brassica oleracea* chromosome substitution lines derived from the doubled haploid parent lines A12DHd (var. *alboglabra*) and GDDH33 (var. *italica*; Rae et al., 1999). Bulk seeds were then produced and collected from 10 individual replicate plants of the substitution lines and the GDDH33 parent and 20 plants of the recurrent A12DHd parent as substitution lines are compared to the latter in germination experiments. Plants were laid out in a randomized block with 10 replicates in a glasshouse at 16-18° C. during the 16 h day and at 10-15° C. at night as described by Bettey et al. (2000). Supplementary lighting (400 W high pressure sodium lamps; Osram Ltd, St Helens, UK) was supplied when light intensity fell below 300 w $m^2$ during the 16 h day. Plants were self-pollinated by enclosing the inflorescences in perforated polyethylene bags containing blowflies before the flowers opened. The seedpods were allowed to dry completely on the plant within the enclosing bags before harvest. The seeds were cleaned, equilibrated at 15% rh and 15° C., and then stored at −20° C. before germination experiments were carried out. Cumulative germination on moist filter paper was recorded at 15° C. on 4 replicates of 15 seeds collected from each of the 10 replicate plants (or 20, A12DHd) described above. Previous work had shown this to be sufficient seeds (Bettey et al., 2000). Frequent counts were made to allow an accurate calculation of the time to 50% germination from these measurements. Percentage germination was high in all seed lots.

In later experiments, F1 seeds from reciprocal backcrosses were produced in the same manner as described above. Bud pollination was performed to make the cross resulting in the F1. Seeds from the parent lines were produced at the same time for comparison to minimize the influence of environmental differences during seed production. In addition, on a number of occasions at different times of the year seeds were produced from replicate plants of both the parent A12DHd and substitution line SL101 in glasshouses as described above. Although glasshouse heating, venting and lighting settings remained the same as those described above ambient temperature differed and was recorded.

Germination Assays

Three biological replicates of 50 seeds from substitution and parent *Brassica oleracea* lines or 3 to 15 biological replicates of 50 seeds from *Arabidopsis* wild type and mutant lines were placed to germinate on 2 layers of filter paper (Whatman International Ltd., UK) kept moist throughout treatment with water.

In all germination experiments, seeds on filter paper were held in clear polystyrene boxes laid out in randomized blocks and kept in the dark. No evidence of fungal infection was observed and so seeds were not sterilized to avoid influencing their germination. Germination (radicle emergence) was recorded at intervals to construct cumulative germination curves.

Field Emergence

As part of a larger unpublished comparison of seedling emergence from *B. oleracea* genotypes, 100 seeds of the parent lines GDDH33, A12DHd and substitution line SL101 were sown on 31 May, in 4 replicate 1 m rows arranged in a randomized block. Seeds were sown by hand in a 15 mm deep furrow, covered with sieved soil (sieve hole size <4 mm) and the surface rolled once with a Stanhay seed drill press wheel. The soil was a sandy loam and irrigation was applied to maintain soil moisture throughout seed germination and seedling emergence. The latter was recorded at regular intervals until no more seedlings emerged.

Hormone Analysis

Samples of seeds from substitution and parent lines were taken as non-imbibed dry seeds and seeds imbibed for 24 and 48 hours at 15° C. on moist filter paper. Each sample contained 1 g of dry seed measured before imbibition. The samples were placed immediately in liquid nitrogen, freeze dried and then placed in a domestic freezer at −20° C. until extraction. The samples were in 10 ml of cold (4° C.) 80% methanol (containing 20 mg I-I of BHT), then 500 ng ABA and 100 ng each of GA standards were added. The samples were stirred overnight in a cold cabinet and then centrifuged.

The supernatant was decanted and the pellet re-suspended in a further 10 ml of 80% methanol. The samples were stirred for 4 h, centrifuged and the supernatants combined. The supernatants were evaporated to aqueous (c. 3-4 ml) and 10 ml of 0.5 M pH 8.2 phosphate buffer was added, samples were partitioned with 2×15 ml of dichloromethane, and the dichloromethane discarded. The aqueous fraction was adjusted to pH 3 with 1 M phosphoric acid partitioned with 3×15 ml of ethylacetate.

The combined ethylacetate fractions were washed with 2×3.5 ml pH 3.0 water and evaporated to dryness, re-dissolved in 5 ml water and the pH adjusted to 8. The solution was then loaded onto QMA cartridges which were subsequently washed with 5 ml of 15% methanol pH 8.0. GAs and ABA were eluted from the QMA cartridges directly onto C18 21 cartridges with 0.2 M formic acid in 5% methanol. C18 cartridges were then washed with 5 ml of 20% methanol and samples recovered in 5 ml of 80% methanol and evaporated to dryness. Samples were then dissolved in methanol and methylated with excess ethereal diazomethane. Following evaporation to dryness samples were re-dissolved in dry ethylacetate and passed through amino cartridges. The resulting samples were analyzed directly for ABA content by GC-MS, then evaporated to dryness and re-dissolved in BSTFA prior to analysis for GA content by GC-MS.

Marker Analysis

Primer pairs were designed to 30 *Arabidopsis* gene models that were spread at intervals across the SOG1 region using Primer 3 software (on the World Wide Web at primer3plus.com) and gene data from Tair (on the World Wide Web at arabidpsis.org/) to give PCR products from 200 to 700 bp. The PCR mix used was standard but a touch-down program was used. This consisted of cycling parameters as follows: 94° C. for 5 mins; then annealing at 65° C. to 55° C. for 10 cycles dropping a degree each cycle with 30 s extension at 72° C. and 30 s denaturation at 94° C. over the 10 cycles; followed by 30 cycles of 94° C. 30 s, 55° C. 30 s, 72° C. 45 s; and a final extension at 72° C. for 15 min. Primer sequences for the gene models that gave polymorphic results were selected as markers (Table 1).

Data Analysis

All analyses were performed using the statistical package Genstat 5 (Payne et al. 1993), and where appropriate data were subjected to analyses of variance.

Results

QTL for Speed of Germination (SOG1) on Linkage Group C1 Confirmed and Fine-Mapped Analysis of variance of germination data comparing substitution and parent lines showed that the GDDH33 parent germinated significantly ($P<0.001$) faster than the A12DHd parent confirming that the positive speed of germination alleles are provided by GDDH33, as shown by Bettey et al. (2000) (FIG. 1). There were 4 substitution lines which spanned the SOG1 QTL (SL101, SL111, SL118, SL119) and all of these had significantly ($P<0.005$) faster germination than the A12DHd parent. The substitution line SL101 had the smallest introgressed region (1-9 cM; Rae et al., 1999) that enhanced speed of germination compared to A12DHd and accounted for much of the difference in speed of germination between the parent lines (FIG. 1) and was therefore selected for further study of SOG1.

The SOG1 Fast Germinating Phenotype is not Influenced by the Maternal Genotype

Figure 2:
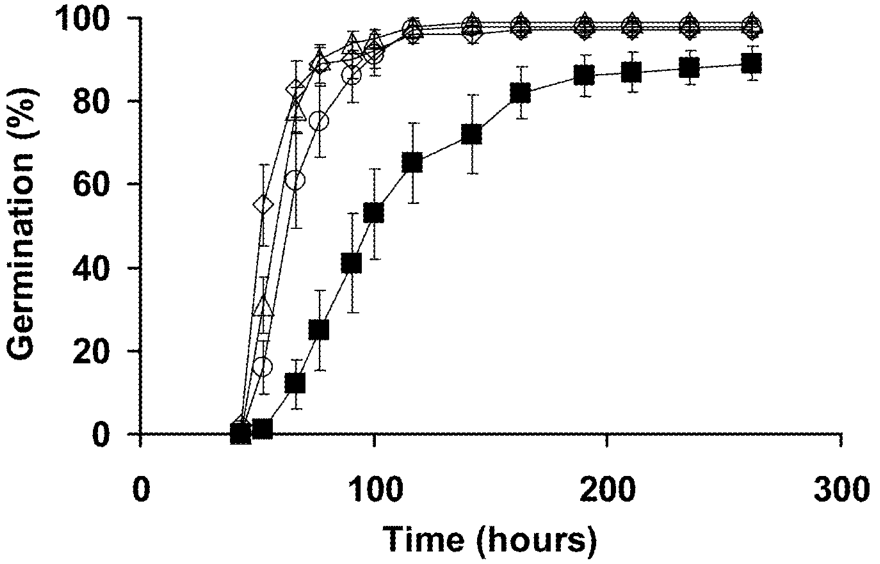
FIG. 2 is a graphic representation of the cumulative germination curves of SL101 (◇) and the recurrent A12DHd (■) parent and reciprocal $F_1$ backcross lines (A12DHd×SL101 (Δ) and SL101×A12DHd (○). Vertical lines are standard errors.

Speed of germination is determined by the embryo, but can also be significantly influenced by the tissues that surround it which are maternal in origin. Reciprocal backcrosses between SL101 and A12DHd and between GDDH33 and A12DHd were carried out to determine the maternal and zygotic genetic components at the SOG1 locus. Germination was recorded from the F1 seeds of each cross and from seeds of the selfed parent lines produced at the same time. There was no significant difference in the speed of germination of SL101 and the F1 from the reciprocal backcrosses with A12DHd (SL101 as mother plant and pollen from A12DHd and vice versa), but germination of seeds from all three were significantly ($P<0.01$) faster than that from seeds of A12DHd (FIG. 2). This shows the faster germinating GDDH33 allele to be dominant with no genetic maternal influence on inheritance of the trait confirming that it is embryo based.

Figure 3:
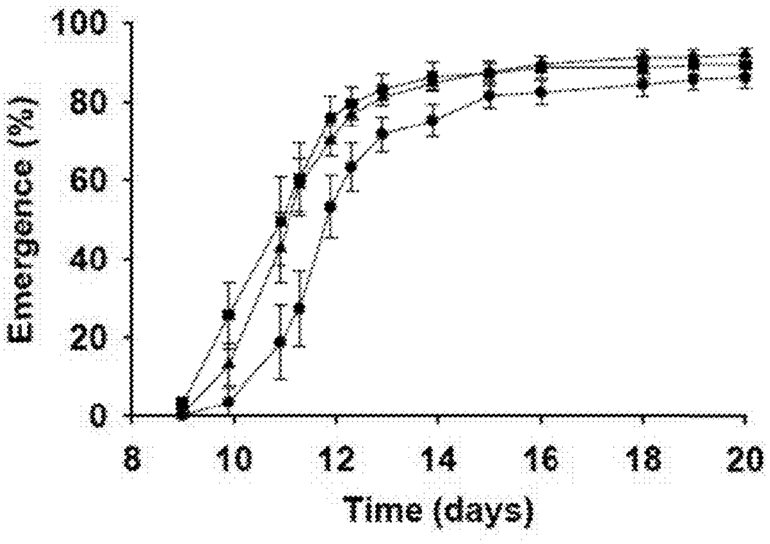
FIG. 3 is a graphic representation of the cumulative seedling emergence in the field from seeds of the substitution line SL101 (▲) and parental lines A12DHd (●) and GDD33H (■).

Differences in Speed of Germination Lead to Differences in the Timing of Seedling Emergence in the Field The data above show that the speed of germination of GDDH33 and SL101 seeds was significantly greater than that of A12DHd under constant temperature conditions. In the field this resulted in significantly earlier seedling emergence from GDDH33 and SL101 than from A12DHd (FIG. 3).

Endogenous ABA Concentration Differs Between Genotypes at Maturity

Figure 4:
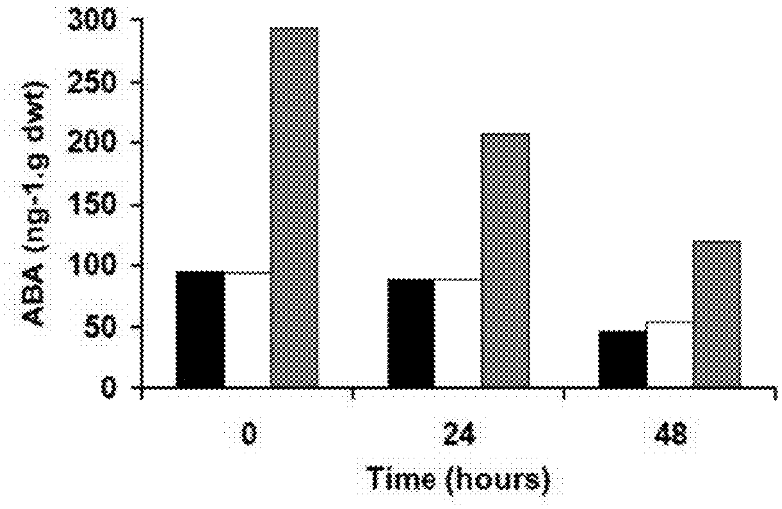
FIG. 4 is a diagram illustrating endogenous concentrations of ABA during germination in seeds of the substitution line SL101 (white column) and parent lines, GDDH33 (black column) and A12DHd (grey column).

The endogenous concentration of ABA in dry and imbibing seeds of the three genotypes was measured using GCMS. There was no significant difference in the endogenous concentration of ABA in the dry seed of SL101 and GD33 or during imbibition to 48 hours just prior to radicle emergence. ABA concentration in these two seed lots remained the same over the first 24 hours and then declined to half that by 48 hours. In contrast, the endogenous concentration of ABA in seeds of A12DHd was initially three fold higher than that in SL101 and GDDH33 and then declined progressively over the 48 hour period of imbibition, but remained significantly above that of the other two seed lots (FIG. 4). Interestingly, if ABA continues to decline at the same speed in A12DHd it would reach the same level after 72 hours, the point of germination, as seen in the other two lines immediately before their germination.

The results for GDDH33, SL101 and the A12DHD lines presented here show that a clear genetically determined relationship between higher endogenous ABA content, and lower speed of germination and vice versa.

A Quantitative Genetic Analysis of the Speed of Germination Trait in *Brassica oleracea* has been Carried Out.

By fine mapping the QTL with the previously described substitution line SL101, we finally identified two genes underlying the QTL (Speed Of Germination (SOG1)). This line SL101 has a short introgression at the telomeric end of C1 from the fast germinating parent (GD33, Broccoli) in the background of the slow germinating parent (A12, Kale) in *Brassica oleracea*. By the way of using markers across this introgressed region of SL101, 30 recombinations along this area were identified within 1,300 lines, thanks to a BAC tilling path strategy. This strategy allows gathering the lines into 5 distinct groups and the 2 parent lines. Seed germination was then evaluated throughout these 7 groups and statistical analysis revealed that faster germination was associated with 2 markers at the telomeric end of C1. Co-localization of these markers with a single BAC on the telomeric end of C1 was further assessed by Fluorescence In-Situ Hybridization. The BAC was sequenced and 12 full-length genes were found to be present within.

Putative orthologs of these *Brassica* genes have been identified in *Arabidopsis*, at the top arm of chromosome 3, where a SOG1 QTL has been located (Clerkx et al. 2004).

Figure 5:
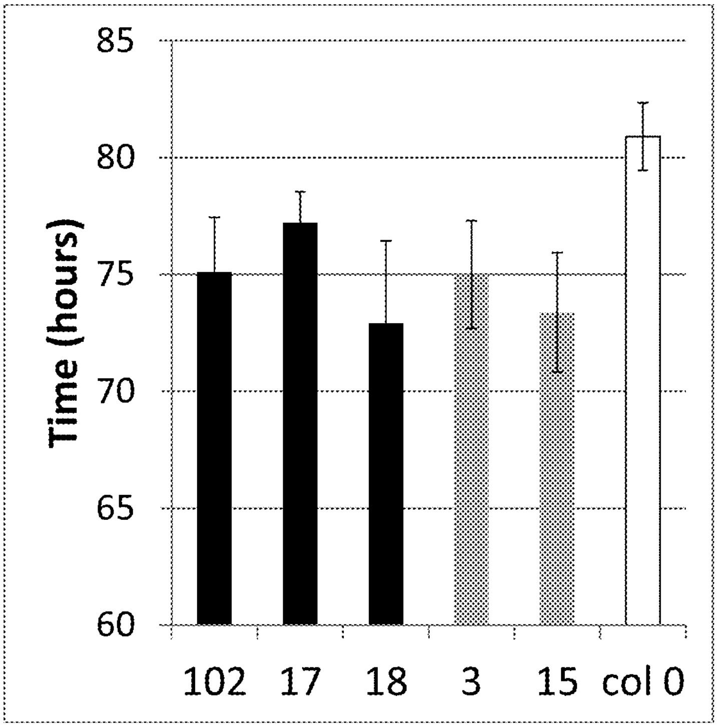
FIG. 5 is a diagram illustrating the speed of seed germination in 3, for gene At3g01060 (black columns), and 2, for gene At3g01150 (grey columns), KO lines. The wild type control line (white column) is col0.
Figure 6:
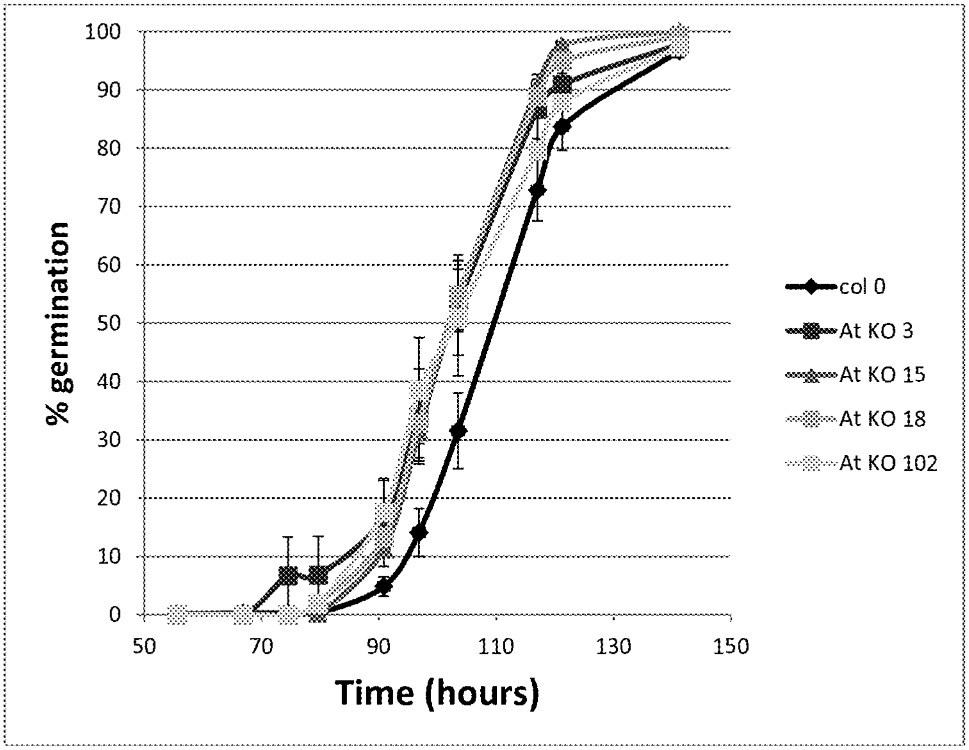
FIG. 6 is a diagram illustrating the speed of seed germination in KO lines 102 (light grey line) and 18 (low medium grey line) (for gene At3g01060) and in KO lines 15 (high medium grey line) and 3 (dark grey line) (for gene Atg01150) compared to wild type control line Col0 (black line), following seed production in the glasshouse (more stressful conditions).

Based on the good genetic colinearity between the telomeric end of C1 in *Brassica oleracea* and the top arm of chromosome 3 in *Arabidopsis* (see above and below), it is reasonable to think that the genes that were identified in *Brassica* and in *Arabidopsis* do share common function in seed germination. In order to strengthen our hypothesis, we have identified *Arabidopsis* knockout (KO) mutant lines in putative ortholog genes of those that have been discovered in *Brassica*. Two of these KO lines were found to have a significant germination phenotype (faster germination compared to control Col0 line) suggesting that these genes act as negative regulators of germination (FIG. 5). It is interesting to note that at least two different KO lines were used to assess germination phenotype and that these distinct KO lines showed similar results regarding to the speed of germination. When assessed following seed production in more stressful conditions (FIG. 6), the results are very comparable.

This functional study has thus confirmed the role of Atg01060 and Atg01150 genes in the regulation of seed vigour, in particular in the regulation of the speed of germination. The *Brassica* orthologs of these genes, BolC.VG1.a and BolC.VG1.b, which have been identified within the SOG1 QTL in *Brassica oleracea*, can therefore indeed be considered as tools allowing the modulation of the seed vigour, more particularly the modulation of the speed of seed germination in brassicaceae.

The Linkage Between *B. oleracea* Linkage Group C1 and the Top Arm of Chromosome Three of *Arabidopsis* is Confirmed Studies on SL101 above have shown that a single introgressed region at the telomeric end of linkage group C1 (LGC1) contains the QTL for SOG1. In the current work we aimed to establish colinearity between this region in *B. oleracea* and the *Arabidopsis* genome to enable comparison with the extensive QTL analysis carried out on this model species. Previously a number of linkages have been shown between the *Brassica* genome and *Arabidopsis* (Cogan et al., 2004; Parkin et al., 2005).

In particular, the linkage between the LGC1 and *Arabidopsis* (Cogan et al., 2004) was utilized to assist in the development of further informative markers. Using this approach, primer pairs were designed to 30 *Arabidopsis* gene models, which were spread across this region. These primers were tested to determine if they amplified a *B. oleracea* product and then if there were any polymorphisms between SL101 and the parental lines A12DHd and GD33DHd (table 1). A banding pattern that is the same in SL101 and GD33DHd, but different from that in A12DHd indicates its presence at this locus, and therefore its usefulness as a marker for SOG1. Primers for three gene models were identified as informative markers (At3g01190, At3g07130, At3g02420, table 1) that anchored the linkage between the top arm of *Arabidopsis* chromosome three and the SOG1 region of *B. oleracea* LGC1. This confirmation of colinearity justifies comparison of SOG1 with QTL for seed performance located to this region of the *Arabidopsis* genome.

TABLE 1

Primers for selected markers used to anchor SL101 introgression to Arabidopsis

| Gene model | Primers |
|---|---|
| At3g01190 | F: TTCTTCCACGACTGCTTCG (SEQ ID NO: 1) |
| | R: CTAACAAAACTGATCCGTCAC (SEQ ID NO: 2) |
| At3g02420 | F: GTTGCGTTGCCATCTGCAG (SEQ ID NO: 3) |
| | R: CAGGCTGAGATAGCCATTGG (SEQ ID NO: 4) |
| At3g07130 | F: CTACTAACCATGGAGTTACC (SEQ ID NO: 5) |
| | R: AACGCTGGTGGGATTCAC (SEQ ID NO: 6) |

Altogether, these results open up the possibility of using either BolC.VG1.a A12/GD33 alleles or BolC.VG2.a A12/GD33 alleles or BolC.VG2.b A12/GD33 alleles according to any of embodiments 1 to 23, in particular to engineer plants in which the seed vigour has been modulated, more particularly plants in which speed of germination has been modulated.

Example 2. Experiments Highlighting Additional Phenotypes Linked to Seed Vigour These experiments underlines the differences in germination characteristics between seeds with (SL101) or without (A12) the GD33 allele.

Seeds of the lines A12 and SL101 originated in the UK and were replicated in 2009 in South Africa by a commercial seed producer. Determination of the germination characteristics of the seeds took place in early 2010 in Enkhuizen, Netherlands.

Seed Performance Under Standard Commercial Conditions

Two replicates of 100 seeds were sown in standard trays filled with soil as in a normal commercial practice. Trays were placed in a germination chamber at 18° C. in the dark for three days. Trays were then transferred to a greenhouse with an average temperature of 20° C. At 10 days after sowing the number of normally developed seedlings and the number of non-emerged seeds were counted.

Performance of SL101 under these conditions was considerably better than for A12 (table 2).

TABLE 2

Percentage normal seedlings and percentage non germinated seeds as measured under practical conditions of seedling production

| | normal seedlings | non germinated seeds |
|---|---|---|
| A12 | 19 | 80 |
| SL101 | 91 | 7 |

Temperature Sensitivity of Germination on Paper

Two replicates of 100 seeds of each A12 and SL101 were sown for each combination of conditions on wet filter paper in transparent plastic germination boxes at temperatures of 10, 20 or 30° C. Boxes were either kept in the dark at the mentioned temperatures or were placed under fluorescent light.

Germination, measured as radical protrusion, was counted daily. Germination was counted until 10 days after the start of the measurement when no additional germination was observed.

The data show that under each condition the percentage germination was higher for SL101 compared to A12 (table 3).

TABLE 3

Final germination percentage of A12 and SL101 at different temperatures in the light or in the dark

| | | temperature | | |
|---|---|---|---|---|
| | | 10 | 20 | 30 |
| light | A12 | 47 | 94 | 59 |
| | SL101 | 94 | 100 | 99 |
| dark | A12 | 65 | 24 | 2 |
| | SL101 | 95 | 78 | 50 |

Speed of Germination on Paper

Speed of germination was determined under conditions of 20° C. in the light, a condition where both lines had their maximum germination. Two replicates of 50 seeds per line were placed on paper in plastic germination boxes under the mentioned conditions. The t50 (time until 50% of the germinating seeds have germinated) was determined (table 4).

As shown in the table the time until 50% germination was considerably shorter for SL101 compared to A12.

TABLE 4

Time until 50% germination at 20° C. in the light for A12 and SL101

| line | t50 (h) |
|---|---|
| A12 | 59.0 |
| SL101 | 47.5 |

Sensitivity to Low Temperatures During Germination on Paper

Two replicates of 50 seeds per treatment were incubated at 5° C. or 10° C. in the light as described before for a germination test on paper. Incubation was in water or in a 1 mM solution of GA3. After 10 days seeds that had germinated were removed. The boxes with the remaining non-germinated seeds were then placed at 20° C. in the light. After a further 5 days the number of germinated seeds was counted. As a comparison seeds of both A12 and SL101 were germinated at 20° C. in the light without a pretreatment. Germination percentage of these seeds was counted after 10 days.

Especially at 5° C. there was a large difference between the two lines (table 5). The pretreatment in water largely prevented for A12 germination at 20° C. in the light later on. This was not the case for pretreatment in 1 mM GA3. SL101 showed only a minor reduction in germination after the pretreatment at 5° C. in water.

TABLE 5

Percentage of germination of seeds of A12 and SL101 with or without a pretreatment at 5 or 10° C. in the light with an incubation medium of either water or a 1 mM aqueous solution of GA3

| | A12 | SL101 |
|---|---|---|
| no pretreatment | 99 | 100 |
| 10 d 5 C. in water | 15 | 84 |
| 10 d 5 C. in 1 mM GA3 | 100 | 100 |
| 10 d 10 C. in water | 82 | 99 |
| 10 d 10 C. in 1 mM GA3 | 100 | 100 |

Example 3 Effect of Genotype on Hybrid Seed Performance

Hybrid seeds were produced under commercial seed production conditions in South Africa by pollinating flowers of two male sterile lines with pollen from 7 other lines.

Female line 1 contained the GD33 allele, female line 2 contained the A12 allele.

The sensitivity to low temperature during germination was tested for these seeds. Seeds were incubated on moistened filter paper at 5° C. in white fluorescent light for 10 days. Percent germination was recorded after 10 days and non germinated seeds were transferred to 20° C. in light. After five days the percentage germinated seeds was recorded.

Seeds produced on the female line containing the GD33 allele showed considerably higher germination at 5° C. and germinated more than 90% after transfer to 20° C. Seeds produced on the female without the GD33 allele showed only low germination percentages and did not recover after transfer to 20° C.

TABLE 6

Percentage of germination of hybrid seeds produced using a GD33 or A12 female line with a pretreatment for 10 days at 5° C. in the light followed by incubation of non germinated seeds for 5 days at 20° C.

| | female 1 (GD33) | | female 2 (A12) | |
|---|---|---|---|---|
| | 10 d 5 C. | +5 d 20 C. | 10 d 5 C. | +5 d 20 C. |
| male 1 | 35 | 96 | 0 | 6 |
| male 2 | 28 | 96 | 0 | 10 |
| male 3 | 72 | 94 | 19 | 44 |
| male 4 | 9 | 96 | 0 | 4 |
| male 5 | 43 | 100 | 0 | 8 |
| male 6 | 28 | 99 | 0 | 4 |
| male 7 | 69 | 97 | 35 | 58 |
| average | 41 | 97 | 8 | 19 |

Seeds from the same batches of hybrid seed were tested in a germination test on paper at 25° C. in white fluorescent light. From daily counts of germination the time until 50% germination was calculated (t50). The final germination percentage was determined after 5 days. All hybrids had at least 85% germination, the majority more than 95%. Seeds produced on the female line with the GD33 allele showed on average around 25% faster germination, shown by the lower t50 of 1.33 days versus 1.80 days for seeds produced on the female with the A12 allele.

TABLE 7

Percentage germination and time taken until 50% germination (t50) of hybrid seed produced using a GD33 or A12 female line in the light at 25° C.

| | female 1 (GD33) | | female 2 (A12) | |
|---|---|---|---|---|
| | germ % | t50 (d) | germ % | t50 (d) |
| male 1 | 100 | 1.08 | 99 | 1.73 |
| male 2 | 97 | 1.95 | 98 | 1.85 |
| male 3 | 98 | 1.85 | 100 | 1.90 |
| male 4 | 100 | 1.15 | 95 | 1.84 |
| male 5 | 99 | 1.07 | 98 | 1.68 |
| male 6 | 99 | 1.14 | 85 | 1.84 |
| male 7 | 95 | 1.05 | 98 | 1.79 |
| average | 98 | 1.33 | 96 | 1.80 |

REFERENCES

Bettey M., Finch-Savage W. E., King G. J., Lynn J. R. 2000. Quantitative genetic analysis of seed vigour and pre-emergence seedling growth traits in *Brassica oleracea* L. New Phytol 148: 277-286.

Clercks E. J. M., El-Lithy M. E., Vierling E., Ruys G. J., Blankestijn-De Vries H., Groot S. P. C., Vreugdenhil D., Koornneef M. 2004. Analysis of natural allelic variation of *Arabidopsis* seed germination and seed longevity traits between the accessions Landsberg errecta and Shakdara, using a new recombinant inbred line population. Plant Physiol 135: 432-443.

Finch-Savage W. E. 1995. Influence of seed quality on crop establishment, growth and yield. In A S Basra, ed. Seed quality: Basic mechanisms and agricultural implications. Haworth Press, Inc, New York, pp 361-384.

Finch-Savage W. E., Côme D., Ly J. R., Corbineau F. 2005. Sensitivity of *Brassica oleracea* seed germination to hypoxia: a QTL analysis. Plant Sci 169: 753-759.

Finch-Savage W. E, and Leubner-Metzger G. 2006. Seed dormancy and the control of germination. New Phytol. 171: 501-523.

Finkelstein R. R., Gampala S. S., and Rock C. D. 2002. Abscisic acid signaling in seeds and seedlings. Plant Cell 14, S15-45.

Foolad M. R., Lin G. Y., Chen F. Q. 1999. Comparison of QTLs for seed germination under non-stress, cold stress and salt stress in tomato. Plant Breed 118: 167-173.

Groot S. P. C., van der Geest A. H. M., Tesnier K. J. Y., Alonso-Blanco C., Bentsink L., Donkers H., Koornneef M., Vreugdenhil D., Bino R. J. 2000. Molecular genetic analysis of *Arabidopsis* seed quality. In M Black, J Vasquez-Ramos, eds, Seed Biology: Advances and applications, CAB International., London, pp 123-132.

Hilhorst H. W. M. and Toorop P. E. 1997. Review on dormancy, germinability and germination in crop and weed seeds. Advances Agron 61: 115-165.

Holdsworth M. J., Bentsink L., Soppe W. J. J. 2008a. Molecular networks regulating *Arabidopsis* seed maturation, after-ripening, dormancy and germination. New Phytol 179: 33-54.

Holdsworth M. J., Finch-Savage W. E., Grappin P., Job J. 2008b. Post-genomics dissection of seed dormancy and germination. Trends Plant Sci 13: 7-13.

Ruan S. L., Duan X. M. and Hu W. M. 2000. Occurrence of seed vivipary in hybrid rape (*Brassica napus* L.) and its effect on seed quality. Journal of Zhejiang University (Agriculture and Life Sciences) 2000 Vol. 26 No. 5 pp. 573-578.

Sequence Alignments

DNA sequence alignment for the *Brassica oleracea* VG2 genes. Alignments were performed using the ClustalW web based program (on the World Wide Web at genome.jp) and the annotation is drawn using the web based program BOXSHADE (on the World Wide Web at ch.embnet.org). A12_BOLC.VG2.A is an A12 full length copy of the gene located in the SOG1 region of linkage group C1. A12_BOLC.VG2.B is a truncated copy of a similar gene located within 50 Kb of the full length gene. A similar annotation has been used to describe the same region in the GD33 genomic background.

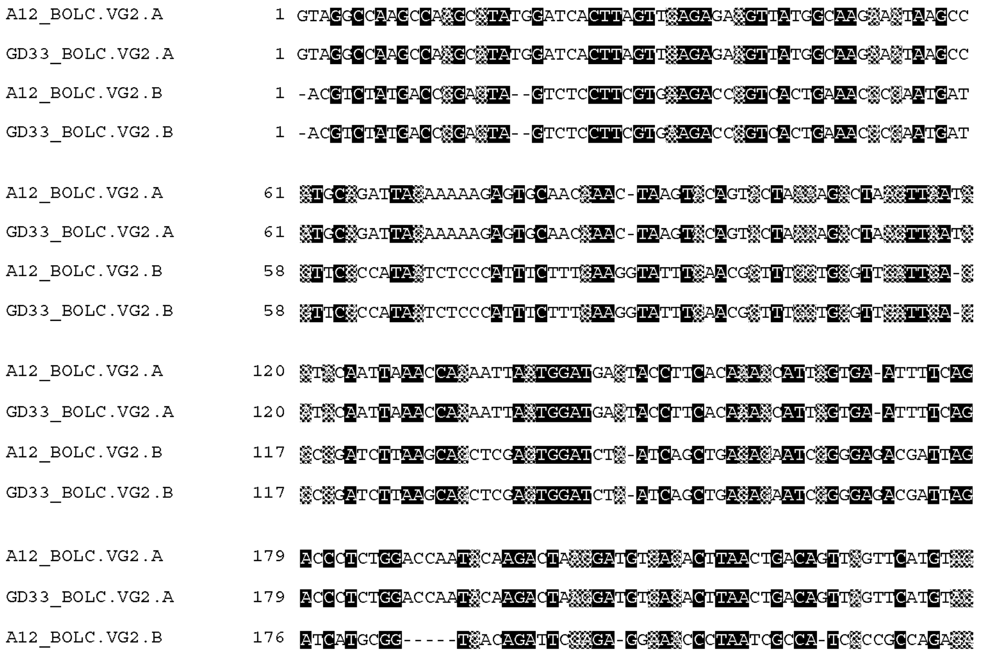

-continued

GD33_BOLC.VG2.B 176 ATCATGCGG-----TGACAGATTCGAGA-GGAAACCCTAATCGCCA-TCGCCGCCAGAGA

A12_BOLC.VG2.A 239 GGCCAATAAGCAGCTCAAATTCGTTAGCTTTCAAGTTCGATTTTCTGCGTTGTGTTTTG

GD33_BOLC.VG2.A 239 GGCCAATAAGCAGCTCAAATTCGTTAGCTTTCAAGTTCGATTTTCTGCGTTGTGTTTTG

A12_BOLC.VG2.B 229 GTCTCATCTGCAGTGTGA-----TTCATATGCAAATCTCCTGGATTTG-GTTGTTTTTTT

GD33_BOLC.VG2.B 229 GTCTCATCTGCAGTGTGA-----TTCATATGCAAATCTCCTGGATTTG-GTTGTTTTTTT

A12_BOLC.VG2.A 299 CTTTTTGAGGGTTGATTTGGAATTTCTCCAAAGAGGTCACATAATTTAAAAGAAATTGAT

GD33_BOLC.VG2.A 299 CTTTTTGAGGGTTGATTTGGAATTTCTCCAAAGAGGTCACATAATTTAAAAGAAATTGAT

A12_BOLC.VG2.B 283 CTTTTTCAGGTTTGATTTGGAATTTCTCTAAAGAGGTCACATTAATTAAAATAAACTAGA

GD33_BOLC.VG2.B 283 CTTTTTCAGGTTTGATTTGGAATTTCTCTAAAGAGGTCACATTAATTAAAATAAACTAGA

A12_BOLC.VG2.A 359 CAAAATTATATTGGACAAG--GCAAGCAAATCCATTAAGAAGATCACAACAAAAGAAAAA

GD33_BOLC.VG2.A 359 CAAAATTATATTGGACAAG--GCAAGCAAATCCATTAAGAAGATCACAACAAAAGAAAAA

A12_BOLC.VG2.B 343 CCCTTATCCGCGCGCCAGC--GCAGATATCAATTTTTAGTTTTTAATTATTTATTTTATT

GD33_BOLC.VG2.B 343 CCCTTATCCGCGCGCCAGC--GCAGATATCAATTTTTAGTTTTTAATTATTTATTTTATT

A12_BOLC.VG2.A 417 TTAAAAACCAACAAAAGAAATTTCCCATTTGACGAAGGTGATGAACAAGATCAGTACGTA

GD33_BOLC.VG2.A 417 TAAAAAACCAACAAAAGAAATTTCCCATTTGACGAAGGTGATGAACAAGATCAGTACGTA

A12_BOLC.VG2.B 401 CAATGATGTATTTGTAAATATTCGTTCATATTATATTCGTTAAGTA-AATATTTTTTTGTA

GD33_BOLC.VG2.B 401 CAATGATGTATTTGTAAATATTCGTTCATATTATATTCGTTAAGTA-AATATTTTTTTGTA

A12_BOLC.VG2.A 477 TGCTCCACCAATGCATGACACTACTGAAAGCATAGA--CAAACAAGGTCGTGATAGTTGT

GD33_BOLC.VG2.A 477 TGCTCCACCAATGCATGACACTACTGAAAGCATAGA--CAAACAAGGTCGTGATAGTTGT

A12_BOLC.VG2.B 460 T-CTTAAACTATCTATTTTTTTAC-GAATGTGTGATATCATATAAAAATATTA-AGAAGT

GD33_BOLC.VG2.B 460 T-CTTAAACTATCTATTTTTTTAC-GAATGTGTGATATCATATAAAAATATTA-AGAAGT

A12_BOLC.VG2.A 535 GACCACCTCACGCATGAAAAAACTCCATGAATGTCAAGAGTTTGCACGATTGTGTAAACA

GD33_BOLC.VG2.A 535 GACCACCTCACGCATGAAAAAACTCCATGAATGTCAAGAGTTTGCACGATTGTGTAAACA

A12_BOLC.VG2.B 517 GAGTATAGAGTTAATGAGATAATTTTAAAAACAGAAATTTTTCTTTCGTGTGCCATATCA

GD33_BOLC.VG2.B 517 GAGTATAGAGTTAATGAGATAATTTTAAAAACAGAAATTTTTCTTTCGTGTGCCATATCA

A12_BOLC.VG2.A 595 CTTAATCACTTATTCGTTGAAGGATAATGTTGGACAGAATATTATCATTGTTTCTAGTGG

GD33_BOLC.VG2.A 595 CTTAATCACTTATTCGTTGAAGGATAATGTTGGACAGAATATTATCATTGTTTCTAGTGG

A12_BOLC.VG2.B 577 TATAAGTAATGATCCGCCCAG---------TTGACAGAA-ATCATGATTATTTTATGTG-

GD33_BOLC.VG2.B 577 TATAAGTAATGATCCGCCCAG---------TTGACAGAA-ATCATGATTATTTTATGTG-

A12_BOLC.VG2.A 655 TAAGCATGAGCAGACATTGTAAAAAGGAGTCATGATCATGCTATATCTTATAGGAGTTTA

GD33_BOLC.VG2.A 655 TAAGCATGAGCAGACATTGTAAAAAGGAGTCATGATCATGCTGTATCTTATAGGAGTTTA

A12_BOLC.VG2.B 626 TAATTTTCTTTAT---TTTGACTATTTCCTTAAAACTATATTAAATTTTACAT-ATTTTA

GD33_BOLC.VG2.B 626 TAATTTTCTTTAT---TTTGACTATTTCCTTAAAACTATATTAAATTTTACAT-ATTTTA

A12_BOLC.VG2.A 715 ATTTATTCCAAGTTCACATTTAGTGATGCTCTGATCTTCAA--CAATAAAACATAACCAA

GD33_BOLC.VG2.A 715 ATTTATTCCAAGTTCACATTTAGTGATGCTCTGATCTTCAA--CAATAAAACATAACCAA

A12_BOLC.VG2.B 682 ATTAGAATGTTTTTGATATCT--TTACCTTTTTATTTGAAATGCAACTCAATATTTTTTT

GD33_BOLC.VG2.B 682 ATTAGAATGTTTTTGATATCT--TTACCTTTTTATTTGAAATGCAACTCAATATTTTTTT

-continued

| | | |
|---|---|---|
| A12_BOLC.VG2.A | 773 | CTGATAGTCAGAGTAACCAATTGAATGCCAGTTTTCAAAAGAAAT--GATACATATCTAA |
| GD33_BOLC.VG2.A | 773 | CTGATAGTCAGAGTAACCAATTGAATGCCAGTTTTCAAAAGAAAT--GATACATATCTAA |
| A12_BOLC.VG2.B | 740 | TTAACAATTATAGCAAAATATTTAAAGAATGTTTTTAGAATTTGTTTGAAAAATATCAAA |
| GD33_BOLC.VG2.B | 740 | T-AACAATTATAGCAAAATATTTAAAGAATGTTTTTAGAATTTGTTTGAAAAATATCAAA |
| | | |
| A12_BOLC.VG2.A | 831 | CTGATAGTCAGTCAAATCAACCAAATAAGTAGAAAGAACCAAACAAGCACAACTACGCGT |
| GD33_BOLC.VG2.A | 831 | CTGATAGTCAGTCAAATCAACCAAATAAGTAGAAAGAACCAAACAAGCACAACTACGC-T |
| A12_BOLC.VG2.B | 800 | GTTACATT---TTAAATTAA---AATTATCCTAAAGTAT--GATAAGTTTTGATGTAAAC |
| GD33_BOLC.VG2.B | 799 | GTTACATT---TTAAATTAA---AATTATCCTAAAGTAT--GATAAGTTTTGATGTAAAC |
| | | |
| A12_BOLC.VG2.A | 891 | GGACACTTCGATTATTTTGTAGGTTCGGTTTGGATTCGGTTCGGTTTGGTTAATTTATTC |
| GD33_BOLC.VG2.A | 890 | GGACACTTCGATTATTTTGTAGGTTCGGTTTGGATTCGGTTCGGTTTGGTTAATTTATTC |
| A12_BOLC.VG2.B | 852 | GGAAACTCAAATTATGTCAAAGAT---GGTGGTATTCAATG-ATAATGGCAATTTTAATT |
| GD33_BOLC.VG2.B | 851 | GGAAACTCAAATTATGTCAAAGAT---GGTGGTATTCAATG-ATAATGGCAATTTTAATT |
| | | |
| A12_BOLC.VG2.A | 951 | TAGAATTTTTTAAACTGAAGTAAACCATAAGTTTCAGTCTGGTTTGTATTCGGCATGGTT |
| GD33_BOLC.VG2.A | 950 | TAGAATTTTTTTAACTGAAGTAAACCATAAGTTTCAGTCTGGTTTGTATTCGGCATGGTT |
| A12_BOLC.VG2.B | 908 | GATTATTTTTTAAA---AAGTA---CATTTGCAAAAGTATTGTTTGGAAGAGAATTCATT |
| GD33_BOLC.VG2.B | 907 | GATTATTTTTTAAA---AAGTA---CATTTGCAAAAGTATTGTTTGGAAGAGAATTCATT |
| | | |
| A12_BOLC.VG2.A | 1011 | TGTGTTTCAGTTCGGTTTAATCGGATTCCCTTAATTTAATTCTTTTAAGAAGAATCATGT |
| GD33_BOLC.VG2.A | 1010 | TGTGTTTCAGTTCGGTTTAATCGGATTCCCTTAATTTAATTCTTTTAAGAAGAATCATGT |
| A12_BOLC.VG2.B | 962 | TATCTTTCAAGT--ATAGAATGAAAATGTTATAATTAAATAATAAAAAATATAAATAAAG |
| GD33_BOLC.VG2.B | 961 | TATCTTTCAAGT--ATAGAATGAAAATGTTATAATTAAATAATAAAAAATATAAATAAAG |
| | | |
| A12_BOLC.VG2.A | 1071 | TTTAGAACACGGTCATGAGATCATCGTGTTGGTGACTATGAAAAAATAAATTATATAATT |
| GD33_BOLC.VG2.A | 1070 | TTTAGAACATGGTCATGAGATCATCGTGTTGGTTACTATGAAAAAATAAATTATATAATT |
| A12_BOLC.VG2.B | 1020 | ACCATAAATTTAGCAAATGACAACTGAGTTA--TATTATGCTAAAAAAAAGTTTCTAACA |
| GD33_BOLC.VG2.B | 1019 | ACCATAAATTTAGCAAATGACAACTGAGTTA--TATTATGCTAAAAAAAAGTTTCTAACA |
| | | |
| A12_BOLC.VG2.A | 1131 | AAATCTAATAT-ATAACTGAGACAAGAGTCCTAAAAAACCACAAAAAAATTTATAAGAAC |
| GD33_BOLC.VG2.A | 1130 | AAATCTAATAT-ATAACTGAGACAAGAGTCCTAAAAAACCACAAAAAATTTTATAAGAAC |
| A12_BOLC.VG2.B | 1078 | AAATATCAAATGACAAATGAGTTATGAGT----AAATAATACCATATAATTTTTAAGAAC |
| GD33_BOLC.VG2.B | 1077 | AAATATCAAATGACAAATGAGTTATGAGT----AAATAATACCATATAATTTTTAAGAAC |
| | | |
| A12_BOLC.VG2.A | 1190 | ACAATCAAGCCGAAGT-TGACTAAAGTAAATAGAAAGTTAAAAAAGAAA-CAATGTCAAT |
| GD33_BOLC.VG2.A | 1189 | ACAATCAAGCCGAAGT-TGACTAAAGTAAATAGAAAGTTAAAAAAGAAAACAATGTCAAT |
| A12_BOLC.VG2.B | 1134 | ATAGCCATTCTTAAATGTTTTTTGAGTAAATAGTTATTTTAAATTTAATCAACTGAAAAT |
| GD33_BOLC.VG2.B | 1133 | ATAGCCATTCTTAAATGTTTTTTGAGTAAATAGTTATTTTAAATTTAATCAACTGAAAAT |
| | | |
| A12_BOLC.VG2.A | 1248 | AAAGTTAGTACTGACTTTGGTGTTAGGATTTAGTGTGAAAATGTTTGATTCAAGTAATAA |
| GD33_BOLC.VG2.A | 1248 | AAAGTTAGTACTGACTTTGGTGTTAGGATTTAGTGTGAAAATGTTTGATTCAAGTAATAA |
| A12_BOLC.VG2.B | 1194 | AATGTCTGTACGATTGTGTGAGTCAGGTTCTAGTTTTA------TTGATGCATGTTATAT |
| GD33_BOLC.VG2.B | 1193 | AATGTCTGTACGATTGTGTGAGTCAGGTTCTAGTTTTA------TTGATGCATGTTATAT |
| | | |
| A12_BOLC.VG2.A | 1308 | CAAAGGCGCGTTGGTTTTTCGGTGCAATTTGATTCGGTTCGATTCGGTTCGGTCTGATTT |
| GD33_BOLC.VG2.A | 1308 | CAAAGGCGCGTTGGTTTTTCGGTGCAATTTG-TTCGGTTTGATTCGGTTCGGTCTGATTT |

-continued

```
A12_BOLC.VG2.B     1248  ▒TTAGTGCT▒CATGTTTTAGGT▒▒CATTTT▒AT▒▒TGCACGTTTTCA▒▒▒▒TCTCCATTA
GD33_BOLC.VG2.B    1247  ▒TTAGTGCT▒CATGTTTTAGGT▒▒CATTTT▒AT▒▒TGCACGTTTTCA▒▒▒▒TCTCCATTA

A12_BOLC.VG2.A     1368  TTTT▒CTT▒TCTGAACACAACGAC▒▒CCGACA▒▒TAACTTTTTAAAC▒TTAC▒TGAAAAT
GD33_BOLC.VG2.A    1367  TTTT▒CTTCTCTGAACACAACGAC▒▒CCGACA▒▒TAACTTTTTAAAC▒TTAC▒TGAAAAT
A12_BOLC.VG2.B     1308  TTAAAATT▒--TGCAC▒TAATGAT▒▒CTCAT▒A▒T-TTTTTT▒TT▒ATTAAATGACATT
GD33_BOLC.VG2.B    1307  TTAAAATT▒--TGCAC▒TAATGAT▒▒CTCAT▒A▒T-TTTTTT▒TT▒ATTAAATGACATT

A12_BOLC.VG2.A     1428  ▒T▒T▒▒ACTATTGG▒CCTTAGTAAAGGCTAAT▒A▒C▒▒ATTAAAT▒▒GCTTATA▒AC▒C
GD33_BOLC.VG2.A    1427  ▒T▒T▒▒ACTATTGG▒CCTTAGTAAAGGCTAAT▒A▒C▒▒ATTAAAT▒▒GCTTATA▒AC▒C
A12_BOLC.VG2.B     1365  ATGTCCAAATTT---▒TTTAAGGATATTTCATTAA▒GTAA▒T▒AAAA▒GACAAAC▒AT▒A
GD33_BOLC.VG2.B    1364  ATGTCCAAATTT---▒TTTAAGGATATTTCATTAA▒GTAA▒T▒AAAA▒GACAAAC▒AT▒A

A12_BOLC.VG2.A     1488  AATTGCATGGTATCTATC▒G▒-AAGCATAAATC▒TCAA▒TAATTCAATTTA▒▒▒GACTCA
GD33_BOLC.VG2.A    1487  AATTGCATGGTATCTATC▒G▒-AAGCATAAATC▒TCAA▒TAATTCAATTTA▒▒▒GACTCA
A12_BOLC.VG2.B     1422  AATAGGAAGTTT▒AAATCATTTAAGCATATTTCAT----TAATGTAACT▒AA▒▒GACA-A
GD33_BOLC.VG2.B    1421  AATAGGAAGTTT▒AAATCATTTAAGCATATTTCAT----TAATGTAACT▒AA▒▒GACA-A

A12_BOLC.VG2.A     1547  TTTGCAATTT▒TGCAAAGATTTTAGCTGTACAGA▒TAGG▒CT▒▒▒CATAAAATCCGTAAC
GD33_BOLC.VG2.A    1546  TTTGCAATTT▒TGCAAAGATTTTAGCTGTACAGA▒TAGG▒CT▒▒▒CATAAAATCCGTAAC
A12_BOLC.VG2.B     1477  GTA▒TAAATT▒GGCA▒---TTTTATTCGTTT----TATGATATTTCATAAA---TGCAAC
GD33_BOLC.VG2.B    1476  GTA▒TAAATT▒GGCA▒---TTTTATTCGTTT----TATGATATTTCATAAA---TGCAAC

A12_BOLC.VG2.A     1607  CCGAAATCCGAACC▒AACC▒AAAAACCCG▒TCC▒TACCC▒ATCC▒AAATGTAAAAAATAC
GD33_BOLC.VG2.A    1606  CCGAAATCCGAACC▒AACC▒AAAAACCCG▒TCC▒TACCC▒ATCC▒AAATGTAAAAAATAC
A12_BOLC.VG2.B     1527  T▒GAAAAGACAAAC▒AA--AAAAAATA▒G▒AGTTTAATTAAT--▒AAAT▒-A▒AACATTT
GD33_BOLC.VG2.B    1526  T▒GAAAAGACAAAC▒AA--AAAAAATA▒G▒AGTTTAATTAAT--▒AAAT▒-A▒AACATTT

A12_BOLC.VG2.A     1667  CTCAATGAATATTGTAG▒▒T▒TTATAAAATATATCTGAACCCGAA▒TGTTATTAACCGAA
GD33_BOLC.VG2.A    1666  CTCAATG▒ATATTGTAG▒▒T▒TTATAAAATATATCTGAACCCGAA▒TGTTATTAACCGAA
A12_BOLC.VG2.B     1582  TCAAATGA▒TACTTC----TCTTTTAATA-ATAT---------A▒ATTTCATTAAT-GTA
GD33_BOLC.VG2.B    1581  TCAAATGA▒TACTTC----TCTTTTAATA-ATAT---------A▒ATTTCATTAAT-GTA

A12_BOLC.VG2.A     1727  CCCGAACGGATAATCC▒AAAACCCG▒AAAACCAAAAAATTC▒AA▒AAATATCCGAAAAAA
GD33_BOLC.VG2.A    1726  CCCGAACGGATAATCC▒AAAACCCG▒AAAACCAAAAAACTC▒AA▒AAATATCCGAAAAAA
A12_BOLC.VG2.B     1627  ACTGAA▒▒GACAA▒T▒ATAAATTAC▒CA▒TTTTATTC▒TTTTA▒TATATTTC---ATAAA
GD33_BOLC.VG2.B    1626  ACTGAA▒▒GACAA▒T▒ATAAATTAC▒CA▒TTTTATTC▒TTTTA▒▒ATATTTC---ATAAA

A12_BOLC.VG2.A     1787  CT▒ATCCGAAT▒CGTAAATTAATATAAAAATATAA▒TATTT▒AA▒CAT▒CA-TTG▒▒TAT▒
GD33_BOLC.VG2.A    1886  CT▒ATCCGAAT▒CGTAAATTAATATAAAAATATAA▒TATTT▒AA▒CAT▒CA-TTG▒▒TAT▒
A12_BOLC.VG2.B     1684  TGCAACTGAA▒AAG▒CAAGAAAAA-AAAATA-AA▒AATTTAATT▒ATG▒A-GT▒AG▒ATA
GD33_BOLC.VG2.B    1683  TGCAACTGAA▒AAG▒CAAGAAAAA-AAAATA-AA▒AATTTAATT▒ATG▒A-GT▒AG▒ATA

A12_BOLC.VG2.A     1846  ATATCTAACAA-TAAGTATTT▒▒AATTTAATA▒AT▒CTTTAAATACTCCATT▒TATACA
GD33_BOLC.VG2.A    1845  ATATCTAACAA-TAAGTATTT▒▒AATTTAATA▒▒T▒CTTTAAATACTCTATT▒TATACA
A12_BOLC.VG2.B     1741  TTTTC▒AAT▒AGTATTTCTCTTTTAATAATATA▒ATTG▒TCAAAAATTATATTGGATA-A
GD33_BOLC.VG2.B    1740  TTTTC▒AAT▒AGTACTTCTCTTTTAATAATATA▒ATTG▒TCAAAAATTATATTGGATA-A
```

-continued

```
A12_BOLC.VG2.A      1905  AA--GAAGTATATATTTTTTATGTTTTACTTTTGAATTTTAGATTTTACTATCGATATAT
GD33_BOLC.VG2.A     1904  AA--GAAGTATATATTTTTTATGTTTTACTTTTGAATTTTAGATTTTACTATCTATATAT
A12_BOLC.VG2.B      1800  AG--CAAGCA-AAATCCATTGAGAAGATCACAACAACAAAAGAGAGGAACAGGCACACAA
GD33_BOLC.VG2.B     1799  AG--CAAGCA-AAATCCATTGAGAAGATCACAACAACAAAAGAGAGGAACAGGCACACAA

A12_BOLC.VG2.A      1963  CCAAGCCGATCCGATA--CAATCCGAATCCGAATGTTCTATGGCTACTTTTGATATATCT
GD33_BOLC.VG2.A     1962  CCAAGCCGATCCGATA--CAATCCGAATCCGAATGTTCTATGGCTATTTTTGATATATCT
A12_BOLC.VG2.B      1857  CCGCGACGA-CAGATAACTAAGGTGTACTGGACTATTGGGCCCTTAATATAGACTAAT--
GD33_BOLC.VG2.B     1856  CCGCGACGA-CAGATAACTAAGGTGTACTGGACTATTGGGCCCTTAATATAGACTAAT--

A12_BOLC.VG2.A      2021  GAACCGATCCGAAACCGAAGTTGTTATATCCCAATCTCATCCGTACTTATAAATTTACTA
GD33_BOLC.VG2.A     2020  GAACCGATCCGAAACCGAAGTTGTTATATCCCAATCTCATCCGTACTGATAAATTTACTA
A12_BOLC.VG2.B      1914  GAACAGATT---AAATGAGCTAGTTATAGACGTCATTGCATAGTATCCATCTATCTAGAA
GD33_BOLC.VG2.B     1913  GAACAGATT---AAATGAGCTAGTTATAGACGTCATTGCATAGTATCCATCTATCTAGAA

A12_BOLC.VG2.A      2081  GA-ATGAGACATAGGGGATGATACGAAATAGAACCGAAATCCGAAAGAGCCGATCCGAGC
GD33_BOLC.VG2.A     2080  GA-ATGAGACACAGGGGATGATACGAAATAGAACCGAAATCCGAAAGAGCCGATCCGAGC
A12_BOLC.VG2.B      1971  GC-ATAGTAATTTG----TTTTAGAAAACTGATTTGCAATTTTTACAGAT--ATTTTAGC
GD33_BOLC.VG2.B     1970  GC-ATAGTAATTTG----TTTTAGAAAACTGATTTGCAATTTTTACAGAT--ATTTTAGC

A12_BOLC.VG2.A      2140  CCGAACGCCGAGGCCTAGTACAGAGTTCCGATCAGAGATAAAGAGAATCCTTTGAGCGTC
GD33_BOLC.VG2.A     2139  C-GAACGCCCAGGCCTAGTACAGAGTTCCGATCAGAGATAAAGAGAATCCTTTGAGCGTC
A12_BOLC.VG2.B      2024  T-----------GTACAGTACAGAG----------------AGAGAATCCTTTGAGCGTC
GD33_BOLC.VG2.B     2023  T-----------GTACAGTACAGAG----------------AGAGAATCCTTTGAGCGTC

A12_BOLC.VG2.A      2200  G---GCCTTGCTTTGTGCGTAGGGATCGTCT-CCGACTAATTGTTGTAATTATAAAAGGC
GD33_BOLC.VG2.A     2198  G---GCCTTGCTTTGTGCGTAGGGATCGTCT-CCGACTAATTGTTGTAATTATAAAAGGC
A12_BOLC.VG2.B      2057  GTCGGCCTTGCTTTGTGTGTAGGGATCTCCGACTGACTAATTGTTGTAACTACAAAAGGG
GD33_BOLC.VG2.B     2056  GTCGGCCTTGCTTTGTGTGTAGGGATCTCCGACTGACTAATTGTTGTAACTACAAAAGGG

A12_BOLC.VG2.A      2256  AGCC----GCGCCTTTTTAGCGGAGAGATGGCGAGCTCA---------CAGTTCAGGTAT
GD33_BOLC.VG2.A     2254  AGCC----GCGCCTTTTTAGCGGAGAGATGGCGAGCTCA---------CAGTTCAGGTAT
A12_BOLC.VG2.B      2117  CGCCCCCCGCGCCTTTTTACT----AGATGGCGAGCTCAT------CACAGTTTAGGTAT
GD33_BOLC.VG2.B     2116  CGCCCCCCGCGCCTTTTTACT----AGATGGCGAGCTCAT------CACAGTTTAGGTAT

A12_BOLC.VG2.A      2303  ACCCAGACGCCGTCGAAGGTGGTGCACCTGAGGAATCTGCCGTGGGAATGCGTGGAAGAG
GD33_BOLC.VG2.A     2301  ACCCAGACGCCGTCGAAGGTGGTGCACCTGAGGAATCTGCCGTGGGAATGCGTGGAAGAG
A12_BOLC.VG2.B      2167  ACCCAGACGCCGTCGAAGGTGGTGCACCTGAGGAATCTGCCGTGGGAATGCGTGGAAGAG
GD33_BOLC.VG2.B     2166  ACCCAGACGCCGTCGAAGGTGGTGCACCTGAGGAATCTGCCGTGGGAATGCGTGGAAGAG

A12_BOLC.VG2.A      2363  GAGCTCATCGACCTATGCAAACGATTCGGCAAGATCGTCAATACGAAGACCAATGTCGGC
GD33_BOLC.VG2.A     2361  GAGCTCATCGACCTATGCAAACGATTCGGCAAGATCGTCAATACGAAGACCAATGTCGGC
A12_BOLC.VG2.B      2227  GAGCTCATCGACCTATGCAAACGATTCGGCAAGATCGTCAATACGAAGACCAATGTCGGC
GD33_BOLC.VG2.B     2226  GAGCTCATCGACCTATGCAAACGATTCGGCAAGATCGTCAATACGAAGACCAATGTCGGC

A12_BOLC.VG2.A      2423  GCCAATCGCAACCAAGCCTTTGTCGAATTCGTAA---CAACT--------TTTTATTCTC
```

-continued

```
GD33_BOLC.VG2.A   2421 GCCAATCGCAACCAAGCCTTTGTCGAATTCGTAA---CAACT--------TTTTATTCTC
A12_BOLC.VG2.B    2287 GCCAATCGCAACCAAGCCTTTGTCGAATTCGTAA---GAACT--------TTTTATTCTC
GD33_BOLC.VG2.B   2286 GCCAATCGCAACCAAGCCTTTGTCGAATTCGTAA---CAACT--------TTTTATTCTC

A12_BOLC.VG2.A    2472 TTGGATCATCAGATTGTTTCT---------------------------------------
GD33_BOLC.VG2.A   2470 TTCGATCATCAGATTGTTTCTGAAG--------CTTTG-TGATTTCTATGATGAACTCTT
A12_BOLC.VG2.B    2336 TTGGATCATCAGATTGTTGCTTCCC--------CCCCAATGGATTTGGTTAGAAATTGAA
GD33_BOLC.VG2.B   2335 TTGGATCATCAGATTGTTGCTTCCC--------CCCCAATGGATTTGGTTAGAAATTGAA

A12_BOLC.VG2.A    2493 ------------------TTTTTTTGGTATCTCGTTGTTGT-----TTTGGTAT-----T
GD33_BOLC.VG2.A   2521 -----------------TTTTTTTTGGTATCTCGTTGTTGT-----TTTGGTAT-----T
A12_BOLC.VG2.B    2388 -----------------TAAAAAAAGGACTCGAACTCTTTT-----TTTGGTATCTCGTT
GD33_BOLC.VG2.B   2387 -----------------TAAAAAAAGGACTCGAACTCTTTT-----TTTGGTATCTCGTT

A12_BOLC.VG2.A    2524 GTT-------GTTTTGAAGATGAAACTGTATACTTT------------------GATTCA
GD33_BOLC.VG2.A   2554 GTT-------GTTTTGAAGATGAAACTGTATACTTT------------------GATTCA
A12_BOLC.VG2.B    2426 GTT-------GTTTTGAAGATGAAACTGTATACTTT------------------GATTCA
GD33_BOLC.VG2.B   2425 GTT-------GTTTTGAAGATGAAACTGTATACTTT------------------GATTCA

A12_BOLC.VG2.A    2559 TATT---------------------CGCAGGGTGACGTGAATCAGGCAATATCAATGGTT
GD33_BOLC.VG2.A   2589 TATT---------------------CGCAGGGTGACGTGAATCAGGCAATATCAATGGTT
A12_BOLC.VG2.B    2461 TATT---------------------CGCAGGGTGACGTGAATCAGGCAATATCAATGGTT
GD33_BOLC.VG2.B   2460 TATT---------------------CGCAGGGTGACGTGAATCAGGCAATATCAATGGTT

A12_BOLC.VG2.A    2598 TCTTACTATGCTTCGTCTTCAGAGCCGGCTCAGATTCGAGGGAAGACTGTTTATATTCAG
GD33_BOLC.VG2.A   2628 TCTTATTATGCTTCGTCTTCAGAGCCGGCTCAGATTCGAGGGAAGACTGTTTATATTCAG
A12_BOLC.VG2.B    2500 TCTTACTATGCTTCGTCTTCAGAGCCGGCTCAGATTCGAGGGAAGACTGTTTATATTCAG
GD33_BOLC.VG2.B   2499 TCTTACTATGCTTCGTCTTCAGAGCCGGCTCAGATTCGAGGGAAGACTGTTTATATTCAG

A12_BOLC.VG2.A    2658 TACTCTAATCGCCATGAGATTGTCAACAATCAGAGTCCTGGAGAGGTCCCTGGCAATGTC
GD33_BOLC.VG2.A   2688 TACTCTAATCGGCATGAGATTGTCAACAATCAGAGTCCTGGAGAGGTCCCTGGCAATGTC
A12_BOLC.VG2.B    2560 TACTCTAATCGCCATGAGATTGTCAACAATCAGAGTCCTGGAGAGGTCCCTGGCAATGTC
GD33_BOLC.VG2.B   2559 TACTCTAATCGCCATGAGATTGTCAACAATCAGAGTCCTGGAGAGGTCCCTGGCAATGTC

A12_BOLC.VG2.A    2718 CTCTTGGTCACCTTTGAAGGAGTCCAATCTCACCATGTCTGCATCGATGTCATCCATCTG
GD33_BOLC.VG2.A   2748 CTCTTGGTCACCTTTGAAGGAGTCCAATCTCACCATGTCTGCATCGATGTCATCCATCTG
A12_BOLC.VG2.B    2620 CTATTGGTCACCTTTGAAGGAGTCCAATCTCACCATGTCTGCATCGATGTCATCCATCTG
GD33_BOLC.VG2.B   2619 CTATTGGTCACCTTTGAAGGAGTCCAATCTCACCATGTCTGCATCGATGTCATCCATCTG

A12_BOLC.VG2.A    2778 GTATGTGAATATTCAGCTTACCTTCCACTATTGTTTCTT-GTTATGTTAAGTGATTTTTT
GD33_BOLC.VG2.A   2808 GTATGTGAATATTCAGCTTACCTTCCACTATTGTTTCTT-GTTATGTTAAGTGATTTTTT
A12_BOLC.VG2.B    2680 GTATGTGAATATTCAGCTTACCTTCCACTATTGTTTCTT-GTTAT----AGTGATTTTTT
GD33_BOLC.VG2.B   2679 GTATGTGAATATTCAGCTTACCTTCCACTATTGTTTCTT-GTTAT----AGTGATTTTTT

A12_BOLC.VG2.A    2837 TCG-----------TTTCTTCG----AGTAGATTCTAATCTATGAAAATATTTCAACTTG
GD33_BOLC.VG2.A   2867 TCG-----------TTTCTTCG----AGTAGATTCTAATCTATGAAAATATTTCAACTTG
A12_BOLC.VG2.B    2735 TCG-----------TTTCTTCG----AGTAGATTCTAATCTATGAAAATATTTCAACTTG
```

-continued

| | | |
|---|---|---|
| GD33_BOLC.VG2.B | 2734 | TCG-----------TTTCTTCG----AGTAGATTCTAATCTATGAAAATATTTCAACTTG |
| A12_BOLC.VG2.A | 2882 | TTGTTATTAGGCAAACTT-------CTTTTG--AGTGTATTTTTTTCC------------ |
| GD33_BOLC.VG2.A | 2912 | TTGTTATTAGGCAAACTT-------CTTTTG--AGTGTATTTTTTTCC------------ |
| A12_BOLC.VG2.B | 2780 | TTGTTATTAGGCAAACTT-------CTTTTG--AGTGTATTTTTTTCC------------ |
| GD33_BOLC.VG2.B | 2779 | TTGTTATTAGGCAAACTT-------CTTTTG--AGTGTATTTTTTTCC------------ |
| A12_BOLC.VG2.A | 2921 | --------ACTTATTGTTAGACATAC-------AGTATGTC--------ACATACTATTG |
| GD33_BOLC.VG2.A | 2951 | --------AGTTATTGTTAGACATAC-------AGTATGTC--------ACATACTATTG |
| A12_BOLC.VG2.B | 2819 | --------AGTTATTGTTAGACATAC-------AGTATGTC--------ACATACTATTG |
| GD33_BOLC.VG2.B | 2818 | --------AGTTATTGTTAGACATAC-------AGTATGTC--------ACATACTATTG |
| A12_BOLC.VG2.A | 2958 | TAAATTACAGTATATCTGACGTTAATGAAAATGCTCGAATCACAGATGTTGATGCCTCTT |
| GD33_BOLC.VG2.A | 2988 | TAAATTACAGTATATCTGACGTTAATGAAAATGCTCGAATCACAGATGTTGATGCCTCTT |
| A12_BOLC.VG2.B | 2856 | TAAATTACAGTATATCTGACGTTAATGAAAATGCTCGAATCACAGATGTTGATGCCTCTT |
| GD33_BOLC.VG2.B | 2855 | TAAATTACAGTATATCTGACGTTAATGAAAATGCTCGAATCACAGATGTTGATGCCTCTT |
| A12_BOLC.VG2.A | 3018 | TATTATAATCTTTCTGGAGAGAGTTTGGAAAATAGTTTCATGTTCGTCATTCTCAT---- |
| GD33_BOLC.VG2.A | 3048 | TATTATAATCTTTCTGGAGAGAGTTTGGAAAATAGTTTCATGTTCGTCATTCTCAT---- |
| A12_BOLC.VG2.B | 2916 | TATTATAATCTTTCTGGAGAGAGTTTGGAAAATAGTTTCATGTTCGTCTTTCTCAT---- |
| GD33_BOLC.VG2.B | 2915 | TATTATAATCTTTCTGGAGAGAGTTTGGAAAATAGTTTCATGTTCGTCTTTCTCAT---- |
| A12_BOLC.VG2.A | 3074 | ----------------------GGACAGGTGTCACTCTGCACTTATCTAGTCATTCTCTT |
| GD33_BOLC.VG2.A | 3104 | ----------------------GGACAGGTGTCACTCTGCACTTATCTAGTCATTCTCTT |
| A12_BOLC.VG2.B | 2972 | ----------------------GGACAGGTGTCACTCTGCACTTATCTAGTCATTCTCTT |
| GD33_BOLC.VG2.B | 2971 | ----------------------GGACAGGTGTCACTCTGCACTTATCTAGTCATTCTCTT |
| A12_BOLC.VG2.A | 3112 | TTTTAGTCTCCTAA----------TTTGAGTTTATTTCGATTGATTTGCTTCCCTTAGTT |
| GD33_BOLC.VG2.A | 3142 | TTTTAGTCTCCTAACCCGGCAACATTTGAGTTTATTTCGATTGATTTGCTTCCCTTAGTT |
| A12_BOLC.VG2.B | 3010 | TTTTAGTCTCCTAA----------TTTGAGTTTATTTCGATTGATTTGCTTCCCTTAGTT |
| GD33_BOLC.VG2.B | 3009 | TTTTAGTCTCCTAA----------TTTGAGTTTATTTCGATTGATTTGCTTCCCTTAGTT |
| A12_BOLC.VG2.A | 3162 | ATTATCAATTTACTCCACTGTATTATATGGACATGACTCATATCTAGTCCAAACTTTTGT |
| GD33_BOLC.VG2.A | 3202 | ATTATCAATTTACTCCACTGTATTATATGGACATGACTCATATCTAGTCCAAACTTTTGT |
| A12_BOLC.VG2.B | 3060 | ATTATCAATTTACTCCACTGTATTATATGGACATGACTCATATCTAGTCCAAACTTTTGT |
| GD33_BOLC.VG2.B | 3059 | ATTATCAATTTACTCCACTGTATTATATGGACATGACTCATATCTAGTCCAAACTTTTGT |
| A12_BOLC.VG2.A | 3222 | TTCAGGTGTTTTCTGCTTATGGCTTCGTGCACAAAATTGCCACTTTTGAGAAAGCTGCTG |
| GD33_BOLC.VG2.A | 3262 | TTCAGGTGTTTTCTGCTTATGGCTTCGTGCACAAAATTGCCACTTTTGAGAAAGCTGCTG |
| A12_BOLC.VG2.B | 3120 | TTCAGGTGTTTTCTGCTTATGGCTTCGTGCACAAAATTGCCACTTTTGAGAAAGCTGCTG |
| GD33_BOLC.VG2.B | 3119 | TTCAGGTGTTTTCTGCTTATGGCTTCGTGCACAAAATTGCCACTTTTGAGAAAGCTGCTG |
| A12_BOLC.VG2.A | 3282 | GTTTCCAGGTTAGAGATATCGAGTTTTGTTTTCAAGGTCTTGCAT--------A--AATC |
| GD33_BOLC.VG2.A | 3322 | GTTTCCAGGTTAGAGATATCGAGTTTTGTTTTCAAGGTCTTGCCT--------A--AATC |
| A12_BOLC.VG2.B | 3180 | GTTTCCAGGTTAGAGATATCGAGTTTTGTTTTCAAGGTCTTGCCTTTTTCATAA--AATC |
| GD33_BOLC.VG2.B | 3179 | GTTTCCAGGTTAGAGATATCGAGTTTTGTTTTCAAGGTCTTGCCTTTTTCATAA--AATC |

-continued

```
A12_BOLC.VG2.A     3332 TAATGATGTTTAAACTCATCGTCTGCCGTCATAACCTGCTCAGGCACTTGTTCAGTTTAC
GD33_BOLC.VG2.A    3372 TAATGATGTTTAAACTCATCGTCTGCCGTCATAACCTGCTCAGGCACTTGTTCAGTTTAC
A12_BOLC.VG2.B     3238 TAATGATGTTTAAACTCATCATCTGCCGTCATAACCTGCTCAGGCACTTGTTCAGTTTAC
GD33_BOLC.VG2.B    3237 TAATGATGTTTAAACTCATCATCTGCCGTCATAACCTGCTCAGGCACTTGTTCAGTTTAC

A12_BOLC.VG2.A     3392 TGATGTGGACACTGCCTTAGCGGCAAGGACTGCGCTGGATGGTAGAAGTATACCCAAGTA
GD33_BOLC.VG2.A    3432 TGATGTGGACACTGCCTTAGCGGCAAGGACTGCGCTGGATGGTAGAAGTATACCCAAGTA
A12_BOLC.VG2.B     3298 TGATGTGGACACTGCCTTAGCGGCAAGGACTGCGCTGGATGGTAGAAGTATACCCACGTA
GD33_BOLC.VG2.B    3297 TGATGTGGACACTGCCTTAGCGGCAAGGACTGCGCTGGATGGTAGAAGTATACCCACGTA

A12_BOLC.VG2.A     3452 TGCTCAAATCCTTCATTCATGCTTTTGACCATAAGATAAAGCTCTGTTGATGGTTTCTTC
GD33_BOLC.VG2.A    3492 TGCTCAAATCCTTCATTCATGCTTTTGACCATAAGATAAAGCTCTGTTGATGGTTTCTTC
A12_BOLC.VG2.B     3358 TGCTCAAATCCTTCATTCATGCTTTTGACCATAAGATAAAGCTCTGTTGATGGTTTCTTC
GD33_BOLC.VG2.B    3357 TGCTCAAATCCTTCATTCATGCTTTTGACCATAAGATAAAGCTCTGTTGATGGTTTCTTC

A12_BOLC.VG2.A     3512 CTTTTCTTTTGGTAAATTCAGATATCTGCTTCCAGAACATGTAGGCTCATGCAATTTGCG
GD33_BOLC.VG2.A    3552 CTTTTCTTTTGGTAAATTCAGATATCTGCTTCCAGAACATGTAGGCTCATGCAATTTGCG
A12_BOLC.VG2.B     3418 CTTTTCTTTTGGTAAATTCAGATATCTGCTTCCAGAACATGTAGGCTCATGCAATTTGCG
GD33_BOLC.VG2.B    3417 CTTTTCTTTTGGTAAATTCAGATATCTGCTTCCAGAACATGTAGGCTCATGCAATTTGCG

A12_BOLC.VG2.A     3572 AATGTCTTACTCAGCTCATACTGATCTAAATATCAAATTTCAGTCCCACCGCAGCAGGTA
GD33_BOLC.VG2.A    3612 AATGTCTTACTCAGCTCATACTGATCTAAATATCAAATTTCAGTCCCACCGCAGCAGGTA
A12_BOLC.VG2.B     3478 AATGTCTTACTCAGCCCACACTGATCTAAATATCAAATTTCAGTCCCACCGCAGCAGGTA
GD33_BOLC.VG2.B    3477 AATGTCTTACTCAGCCCACACTGATCTAAATATCAAATTTCAGTCCCACCGCAGCAGGTA

A12_BOLC.VG2.A     3632 GAGTTTTGAGTCCTCGCAAATGTGCCTCTCCATTGTTATACTGCTCTTACTGTTGGAAGC
GD33_BOLC.VG2.A    3672 GAGTTTTGAGTCCTCGCAAATGTGCCTCTCCATTGTTATACTGCTCTTACTGTTGGAAGC
A12_BOLC.VG2.B     3538 GAGTTTTGAGTCCTCGCAAATGTGCCATTCCATTGTTTTACTGCTCCTACTGTTGGAAGC
GD33_BOLC.VG2.B    3537 GAGTTTTGAGTCCTCGCAAATGTGCCATTCCATTGTTTTACTGCTCCTACTGTTGGAAGC

A12_BOLC.VG2.A     3692 CTTATGGTTGAATAGTTACTTCATGTGTTT-AATTCTCTTACGCACTCAGGGACTACACA
GD33_BOLC.VG2.A    3732 CTTATGGTTGAATAGTTACTTCATGTGTTT-AATTCTCTTACGCACTCAGGGACTACACA
A12_BOLC.VG2.B     3598 CTTATGGTTGAATAGTTGATTCATGTGTTTTGATTTTCTGACGTACTCAGGGACTACACA
GD33_BOLC.VG2.B    3597 CTTATGGTTGAATAGTTGATTCATGTGTTTTGATTTTCTGACGTACTCAGGGACTACACA

A12_BOLC.VG2.A     3751 AATCCATACCTTCCGGTGAATCAAACCGCTATGGACGGTTCTATGCAGGTATATTTTTCC
GD33_BOLC.VG2.A    3791 AATCCATACCTTCCGGTGAATCAAACCGCTATGGACGGTTCTATGCAGGTATATTTTTCC
A12_BOLC.VG2.B     3658 AATCCATATCTTCCGGTGAATCAAACTGCTATGGATGGTTCTATGCAGGTAAATATTTCC
GD33_BOLC.VG2.B    3657 AATCCATATCTTCCGGTGAATCAAACTGCTATGGATGGTTCTATGCAGGTAAATATTTCC

A12_BOLC.VG2.A     3811 TTTGATCTAATCTTATCTCCAACAGCTTATATTATTCTTACACTGAATGCGTTTGTATTA
GD33_BOLC.VG2.A    3851 TTTGATCTAATCTTATCTCCAACAGCTTATATTATTCTTACACTGAATGCGTTTGTATTA
A12_BOLC.VG2.B     3718 TCTT-TCTACTCT-ATCTCCAACAGCTTAGACAATTCTTACATTGAATGCGTT-------
GD33_BOLC.VG2.B    3717 TCTT-TCTACTCT-ATCTCCAACAGCTTAGACAATTCTTACATTGAATGCGTT-------

A12_BOLC.VG2.A     3871 CGTTACTGATCGTCTTTGTCCATCACTGCGTTCAGCCTGCTTTGGGTGCTGATGGAAAGA
GD33_BOLC.VG2.A    3911 CGTTACTGATCGTCTTTGTCCATCACTGCGTTCAGCCTGCTTTGGGTGCTGATGGAAAGA
```

-continued

```
A12_BOLC.VG2.B     3769  ----ACTGATTGTCTTTGAC-CTCATTGCATTCAGCCTGCTTTGGGTGCTGATGGAAAGA
GD33_BOLC.VG2.B    3768  ----ACTGATTGTCTTTGAC-CTCATTGCATTCAGCCTGCTTTGGGTGCTGATGGAAAGA

A12_BOLC.VG2.A     3931  GGGTTGAAACTCAGAGCAACGTCCTCCTTGCTTTGATTGAGAATATGCAGTACGCTGTCA
GD33_BOLC.VG2.A    3971  GGGTTGAAACTCAGAGCAACGTCCTCCTTGCTTTGATTGAGAATATGCAGTACGCTGTCA
A12_BOLC.VG2.B     3824  GGGTAGAAACTCAGAGCAACGTCCTCCTTGCTTTGATTGAGAATATGCAATACGCTGTCA
GD33_BOLC.VG2.B    3823  GGGTAGAAACTCAGAGCAACGTCCTCCTTGCTTTGATTGAGAATATGCAATACGCTGTCA

A12_BOLC.VG2.A     3991  CCGTGGATGTTCTTCACACGGTGAGGAACAACATT-ATGCCTGTTTCTTCATCTCATCAT
GD33_BOLC.VG2.A    4031  CCGTGGATGTTCTTCACACGGTGAGGAACAACATT-ATGCCTGTTTCTTCATCTCATCAT
A12_BOLC.VG2.B     3884  C----------------ACGGTGAGGAACACCATT-ATGCACGTTTCTGCATCTCAGCAT
GD33_BOLC.VG2.B    3883  C----------------ACGGTGAGGAACACCATT-ATGCACGTTTCTGCATCTCAGCAT

A12_BOLC.VG2.A     4050  GCTTTCATATCTCAAAATTAACTATT-CCTTTGCTTCTCATAGGTGTTTTCCGCTTATGG
GD33_BOLC.VG2.A    4090  GCTTTCATATCTCAAAATTAACTATT-CCTTTGCTTCTCATAGGTGTTTTCCGCTTATGG
A12_BOLC.VG2.B     3927  CCTTTCATTTCTCAAAATTAATTATTTCCTTTGCTTGTCATAGGTGTTTTCCGCTTATGG
GD33_BOLC.VG2.B    3926  CCTTTCATTTCTCAAAATTAATTATTTCCTTTGCTTGTCATAGGTGTTTTCCGCTTATGG

A12_BOLC.VG2.A     4109  AACTGTGCAGAAGATTGCAATATTTGAGAAAAATGGTTCAACGCAAGCCTTAATTCAATA
GD33_BOLC.VG2.A    4149  AACTGTGCAGAAGATTGCAATATTTGAGAAAAATGGTTCAACGCAAGCCTTAATTCAATA
A12_BOLC.VG2.B     3987  AACTGTGCAGAAGATTGCAATATTTGAGAAAAATGGTTCAACGCAAGCCTTAATTCAATA
GD33_BOLC.VG2.B    3986  AACTGTGCAGAAGATTGCAATATTTGAGAAAAATGGTTCAACGCAAGCCTTAATTCAATA

A12_BOLC.VG2.A     4169  CTCTGGTACATGACCTTGATGATCTGAATACATATATGATTCTACTATACTTCTTTTGGT
GD33_BOLC.VG2.A    4209  CTCTGGTACATGACCTTGATGATCTGAATACATATATGATTCTACTATACTTCTTTTGGT
A12_BOLC.VG2.B     4047  CTCTGGTACATGACCTTGATGATCTGAATACATATATTATTCTACTATACTTCTTTCGGT
GD33_BOLC.VG2.B    4046  CTCTGGTACATGACCTTGATGATCTGAATACATATATTATTCTACTATACTTCTTTCGGT

A12_BOLC.VG2.A     4229  TATATGGTGAATCTTCTTATGTGTATGCAAAGAGAAGAGCCTAAGAATTTGAATATAGTC
GD33_BOLC.VG2.A    4269  TATATGGTGAATCTTCTTATGTGTATGCAAAGAGAAGAGCCTAAGAATTTGAATATAGTC
A12_BOLC.VG2.B     4107  TATATGGCGAATCATCTTATGTGTATGC-------------TAAGAATTTGAAT--AGTC
GD33_BOLC.VG2.B    4106  TATATGGCGAATCATCTTATGTGTATGC-------------TAAGAATTTGAAT--AGTC

A12_BOLC.VG2.A     4289  ATCTTTTGCTTCATGTTCCGTTTTATTGATTCTTCTGTAGACATTTCAACGGCGACAATG
GD33_BOLC.VG2.A    4329  ATCTTTTGCTTCATGTTCCGTTTTATTGATTCTTCTGTAGACATTTCAACGGCGACAATG
A12_BOLC.VG2.B     4152  ATCTTTTGCTTCATGTTCCGTTTTCTTGATTCTTCTGTAGACATACCAACGGCGACAATG
GD33_BOLC.VG2.B    4151  ATCTTTTGCTTCATGTTCCGTTTTCTTGATTCTTCTGTAGACATACCAACGGCGACAATG

A12_BOLC.VG2.A     4349  GCGAAAGAAGCACTGGAGGGACACTGCATATATGACGG-AGGCTACTGTAAGCTTCGACT
GD33_BOLC.VG2.A    4389  GCGAAAGAAGCACTGGAGGGACACTGCATATATGACGG-AGGCTACTGTAAGCTTCGACT
A12_BOLC.VG2.B     4212  GCGAAAGAAGCATTGGAGGGACACTGCATATATGACGGGAGGCTACTGTAAGCTTCGACT
GD33_BOLC.VG2.B    4211  GCGAAAGAAGCATTGGAGGGACACTGCATATATGACGGGAGGCTACTGTAAGCTTCGACT

A12_BOLC.VG2.A     4408  AACTTACTCTCGGCATACTGATCTCAATGTAAAGGTACATAAGATCAGTTGCTTT-----
GD33_BOLC.VG2.A    4448  AACTTACTCTCGGCATACTGATCTCAATGTAAAGGTACATAAGATCAGTTGCTTT-----
A12_BOLC.VG2.B     4272  AACATACTC--GTCATACTGATCTCAATGTAAAGGTACATAAGATCAGTTGCTTTCTTGA
GD33_BOLC.VG2.B    4271  AACATACTC--GTCATACTGATCTCAATGTAAAGGTACATAAGATCAGTTGCTTTCTTGA
```

-continued

```
A12_BOLC.VG2.A     4463  ---▒TGTACCCAAACAAAAA-GT▒C▒GTTAAAGAGAATAAGAA▒T▒ATTTCTGCAAGAAC
GD33_BOLC.VG2.A    4503  ---▒TGTACCCAAACAAAAA-GT▒C▒GTCAAAGAGAATAATAA▒T▒ATGTCTGCAAGAAC
A12_BOLC.VG2.B     4330  TTTGTGCACCCAAACAAAAAAGCTT▒GGGAAAGAGAATAATAACTTATGTCTGCAAGAAC
GD33_BOLC.VG2.B    4329  TTTGTGCACCCAAACAAAAAAGCTT▒GGGAAAGAGAATAATAACTTATGTCTGCAAGAAC

A12_BOLC.VG2.A     4519  CGCATGCT----TTTTTCTCATCAACAATTG--AGTGAAATCTGAATTCGAC▒TTCTAGT
GD33_BOLC.VG2.A    4559  CGCATGCT----TTTTTCTCATCAACAATTG--AGTGAAATCTGAATTCGAC▒TTCTAGT
A12_BOLC.VG2.B     4390  C▒TATGCTATTTTTTTTCTCTTCAACAATTG--T▒TGAAATCTGAATTCGACTTTCTAGT
GD33_BOLC.VG2.B    4389  C▒TATGCTATTTTTTTTCTCTTCAACAATTG--T▒TGAAATCTGAATTCGACTTTCTAGT

A12_BOLC.VG2.A     4573  T▒ATTCAACTAATGATTTT-CGTCTTCTTTCTTCAGGCATTTAGCGACAAAAGCAGAGAC
GD33_BOLC.VG2.A    4613  T▒ATTCAACTAATGATTTT-CGTCTTCTTTCTTCAGGCATTTAGCGACAAAAGCAGAGAC
A12_BOLC.VG2.B     4448  TTATTCAACTA▒TGATTTTTCGTCTTCTTTCTTCAGGCATTTAGTGACAAAAGC▒GAGAC
GD33_BOLC.VG2.B    4447  TTATTCAACTA▒TGATTTTTCGTCTTCTTTCTTCAGGCATTTAGCGACAAAAGC▒GAGAC

A12_BOLC.VG2.A     4632  TACACACTGCCTGATCTAAGCCAACTGGTGGGCCAAAAGGTTCCAGGAGTGGCTGCAGCT
GD33_BOLC.VG2.A    4672  TACACACTGCCTGATCTAAGCCAACTGGTGGGCCAAAAGGTTCCAGGAGTGGCTGCAGCT
A12_BOLC.VG2.B     4508  TACACACTGCCTGATCTAAGCCAACTGGTGGGCCAAAAGGTTCCAGGAGTGGCCGCTGCT
GD33_BOLC.VG2.B    4507  TACACACTGCCTGATCTAAGCCAACTGGTGGGCCAAAAGGTTCCAGGAGTGGCCGCTGCT

A12_BOLC.VG2.A     4692  AGTGGGCCAACAGATGGTTGGCCCAATGGGCAGGTGCAGACTCAATACAT▒GG-------
GD33_BOLC.VG2.A    4732  AGTGGGCCAACAGATGGTTGGCCCAATGGGCAGGTGCAGACTCAATACAT▒GG-------
A12_BOLC.VG2.B     4568  AGTGGGCCAACAGATTGTTGGCACAATGGGCAGGTGCAGACTCAATACACA▒G-------
GD33_BOLC.VG2.B    4567  AGTGGGCCAACAGATTGTTGGCACAATGGGCAGGTGCAGACTCAATACACA▒G-------

A12_BOLC.VG2.A     4745  --AAGTTC▒TATATGTACCCACC--A▒CTGATCCCAGAGGAGCTTCACCTTCTTCTGGTC
GD33_BOLC.VG2.A    4785  --AAGTTC▒TATATGTACCCACC--A▒CTGATCCCAGAGGAGCTTCACCTTCTTCTGGTC
A12_BOLC.VG2.B     4621  --AAGTTCATATATGTACCCACTGTA▒GC▒AAGGTACT▒GATTTTGATAAAGCGC▒▒GTT
GD33_BOLC.VG2.B    4620  --AAGTTCATATATGTACCCACTGTA▒GC▒AAGGTACT▒GATTTTGATAAAGCGC▒▒GTT

A12_BOLC.VG2.A     4801  -ATCCTC---CTTATTATC▒TTGATCCAT▒TACTGT---TTTCT▒CTTTATATAA-ATTT
GD33_BOLC.VG2.A    4841  -ATCCTC---CTTATTATC▒TTGATCCAT▒TACTGT---TTTCT▒CTTTATATAA-ATTT
A12_BOLC.VG2.B     4679  TATTTTTAATTTTTTTTC▒ATTGACAAAT▒TTTAGTAAATGTC▒TATTTTCATAT-ATTT
GD33_BOLC.VG2.B    4678  TATTTTTAATTTTTTTTC▒ATTGACAAAT▒TTTAGTAAATGTC▒TATTTTCATAT-ATTT

A12_BOLC.VG2.A     4853  CGGATTAT▒TTGAAGACTACTTTCCATGTTATAGGTTTCA▒GTAA▒AGTGT▒TTGTTCTT
GD33_BOLC.VG2.A    4893  CGGATTAT▒TTGAAGACTACTTTCCATGTTATAGGTTTCA▒GTAA▒AGTGT▒TTGTTCTT
A12_BOLC.VG2.B     4738  -GT▒TTTT▒TTTTATAAAAG▒CTTAAACTTTTT▒TCTTTATTTAT---CGT▒TT-TTATT
GD33_BOLC.VG2.B    4737  -GT▒TTTT▒TTTTATAAAAG▒CTTAAACTTTTT▒TCTTTATTTAT---CGT▒TT-TTATT
```

-continued

```
A12_BOLC.VG2.A    4913  TATTTG[illegible]TTAAATAA[illegible]CA---TGGGAAAACCAATAATATTATAGTA[illegible]T[illegible]TAATTT[illegible]TA[illegible]

GD33_BOLC.VG2.A   4953  TATTTG[illegible]TTAAATAA[illegible]CA---TGGGAAAACCAATAATATTAT-----------------

A12_BOLC.VG2.B    4793  TTA[illegible]ATG[illegible]CTATTTAT[illegible]TT---T[illegible][illegible][illegible]AAATTAAACTTTATTTCTTTAATGAATTA[illegible][illegible]TTG

GD33_BOLC.VG2.B   4792  TTA[illegible]ATG[illegible]CTATTTAT[illegible]TT---T[illegible][illegible][illegible]AAATTAAACTTTATTTCTTTAATGAATTA[illegible][illegible]TTG


A12_BOLC.VG2.A    4970  ACATT[illegible]TGTATTT[illegible]TTTCTATTTGACTTTGTT[illegible]TG[illegible]AGCTTCC[illegible]AAGT[illegible]TTA[illegible]A[illegible]CTT--

GD33_BOLC.VG2.A         ----------------------------------------------------------
A12_BOLC.VG2.B    4850  ATATAACTCTGATAAATTAATTTTATTATGTGGTTAATATTTT[illegible]ATTAAA[illegible]AAA[illegible]TTATA

GD33_BOLC.VG2.B   4849  ATATAACTCTGATAAATTAATTTTATTATGTGGTTAATATTTT[illegible]ATTAAA[illegible]AAA[illegible]TTATA


A12_BOLC.VG2.A    5028  --CTTTTTCTC[illegible]T[illegible]CTTT[illegible]AACTGTTTCATTCCT[illegible][illegible]ATTT[illegible]TTTGAAGATCTGCAG[illegible]CTT

GD33_BOLC.VG2.A         ----------------------------------------------------------
A12_BOLC.VG2.B    4910  TACTTTT[illegible]ATA[illegible][illegible]GATTT[illegible]TATTTTTC[illegible]AT[illegible]AA[illegible][illegible][illegible]ATTCAATTTTTTTATGAAT[illegible]CTT

GD33_BOLC.VG2.B   4909  TACTTTT[illegible]ATA[illegible][illegible]GATTT[illegible]TATTTTTC[illegible]AT[illegible]AA[illegible][illegible][illegible]ATTCAATTTTTTTATGAAT[illegible]CTT


A12_BOLC.VG2.A    5086  ACACTTTAGT[illegible]ACTTTTG[illegible]TATCC (SEQ ID NO: 7)

GD33_BOLC.VG2.A         ------------------------ (SEQ ID NO: 8)
A12_BOLC.VG2.B    4970  AAATTATATT[illegible]AGAAAAG[illegible]AAAGA (SEQ ID NO: 9)

GD33_BOLC.VG2.B   4969  AAATTATATT[illegible]AGAAAAG[illegible]AAAGA (SEQ ID NO: 10)
```

Protein sequence alignment of VG2 *Brassica oleracea* orthologue proteins from GD33 and A12. Protein sequences were predicted using the web based bioinformatic program FGENESH (on the World Wide web at softberry.com).

```
A12_BOLC.VG2.A      1 ---M[illegible]SSQFRYTQTPSKVVHLRNLPWECVEEELIDLCKRFGKIVNTKTNVGANRNQAFVE
GD33_BOLC.VG2.A     1 ---M[illegible]SSQFRYTQTPSKVVHLRNLPWECVEEELIDLCKRFGKIVNTKTNVGANRNQAFVE
A12_BOLC.VG2.B      1 --MASSSQFRYTQTPSKVVHLRNLPWECVEEELIDLCKRFGKIVNTKTNVGANRNQAFVE
GD33_BOLC.VG2.B     1 --MASSSQFRYTQTPSKVVHLRNLPWECVEEELIDLCKRFGKIVNTKTNVGANRNQAFVE

A12_BOLC.VG2.A     58 FGDVNQAISMVSYYASSSEPAQIRGKTVYIQYSNRHEIVNNQSPGEVPGNVLLVTFEGVQ
GD33_BOLC.VG2.A    58 FGDVNQAISMVSYYASSSEPAQIRGKTVYIQYSNRHEIVNNQSPGEVPGNVLLVTFEGVQ
A12_BOLC.VG2.B     59 FGDVNQAISMVSYYASSSEPAQIRGKTVYIQYSNRHEIVNNQSPGEVPGNVLLVTFEGVQ
GD33_BOLC.VG2.B    59 FGDVNQAISMVSYYASSSEPAQIRGKTVYIQYSNRHEIVNNQSPGEVPGNVLLVTFEGVQ

A12_BOLC.VG2.A    118 SHHVCIDVIHLVFSAYGFVHKIATFEKAAGFQALVQFTDVDTALAARTALDGRSIPKYLL
GD33_BOLC.VG2.A   118 SHHVCIDVIHLVFSAYGFVHKIATFEKAAGFQALVQFTDVDTALAARTALDGRSIPKYLL
A12_BOLC.VG2.B    119 SHHVCIDVIHLVFSAYGFVHKIATFEKAAGFQALVQFTDVDTALAARTALDGRSIPTYLL
GD33_BOLC.VG2.B   119 SHHVCIDVIHLVFSAYGFVHKIATFEKAAGFQALVQFTDVDTALAARTALDGRSIPTYLL

A12_BOLC.VG2.A    178 PEHVGSCNLRMSYSAHTDLNIKFQSHRSRDYTNPYLPVNQTAMDGSMQPALGADGK[illegible]VE[illegible]
GD33_BOLC.VG2.A   178 PEHVGSCNLRMSYSAHTDLNIKFQSHRSRDYTNPYLPVNQTAMDGSMQPALGADGK[illegible]VE[illegible]
A12_BOLC.VG2.B    179 PEHVGSCNLRMSYSAHTDLNIKFQSHRSRDYTNPYLPVNQTAMDGSMQ------------
GD33_BOLC.VG2.B   179 PEHVGSCNLRMSYSAHTDLNIKFQSHRSRDYTNPYLPVNQTAMDGSMQ------------

A12_BOLC.VG2.A    238 QSNVLL[illegible]LIENMQYAVTVDVLHTVFSAYGTVQKIAIFEKNGSTQALIQYSDISTATMAKE
GD33_BOLC.VG2.A   238 QSNVLL[illegible]LIENMQYAVTVDVLHTVFSAYGTVQKIAIFEKNGSTQALIQYSDISTATMAKE
A12_BOLC.VG2.B    227 -----------------------VFSAYGTVQKIAIFEKNGSTQALIQYSDIPTAT[illegible]AKE
GD33_BOLC.VG2.B   227 -----------------------VFSAYGTVQKIAIFEKNGSTQALIQYSDIPTAT[illegible]AKE

A12_BOLC.VG2.A    298 ALEGHCIYDGGYCKLRL[illegible]YSRHTDLNVKAFSDKSRDYTLPDLSQLVGQKVPGVAAASGPT
G GD33_BOLC.VG2.A 298 ALEGHCIYDGGYCKLRL[illegible]YSRHTDLNVKAFSDKSRDYTLPDLSQLVGQKVPGVAAASGPT
A12_BOLC.VG2.B    264 ALEGHCIYDG------------------RLLDKSGDYTLPDLSQLVGQKVPGVAAASGPT
GD33_BOLC.VG2.B   264 ALEGHCIYDG------------------RLLDKSGDYTLPDLSQLVGQKVPGVAAASGPT

A12_BOLC.VG2.A    358 DGWP-NGQVQTQYMGSSYMYPPADPTGASPSSGHPPYYG  (SEQ ID NO: 11)
GD33_BOLC.VG2.A   358 DGWP-NGQVQTQYMGSSYMYPPADPTGASPSSGHPPYYG  (SEQ ID NO: 12)
A12_BOLC.VG2.B    306 DCWH--NGQVQTQYTRSSYMYPL----------------- (SEQ ID NO: 13)
GD33_BOLC.VG2.B   306 DCWH--NGQVQTQYTRSSYMYPL----------------- (SEQ ID NO: 14)
```

DNA Sequence Alignment for the VG1 *Brassica oleracea* Genes

```
A12      1 AAAAAGCAGGCTAAGAGTGTAAGCGACCCATTTCACATCGGATCTAAAAATCATATAATC
GD33     1 AAAAAGCAGGCTAAGAGTGTAAGCGACCCATTTCACATTGGATCTAAAAATCAAATAATC

A12     61 TAGAGTCTGACAAGAATCAACGTTGATAGAGAGTGCGAGAGAATAGTACAGAGCCAGTCG
GD33    61 TAGAGTGTGACAAGAATCAACGTTGATAGAGAGTGAGAGAGAATAGTACAGAGCCAGTCG

A12    121 TCGAGGTAGAAATGTTTGTCCTGAGCCCAAATGGTATAGTTGATATTGGGATTCCAGAAC
GD33   121 TCGAGGTAGAAATGTTTGTCCTGAGCCCAAATGGTATAGTTGATATTGGGATTCCAGAAC

A12    181 TTGTTATCACCCACTATCCATCTCTTAGCGGCCACCTCAGTCACCGGAGCTGCCGCAAGA
GD33   181 TTGTTATCACCCACTATCCATCTCTTAGCGGCCACCTCAGTCACCGGAGCTGCCGCAAGA

A12    241 AAAGCCAGAACCATTGCCGCAGCCATCAACGCAAGTCTAGCCATAGATCACTCTAGAAAG
GD33   241 AAAGCCAGAACCACTGCCGCAGCCATCAACGCAAGTCTAGCCATAGATCACTCTAGAAAG

A12    301 AAAAAGAAGCTCAGTGCTTAATGACTCTTAGTCTTATCTCTCAAGAAATAGCAGTTTTAT
GD33   301 AAAAAGAAGCTCAGTGCTTGATGACTCTTAGTCTTATCTCTCAAGAAATAGCAGTTTTAT

A12    361 GA TGAATGTATATGAGCGAGTGGGGCTGTTTCCAAGTCAAATCAGACATACAAATTTCT
GD33   361 GA TGA--------------GTGGGGCTGTTTCCAAGTCAAATCAGACATACAAATTTCT

A12    421 CGTTTTACGGGGAAAAGATCTCTCAAGATCCGTAATTTCTTCAACTAACGTTTGGAATTT
GD33   407 TTGTTATCACCCACTATCCATCTCTTAGCGGCCACCTCAGTCACCGGAGCTGCCGCAAGA

A12    481 TATTACTACTTTAATCAACCTCGATGTTGACGATGAAGTACACGTTAATTAAAGGTACGC
GD33   467 TATTACTACTTTAATCAACCTCGATGTTGACGATGACGTACACGTTAATTAAAGGTACGC

A12    541 GTTATATAGTTAAAGGAGTAATTAGATTTTAATTGCTGGCATTATTATTATTTTTCTCTG
GD33   527 GTTATATAGTTAAGGGAGTAATTAGATTTTAACTGCTGGCATTATTATTATTTTTCTCTG

A12    601 GT----ATATT-------TTT AAGGAATATTTTCTCACCTTTTAGGCGGGAATTTATTT
GD33   587 GTTATTACATTATTCTGTTTT TAGTAATATTTTCTCACCTTTTAGGCGGGAATTTATTT

A12    650 CCATTTTCTTCTTTCAAGGGTTCAGAGATTCAATTCCTTTATTAACATACGAAATGAGTA
GD33   647 CCATTTTCTTCTTTCAAGGGTTCAGAGATTCAATTCCTTTATTAACATACGAAATGAGTA

A12    710 TATAGTATCTTTTGAATATTTAAATAATTAAAATAAAAATAAATTACCATAACAGTGATA
GD33   707 TATAGTATCTTTTAAATATTTAAATAATTAAAATAAAAATAAATTACTATAACAGTGATA

A12    770 CATATCAAAATTTCCAAAACTAATGTGAGTACTTATATTAGTTGTACTTCTTAGTAAAAT
GD33   767 CATATCAAAATTTCCAAAACTAATGTGAGTACTTATATTAGTTGTACTTCTTAGTAAAAT

A12    830 AACGAGATATGTTATGGCTCGTCGCATACAACAAAGCAGAGCATATGTTCCCGCAATAAC
GD33   827 AACGAGATATGTTATGGCTCGTCGCATACAGCAAAGCAGAGCATATGTTCCCGCAATAAC

A12    890 ATGCACACGCAACTGATAGCACGTCGTAACCATTTCCGCGAACCAACCAATGGATATTGT
GD33   887 ATGCACACGCAACTGATAGCACGTCGTAACCATTTCCGCGAACCAACCAATGGATATTGT

A12    950 AATTCGATAAGACGACGTCGTGTTGTTGACCACGAATATTTCTTAAATTTCCTTTTATCT
GD33   947 AATTCGATAAGACGACGTCGTGTTGTTGACCACGAATATTTCTTAAATTTCCTTTTATCT

A12   1010 TTTGTTTTTGACGTCATCACATTGGTTTATGTCCACACGATATCAGTCATAAAATCCACG
GD33  1007 TTTGTTTTTGACGTCATGACATTGGTTTATGTCCACACGATATCAGTCATAAAATCCACG

A12   1070 TAGGGAACGACTATCCATTACACCCATCCACGTGTTCTCATAACAGCTTCTAGTTCCATT
GD33  1067 TAGG-AACGACTATCCATTACACCCATCCACGTGTTCTCATAACAGCTTCTAGTTCCATT

A12   1130 AGCTGAACGAACAATAGAAACAGAGCATCGAACTGAGAAAGAAGAAGAAGAAGGGAAGCA
GD33  1126 AGCTGAACGAACAATAGAAACAGAGCATCGAACTGAGAAAGAAGAAGAAGAAGGGAAGCA

A12   1190 AGAGAAATGGCGGCAGCGGCCATGGCCGTTCATCTCCCGAAACATTCATCGTTTCTTCCT
GD33  1186 AGAGAAATGGCGGCAGCGGCCATGGCCGTTCATCTCCCGAAACATTCATCGTTTCTTACG

A12   1250 AATCCCAAGCTTCCATTG ATCAAAACTCTAACTTCCTCGGTGTGTCCTT AAGATCGGT
GD33  1246 AAACCCAAGCATCCATCC ATCAAAACTCTAACTTTCTCGGTGGGTCCTT AAGTTCGGT

A12   1310 CGACCCATGTCCGTTAACCGGAAAATGAAAGGTCC GTTACGGTTTCAGCTGCTTCGACC
GD33  1306 CGATCCATGTCTCTAAACCGGAAAACTAAAGGTCC GTTATGGTTTCAGCTGCTTCGACC

A12   1370 GTCGAAGGCGATCGAAGCAAACAGTTTTACATAAACTTCACTGGATTCCCATTTCCTCTT
GD33  1366 GTCGAAGGCGATCGAAGCAAACAGTTTTACATAAACTTCACTGGATTCCCATTTCCTCTT

A12   1430 GGTCCTTTCCTTAACCGGCGCACCATCAGAACCGAGGTTAGGCTTTCTCCATCCCTCTTG
GD33  1426 GGTCCTTTCCTTAACCGGCGCACCATCAGAACCGAGGTTAGGCTTTCTCCATCCCTCTTG
```

-continued

```
A12   1490 AGTTTTGATTTGAACTCGTTGAGAATCCCATATGGAT---GTTATGCAGGCGGTTAAAGG
GD33  1486 AGTTTTGATTTGAACTCGTTGAGAATCCCATATGGATAATGTTATGCAGGCGGTTAAAGG

A12   1547 AAGCATATGGATGTTTGAACAAGAACAAGCTTTAGGTTTCAGCAGTGTCTCTACCAATAT
GD33  1546 AAGCATATGGATGTTTGAACAAGAACAAGCTTTAGGTTTCAGCAGTGTCTCAACGAATAT

A12   1607 AAGAATGACTGTCATCA ACTCAAATCCGGTGGCTTATGGGTTCATGCCCCTATTGCTCC
GD33  1606 AAGAATGACTGTCATCA ACTCAAATCCGGTGGCTTATGGGTTCATGCCCCTATTGCTCC

A12   1667 CACCAAAGAGTGTATTCAGGTTCCCCCTTTTTATTCATTATCCTTGATAAAGTATCATCC
GD33  1666 CACCAAAGAGTGTATTCAGGTTCCCTCTTTT-ATTCATTATC--------AGTATCATCC

A12   1727 TTTCTTATCATTTGATAA--TAACCAATGTCTAAACTCTTTTTTGGGTTGTTTTGCAAAC
GD33  1717 TTTCTTATCATTTGATAAATTAACCAATGTCTAAACTCTATTTTGGGTTGTTTTGCTTAC

A12   1785 TTTTTCTTTG GGCAGCTTATTGAGGAGTTGGGAGCTCCGGTTGAGTACATTGTCCT CC
GD33  1777 TTTTTCTTTG GGCAGCTTATTGAGGAGTTGGGAGCTCCGGTTGAGTACATCGTCCT CC

A12   1845 AACTTTTGCTTACGAGCACAAGATCTTCGTCGGTCCCTTCTCTAGAAAGTTCCCCAAGGC
GD33  1837 AACCTTCGCTTACGAGCACAAGATCTTCGTCGGTCCCTTCTCTAGAAAGTTCCCCAAGGC

A12   1905 TCAAGTATGGGTGGCGCCAAGACAATGGAGCTGGCCACTGAACTTACCACTCGAGTTTTT
GD33  1897 TCAAGTATGGGTGGCGCCAAGACAATGGAGCTGGCCACTGAACTTACCACTCGAGTTTTT

A12   1965 CGGTATCTTTCGCGCTAAAACCATTAAAGACGGAGACTT TCTACCCCGTGGGCTGATGA
GD33  1957 CGGTATCTTTCGCGCTAAAACCATTAAAGACGGTGACTT TCTACCCCGTGGGCTGATGA

A12   2025 GATCGAGCAGAAAGTCTTAAGCTCTCCTGAAGTCGGTACGTTCCTTCACTTTCTCAATCT
GD33  2017 GATCGAGCAGAAAGTCTTAAGCTCTCCTGAAGTCGGTACGTTCCTTCACTTTCTCAATCT

A12   2085 TGTTGGCCCTCCTTAGCCAAGCCTCAGT AAACATTCGCCTAAACCCGCACTCTCCTCCT
GD33  2077 TGTTGGCCCTCCTTAGCCAAGCCTCA-T AAACATTCGCTTCAACCC---CTCACC----

A12   2145 CTTCCCTCCAAAATATTTGAAAA AGTTATATATACATAGCCTCCCAAGTTATTAAAAAA
GD33  2129 ---CCACCCAAATTTTTTGAAAA AGTTACATATACATAGCC-CCAAATTTATTAAAAAA

A12   2205 AACGTTTTGTCTCCCAAACTATTGAAATCTTTATCAAATT TCTAT GCCTCCA AATCC
GD33  2185 ATC----------------TATTGAAATCTTTATTAAATT TCTAC TCCCCTA AATCT

A12   2265 GAGGGTCGGTCCTGTACTTAT AAATAA-TAATATACAGGAATAGGACCGTATGTGGAAG
GD33  2229 GAGGGTCGGCCCTGTACTTAT GAATAAATAATATACAGGAATTGGACCGTATGTGGAAG

A12   2324 TAGCGTTCTACCATAAGCGTTCAAGAACTCTATTAGTCACTGATGCTGTGATCTTCGTCC
GD33  2289 TAGCGTTCTACCATAAGCGTTCAAGAACTCTATTAGTCACCGACGCTGTGATCTTCGTCC

A12   2384 CAC GAAGCCGCCATCGAGTATCAGCAGCGAGTCCTTGCTGGCCTCTGCTAAGAACGGAC
GD33  2349 CAA GAAGCCGCCATCGAGTATCAGCAGCGAGTCTTTGCTGGCTTCTGCTAAGAACGGAC

A12   2444 TGGCTGTGAAGATACTTAGCAAAGGCAAACAAGTACCT ATGACCCTGTCGTTGATACCC
GD33  2409 TGGCTGTGAAGATACTTAGCAAAGGCAAACAAGTACCT ATGACCCTGTCGTTGATACCC

A12   2504 CAAACACCCGCCAAAAAGGTCAGCCATCAGCTTCTTGAAATTCAAATTCATCAAACAAAA
GD33  2469 CAAACACCCGCCAAAAAGGTCAGCCATCAGCTTCTTGAAATTCAAATTCATCAAACAAA-

A12   2564 GATCTC ATGGGTGTCTTTTAACGTGCAGGATGGGAAAGAATGGTGCTGCAAATCCTGTT
GD33  2528 GATCTC ATGGGTGTCTTTTAACGTGCAGGATGGGAAAGAATGGTGCTGCAAATCCTGTT

A12   2624 TCTTGGTCC TCTAATCTCTTGGAGCCAAACGCGAGCTTCGC CAAATGTCACAGAAGCT
GD33  2588 TCTCGGCCC TCTAATCTCTTGGAGCCAAACGCGAGCTTTGC CAAATGTCACAGAAGCT

A12   2684 GATCGTTTCTCCCATTGTCAAGACTCTGGTCTTTAGCAAAGTCCCTGAGAAGGTGAGGGA
GD33  2648 GATAGTTTCTCCCATTGTCAAGACTCTGGTCTTTAGCAAAGTCCCTGAGAAGGTGAGGGA

A12   2744 CTGGATCGATGAGATAGCGAGTGACTGGAG TTCAAGAGGATAATCCCAGCTCATTTCGA
GD33  2708 CTGGATCGATGAGATAGCGAGTGACTGGAG TTCAAGAGGATAATCCCAGCTCATTTCGA

A12   2804 GGCTCCG TAAACGC GGGAGGTCAGA TTTCTAGCTGCGTTTGGGTTTCTTGATGATCT
GD33  2278 GGCTCCG TAAACGC GGGAGGTCAGA TTTCTAGCTGCGTTCGGGTTTCTTGATGATCT

A12   2864 TCTAGGGGAAAGATATGTGAACCGTCCTCCTTCGCTCTCTGTTCTCTTCACTTCGCTGAT
GD33  2828 TCTAGGGGAAAGATATGTGAACCGTCCTCCTTCGCTCTCTGTTCTCTTTACTTCGCTGAT

A12   2924 GGGTAAAGCAGCGAGCTATTTTCCTCCGGATGATATGAG ACTCTCTCTTCTCTTGATCA
GD33  2888 GGGTAAAGCTGCCAGCTATTTTCCTCCGGATGATATGAG ACTCTCTCTTCTCTTGATCA

A12   2984 GTTCTTAGTCTCTGTTGGTGCTGTTAAGAAGACCGTCTCTGGTAGAAAACGAAGATGACG
GD33  2948 GTTCTTAGTCTCTGTTGGTGCTGTTAAGAAGACCGTCTCTGGTAGAAAACGAAGATGACG
```

-continued

A12 3044 GAACAAACCCAGCTTTCT (SEQ ID NO: 15)
GD33 3008 GAACAAACCCAGCTTTCT (SEQ ID NO: 16)

Protein sequence alignment of VG1 *Brassica oleracea* orthologues proteins from A12 and GD33. Protein sequences were predicted using the web based bioinformatic program FGENESH.

A12 1 MAAAAMAVHLPKHSSFLPNPKLPLNQNSNFLGVSLK[illegible]GRPMSVNRKMKGPVTVSAAST--
GD33 1 MAAAAMAVHLPKHSSFLTKPKHPSDQNSNFLGGSLKFGRSMS[illegible]NRKTKGPVMVSAAST--

A12 59 ------VEGDRSKQFYINFTGFPFPLGPFLNRRTIRTEAVKGSIWMFEQEQALGFSSVST
GD33 59 ------VEGDRSKQFYINFTGFPFPLGPFLNRRTIRTEAVKGSIWMFEQEQALGFSSVST

A12 113 NIRMTVI[illegible]LKSGGLWVHAPIAPTKECIQLIEELGAPVEYIVLPTFAYEHKIFVGPFSRKF
GD33 113 NIRMTVIKLKSGGLWVHAPIAPTKECIQLIEELGAPVEYIVLPTFAYEHKIFVGPFSRKF A12 173 PKAQVWVAPRQWSWPLNLPLEFFGIFRAKTIKDGDLSTPWADEIEQKVLSSPEVGIGPYV
GD33 173 PKAQVWVAPRQWSWPLNLPLEFFGIFRAKTIKDGDLSTPWADEIEQKVLSSPEVGIGPYV A12 233 EVAFYHKRSRTLLVTDAVIFVPRKPPSSISSESLLASAKNGLAVKILSKGKQVPDDPVVD
GD33 233 EVAFYHKRSRTLLVTDAVIFVP[illegible]KPPSSISSESLLASAKNGLAVKILSKGKQVPNDPVVD A12 293 IPNTRQKGWERMVLQILFLGPSNLLEPNASFAQMSQKLIVSPIVKTLVFSKVPEKVRDWI
GD33 293 IPNTRQKGWERMVLQILFLGPSNLLEPNASFAQMSQKLIVSPIVKTLVFSKVPEKVRDWI A12 353 DEIASDWRFKRIIPAHFEAP[illegible]NAGRSEFLAAFGFLDDLLGERYVNRPPSLSVLFTSLMGK
GD33 353 DEIASDWRFKRIIPAHFEAPINAGRSEFLAAFGFLDDLLGERYVNRPPSLSVLFTSLMGK A12 413 AASYFPPDDMRTLSSLDQFLVSVGAVKKTVSGRKRR (SEQ ID NO: 17)
GD33 413 AASYFPPDDMRTLSSLDQFLVSVGAVKKTVSGRKRR (SEQ ID NO: 18)

The invention claimed is:

1. A cultivated hybrid *Brassica* plant or plant part which contains within its genome an introgression comprising the nucleotide sequence of SEQ ID NO: 8 at the Speed of Germination (SOG1) QTL from *Brassica oleracea* line SL101, representative seed of line SL101 having been deposited at NCIMB under deposit number NCIMB 41951, and which exhibits an increase in speed of seed germination as compared to a *Brassica* plant or plant part that does not comprise the introgression from *Brassica oleracea* line SL101.

2. The cultivated *Brassica* plant or plant part according to claim 1 that is selected from the group consisting of a *Brassica oleracea, Brassica napus*, and *Brassica rapa* plant or plant part.

3. The cultivated *Brassica* plant or plant part according to claim 1 that is a *Brassica oleracea* plant or plant part.

4. A cultivated hybrid *Brassica* plant or plant part which contains within its genome an introgression comprising the nucleotide sequence of SEQ ID NO: 8 at the Speed of Germination (SOG1) QTL from *Brassica oleracea* line SL101, representative seed of line SL101 having been deposited at NCIMB under deposit number NCIMB 41951, and which exhibits an increase in percentage of seed germination as compared to a *Brassica* plant or plant part that does not comprise the introgression from *Brassica oleracea* line SL101.

5. The cultivated *Brassica* plant or plant part according to claim 4 that is selected from the group consisting of *Brassica oleracea, Brassica napus*, and *Brassica rapa.*

6. The cultivated *Brassica* plant or plant part according to claim 4 that is a *Brassica oleracea* plant or plant part.

7. The cultivated *Brassica* plant or plant part according to claim 1, wherein the plant part is a seed.

8. The cultivated *Brassica* plant or plant part according to claim 3, wherein the plant part is a seed.

9. The cultivated *Brassica* plant or plant part according to claim 4, wherein the plant part is a seed.

10. The cultivated *Brassica* plant or plant part according to claim 6, wherein the plant part is a seed.

11. A seed that produces the cultivated *Brassica* plant or plant part according to claim 1.

12. A seed that produces the cultivated *Brassica* plant or plant part according to claim 3.

13. A seed that produces the cultivated *Brassica* plant or plant part according to claim 4.

14. A seed that produces the cultivated *Brassica* plant or plant part according to claim 6.

* * * * *